United States Patent [19]
Bochis et al.

[11] Patent Number: 5,583,130
[45] Date of Patent: Dec. 10, 1996

[54] BENZO-FUSED LACTAMS PROMOTE RELEASE OF GROWTH HORMONE

[75] Inventors: Richard J. Bochis, East Brunswick; Michael H. Fisher, Ringoes; Robert J. Devita, Westfield; William R. Schoen, Edison; Matthew J. Wyvratt, Mountainside, all of N.J.

[73] Assignee: Merck & Co., Inc., Rahway, N.J.

[21] Appl. No.: 951,681

[22] Filed: Sep. 25, 1992

[51] Int. Cl.$^6$ .......................... A61K 31/47; A61K 31/55; C07D 401/10; C07D 403/10
[52] U.S. Cl. .......................... 514/183; 514/213; 514/312; 514/418; 540/461; 540/523; 546/158; 548/483
[58] Field of Search .................................. 540/461, 523; 546/158; 548/483; 514/183, 213, 312, 418

[56] References Cited

U.S. PATENT DOCUMENTS

| | | |
|---|---|---|
| 3,239,345 | 3/1966 | Hodge et al. |
| 4,036,979 | 7/1977 | Asato. |
| 4,411,890 | 10/1983 | Momany. |
| 4,692,522 | 9/1987 | Parsons et al. .......................... 540/461 |
| 5,206,235 | 4/1993 | Fisher et al. .......................... 514/213 |

FOREIGN PATENT DOCUMENTS

| | | |
|---|---|---|
| 166357 | 1/1986 | European Pat. Off. |
| 253310 | 1/1988 | European Pat. Off. |
| 291969 | 11/1988 | European Pat. Off. |
| 324377 | 7/1989 | European Pat. Off. |
| 349949 | 1/1990 | European Pat. Off. |

OTHER PUBLICATIONS

Jones, et al J. Chem. Soc. c. pp. 2176–2181 (1969).
Davis, et al Arch. Biochem. Biophys 102 pp. 48–51.
Wattley, et al J. Med. Chem. 28 pp. 1511–1516 (1985).
Slade, et al J. Med. Chem. 28 pp. 1517–1521 (1985).
Huang, et al, Synthesis. 10, p. 851 (1984).
Stewart, Australia J. Chem. 33 pp. 633–640 (1980).
Still, et al J. Org. Chem. 43, p. 2923 (1978).
Parsons, W. H., Med. Chem. vol. 32, pp. 1681–1685 (1989).

*Primary Examiner*—Philip I. Datlow
*Attorney, Agent, or Firm*—David L. Rose; Joseph F. DiPrima

[57] ABSTRACT

There are disclosed certain novel compounds identified as benzo-fused lactams which promote the release of growth hormone in humans and animals. This property can be utilized to promote the growth of food animals to render the production of edible meat products more efficient, and in humans, to increase the stature of those afflicted with a lack of a normal secretion of natural growth hormone. The compounds are prepared by substitution of an amino-lactam with a substituted amide function. Growth promoting compositions containing such bezno-fused lactams as the active ingredient thereof are also disclosed.

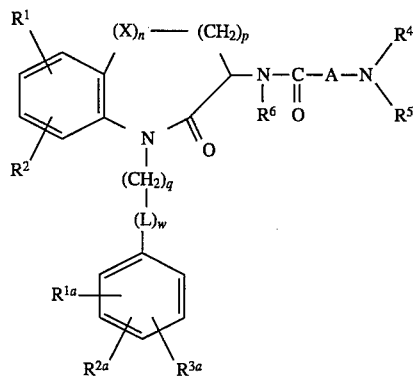

where L is

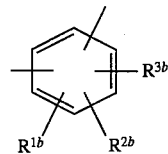

8 Claims, No Drawings

BENZO-FUSED LACTAMS PROMOTE RELEASE OF GROWTH HORMONE

BACKGROUND OF THE INVENTION

Growth hormone, which is secreted from the pituitary, stimulates growth of all tissues of the body that are capable of growing. In addition, growth hormone is known to have the following basic effects on the metabolic process of the body:

1. Increased rate of protein synthesis in all cells of the body;

2. Decreased rate of carbohydrate utilization in cells of the body;

3. Increased mobilization of free fatty acids and use of fatty acids for energy.

A deficiency in growth hormone secretion can result in various medical disorders, such as dwarfism.

Various ways are known to release growth hormone. For example, chemicals such as arginine, L-3,4-dihydroxyphenylalanine (L-DOPA), glucagon, vasopressin, and insulin induced hypoglycemia, as well as activities such as sleep and exercise, indirectly cause growth hormone to be released from the pituitary by acting in some fashion on the hypothalamus perhaps either to decrease somatostatin secretion or to increase the secretion of the known secretagogue growth hormone releasing factor (GRF) or an unknown endogenous growth hormone-releasing hormone or all of these.

In cases where increased levels of growth hormone were desired, the problem was generally solved by providing exogenous growth hormone or by administering an agent which stimulated growth hormone production and/or release. In either case the peptidyl nature of the compound necessitated that it be administered by injection. Initially the source of growth hormone was the extraction of the pituitary glands of cadavers. This resulted in a very expensive product and carried with it the risk that a disease associated with the source of the pituitary gland could be transmitted to the recipient of the growth hormone. Recently, recombinant growth hormone has become available which, while no longer carrying any risk of disease transmission, is still a very expensive product which must be given by injection or by a nasal spray.

Other compounds have been developed which stimulate the release of endogenous growth hormone such as analogous peptidyl compounds related to GRF or the peptides of U.S. Pat. No. 4,411,890. These peptides, while considerably smaller than growth hormones are still susceptible to various proteases. As with most peptides, their potential for oral bioavailability is low. The instant compounds are non-peptidyl agents for promoting the release of growth hormone which may be administered parenterally, nasally or by the oral route.

SUMMARY OF THE INVENTION

The instant invention covers certain benzo-fused lactam compounds which have the ability to stimulate the release of natural or endogenous growth hormone. The compounds thus have the ability to be used to treat conditions which require the stimulation of growth hormone production or secretion such as in humans with a deficiency of natural growth hormone or in animals used for food production where the stimulation of growth hormone will result in a larger, more productive animal. Thus, it is an object of the instant invention to describe the benzo-fused lactam compounds. It is a further object of this invention to describe procedures of the preparation of such compounds. A still further object is to describe the use of such compounds to increase the secretion of growth hormone in humans and animals. A still further object of this invention is to describe compositions containing the benzo-fused lactam compounds for the use of treating humans and animals so as to increase the level of growth hormone secretions. Further objects will become apparent from a reading of the following description.

DESCRIPTION OF THE INVENTION

The novel benzo-fused lactams of the instant invention are best described in the following structural formula I:

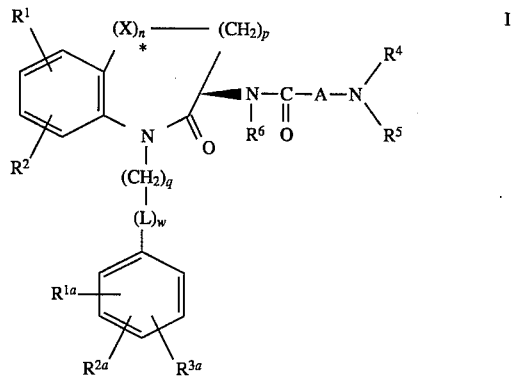

where L is

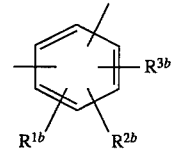

n is 0 or 1;
p is 0 to 3;
q is 0 to 4;
w is 0 or 1;
X is C=O, O, S(O)$_m$,

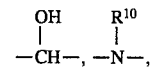

—CH=CH—;
m is 0 to 2;
$R^1$, $R^2$, $R^{1a}$, $R^{2a}$, $R^{1b}$, and $R^{2b}$ are independently hydrogen, halogen, $C_1$–$C_7$ alkyl, $C_1$–$C_3$ perfluoroalkyl, hydrogen, halogen, $C_1$–$C_7$ alkyl, $C_1$–$C_3$ perfluoroalkyl, $R^{7b}O(CH_2)_v$—, $R^{7b}COO(CH_2)_v$—, $R^{7b}OCO(CH_2)_v$—, $R^4R^5N(CH_2)_v$—, $R^{7b}CON(R^4)(CH_2)_v$—, $R^4R^5NCO(CH_2)_v$—, phenyl or substituted phenyl where the substituents are from 1 to 3 or halogen, $C_1$–$C_6$ alkyl, $C_1$–$C_6$ alkoxy, or hydroxy; $R^{7a}$ and $R^{7b}$ are independently hydrogen, $C_1$–$C_3$ perfluoroalkyl, $C_1$–$C_6$ alkyl, substituted $C_1$–$C_6$ alkyl, whee the substituents are phenyl or substituted phenyl; phenyl or substituted phenyl where the phenyl substituents are from 1 to 3 of halogen, $C_1$–$C_6$ alkyl, $C_1$–$C_6$ alkoxy, or hydroxy and v is 0 to 3;

$R^{3a}$ and $R^{3b}$ are independently hydrogen or E–$R^9$, with the proviso that either $R^{3a}$ or $R^{3b}$ must be other than hydrogen;

E is —$(CH_2)_v$—;
—$(CH_2)_v N(R^{10})$—,
—$(CH_2)_v N(R^{10})CO(CH_2)_y$—,
—$(CH_2)_v N(R^{10})COO(CH_2)_y$—,
—$(CH_2)_v N(R^{10})CON(R^{11})(CH_2)_y$—,
—$(CH_2)_v N(R^{10})CSN(R^{11})(CH_2)_y$—,
—$(CH_2)_v OC(O)(CH_2)_y$—,
—$(CH_2)_v OCON(R^{10})(CH_2)_y$—, and v and y are independently 0 to 3;

$R^9$ is:

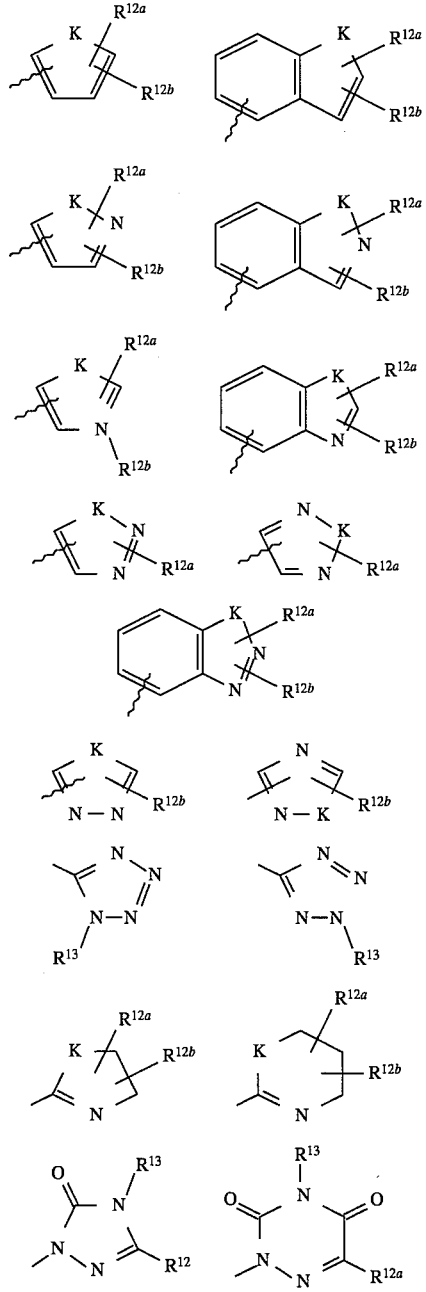

where K is O, S, or $NR^{13}$ and provided that when $R^9$ is a tetrazole, E is other than —$(CH_2)_v$, $R^4$ and $R^5$ are independently hydrogen, phenyl, substituted phenyl, $C_1$–$C_{10}$ alkyl, substituted $C_1$–$C_{10}$ alkyl, $C_3$–$C_{10}$ alkenyl, substituted $C_3$–$C_{10}$ alkenyl, $C_3$–$C_{10}$ alkynyl, or substituted $C_3$–$C_{10}$ alkynyl where the substituents on the phenyl, alkyl, alkenyl or alkynyl are from 1 to 5 of hydroxy, $C_1$–$C_6$ alkoxy, $C_3$–$C_7$ cycloalkyl, fluoro, $R^1$, $R^2$ independently disubstituted phenyl $C_1$–$C_3$ alkoxy, $R^1$, $R^2$ independently disubstituted phenyl, $C_1$–$C_{20}$-alkanoyloxy, $C_1$–$C_5$ alkoxycarbonyl, carboxy, formyl, or —$NR^{10}R^{11}$ where $R^{10}$ and $R^{11}$ are independently hydrogen, $C_1$–$C_6$ alkyl, phenyl, phenyl $C_1$–$C_6$ alkyl, $C_1$–$C_5$-alkoxycarbonyl, or $C_1$–$C_5$-alkanoyl- $C_1$–$C_6$ alkyl; or $R^4$ and $R^5$ can be taken together to form —$(CH_2)_r B(CH_2)_s$— where B is $CHR^1$, O, $S(O)_m$ or N-$R^{10}$, r and s are independently 1 to 3 and $R^1$ and $R^{10}$ are as defined above;

$R^{12a}$ and $R^{12b}$ are independently hydrogen, hydroxy, halogen, oxo, cyano, nitro, —$S(O)_m R^{7a}$, $C_1$–$C_3$ perfluoroalkyl, $C_1$–$C_3$ perfluoroalkoxy, $R^4 R^4 N(CH_2)_v$—, $R^{7b}CON(R^4)$ $(CH_2)_v$—, $R^4 R^5 NCO(CH_2)_v$—, $C_1$–$C_6$ alkoxy, phenyl, substituted phenyl, $C_1$–$C_{10}$ alkyl, substituted $C_1$–$C_{10}$ alkyl, where the substituents on the phenyl or alkyl are from 1 to 5 of hydroxy, $C_1$–$C_6$ alkoxy, $C_3$–$C_7$ cycloalkyl, fluoro, $R^1$, $R^2$ independently disubstituted phenyl $C_1$–$C_3$ alkoxy, $R^1$, $R^2$ independently disubstituted phenyl, $C_1$–$C_6$ alkanoyloxy, $C_1$–$C_5$ alkoxycarbonyl, carboxy, formyl, or —$NR^{10}R^{11}$, where $R^1$, $R^2$, $R^4$, $R^5$, $R^{7a}$, $R^{7b}$, $R^{10}$ and $R^{11}$ are as defined above;

$R^{13}$ is hydrogen, $C_1$–$C_6$ alkyl, substituted $C_1$–$C_6$ alkyl, where the substituents are from 1 to 3 of hydroxy, $C_1$–$C_6$ alkoxy, fluoro, $R^1$, $R^2$ independently disubstituted phenyl $C_1$–$C_3$ alkoxy, $R^1$, $R^2$ independently disubstituted phenyl, $C_1$–$C_6$ alkanoyloxy, $C_1$–$C_5$ alkoxycarbonyl, carboxy, —$NR^{10}R^{11}$, where $R^1$, $R^2$, $R^{10}$ and $R^{11}$ are as defined above, $R^1$, $R^2$ independently disubstituted phenyl or $C_1$–$C_5$ alkanoyl-$C_1$–$C_6$ alkyl;

$R^6$ is hydrogen, $C_1$–$C_{10}$ alkyl, phenyl or phenyl $C_1$–$C_{10}$ alkyl;

A is

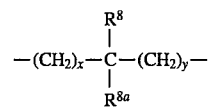

where x and y are independently 0–3;

$R^8$ and $R^{8a}$ are independently hydrogen, $C_1$–$C_{10}$ alkyl, trifluoromethyl, phenyl, substituted $C_1$–$C_{10}$ alkyl where the substituents are from 1 to 3 of imidazolyl, indolyl, hydroxy, fluoro, $S(O)_m R^{7a}$, $C_1$–$C_6$ alkoxy, $C_3$–$C_7$ cycloalkyl, $R^1$, $R^2$ independently disubstituted phenyl $C_1$–$C_3$ alkoxy, $R^1$, $R^2$ independently disbustituted phenyl, $C_1$–$C_5$-alkanoyloxy, $C_1$–$C_5$ alkoxycarbonyl, carboxy, formyl, or —$NR^{10}R^{11}$ where $R^{10}$ and $R^{11}$ are as defined above; or $R^8$ and $R^{8a}$ can be taken together to form —$(CH_2)_t$— where t is 2 to 6; and $R^8$ and $R^{8a}$ can independently be joined to one or both of $R^4$ and $R^5$ to form alkylene bridges between the terminal nitrogen and the alkyl portion of the A group wherein the bridge contains from 1 to 5 carbon atoms; and pharmaceutically acceptable salts thereof.

In the above structural formula and throughout the instant specification, the following terms have the indicated meanings:

The alkyl groups specified above are intended to include those alkyl groups of the designated length in either a straight or branched configuration. Exemplary of such alkyl groups are methyl, ethyl, propyl, isopropyl, butyl, sec-butyl, tertiary butyl, phenyl, isopentyl, hexyl, isohexyl, and the like.

The alkoxy groups specified above are intended to include those alkoxy groups of the designated length in either a straight or branched configuration. Exemplary of such alkoxy groups are methoxy, ethoxy, propoxy, isopropoxy, butoxy, isobutoxy, tertiary butoxy, pentoxy, isopentoxy, hexoxy, isohexoxy and the like.

The term "halogen" is intended to include the halogen atom fluorine, chlorine, bromine and iodine.

Certain of the above defined terms may occur more than once in the above formula and upon such occurrence each term shall be defined independently of the other.

It is intended that the connecting group E can be bonded to any of the available carbon or heteroatoms of the heteroaromatic groups of $R^9$, including both rings of the benzo-fused heterocyclic groups, when the bonding is represented by a serpentine line.

In addition, it is well known to those skilled in the art that many of the foregoing heterocyclic groups can exist in more than one tautomeric form. It is intended that all such tautomers be included within the ambit of this invention.

Preferred compounds of the instant invention are realized when in the above structural formula:

n is 0 or 1;

p is 0 to 3;

q is 0 to 2;

w is 0 or 1;

X is O, $S(O)_m$,

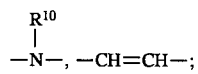

m is 0 to 2;

$R^1$, $R^2$, $R^{1a}$, $R^{2a}$, $R^{1b}$, and $R^{2b}$ are independently hydrogen, halogen, $C_1$-$C_7$ alkyl, $C_1$-$C_3$ perfluoroalkyl, $-S(O)_m R^{7a}$, $R^{7b}O(CH_2)_v-$, $R^{7b}COO(CH_2)_v-$, $R^{7b}OCO(CH_2)_v-$, phenyl or substituted phenyl where the substituents are from 1 to 3 of halogen, $C_1$-$C_6$ alkyl, $C_1$-$C_6$ alkoxy, or hydroxy;

$R^{7a}$ and $R^{7b}$ are independently hydrogen, $C_1$-$C_3$ perfluoroalkyl, $C_1$-$C_6$ alkyl, substituted $C_1$-$C_6$ alkyl, where the substituents are phenyl; phenyl and v is 0 to 2;

$R^{3a}$ and $R^{3b}$ are as defined above;

$R^4$ and $R^5$ are independently hydrogen, phenyl, substituted phenyl, $C_1$-$C_{10}$ alkyl, substituted $C_1$-$C_{10}$ alkyl, where the substituents on the alkyl or phenyl are from 1 to 5 of hydroxy, $C_1$-$C_6$ alkoxy, $C_3$-$C_7$ cycloalkyl, fluoro, $R^1$, $R^2$ independently disubstituted phenyl $C_1$-$C_3$ alkoxy, $R^1$, $R^2$ independently disubstituted phenyl, $C_1$-$C_{20}$-alkanoyloxy, $C_1$-$C_5$ alkoxycarbonyl, carboxy or formyl;

$R^4$ and $R^5$ can be taken together to form $-(CH_2)_rB(CH_2)_s-$ where B is $CHR^1$, O, $S(O)_m$ or $N-R^{10}$; r and s are independently 1 to 3 and $R^1$ and $R^{10}$ are as defined above;

$R^6$ is hydrogen, $C_1$-$C_{10}$ alkyl or phenyl $C_1$-$C_{10}$ alkyl;

A is

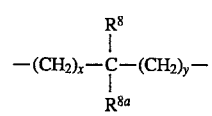

where x and y are independently 0–2;

$R^8$ and $R^{8a}$ are independently hydrogen, $C_1$-$C_{10}$ alkyl, substituted $C_1$-$C_{10}$ alkyl where the substituents are from 1 to 3 of imidazolyl, indolyl, hydroxy, fluoro, $S(O)_m R^{7a}$, $C_1$-$C_6$ alkoxy, $R^1$, $R^2$ independently disubstituted phenyl, $C_1$-$C_5$-alkanoyloxy, $C_1$-$C_5$ alkoxycarbonyl, carboxy, formyl, $-NR^{10}R^{11}$ where $R^{10}$ and $R^{11}$ are independently hydrogen, $C_1$-$C_6$ alkyl or $C_1$-$C_5$ alkanoyl-$C_1$-$C_6$ alkyl; or $R^8$ and $R^{8a}$ can be taken together to form $-(CH_2)_t-$ where t is 2 to 4; and $R^8$ and $R^{8a}$ can independently be joined to one or both of $R^4$ and $R^5$ to form alkylene bridges between the terminal nitrogen and the alkyl portion of the A group wherein the bridge contains from 1 to 5 carbon atoms; and pharmaceutically acceptable salts thereof.

Additional preferred compounds are realized in the above structural formula when:

n is 0 or 1;

p is 0 to 2;

q is 0 to 2;

w is 0 or 1;

X is $S(O)_m$ or $-CH=CH-$;

m is 0 or 1;

$R^1$, $R^2$, $R^{1a}$, $R^{2a}$, $R^{1b}$, and $R^{2b}$ are independently hydrogen, halogen, $C_1$-$C_7$ alkyl, $C_1$-$C_3$ perfluoroalkyl, $-S(O)_m R^{7a}$, $R^{7b}O(CH_2)_v-$, $R^{7b}COO(CH_2)_v-$, $R^{7b}OCO(CH_2)_v-$, phenyl or substituted phenyl where the substituents are from 1 to 3 or halogen, $C_1$-$C_6$ alkyl, $C_1$-$C_6$ alkoxy or hydroxy;

$R^{7a}$ and $R^{7b}$ are independently hydrogen, $C_1$-$C_6$ alkyl, substituted $C_1$-$C_6$ alkyl, where the substituents are phenyl and v is 0 to 2;

$R^{3a}$ and $R^{3b}$ are as defined above;

$R^4$ and $R^5$ are independently hydrogen, $C_1$-$C_{10}$ alkyl, substituted $C_1$-$C_{10}$ alkyl, where the substituents on the alkyl are from 1 to 5 of hydroxy, $C_1$-$C_6$ alkoxy, fluoro, $R^1$, $R^2$ independently disubstituted phenyl, $C_1$-$C_{20}$-alkanoyloxy, $C_1$-$C_5$ alkoxycarbonyl or carboxy;

$R^6$ is hydrogen or $C_1$-$C_{10}$ alkyl;

A is

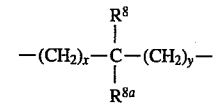

where x and y are independently 0–2;

$R^8$ and $R^{8a}$ are independently hydrogen, $C_1$-$C_{10}$ alkyl, substituted $C_1$-$C_{10}$ alkyl where the substituents are from 1 to 3 or imidazolyl, indolyl, hydroxy, fluoro, $S(O)_m R^{7a}$, $C_1$-$C_6$ alkoxy, $R^1$, $R^2$ independently disubstituted phenyl, $C_1$-$C_5$-alkanoyloxy, $C_1$-$C_5$ alkoxycarbonyl, carboxy; or $R^8$ and $R^{8a}$ can be taken together to form $-(CH_2)_t-$ where t is 2; or $R^8$ and $R^{8a}$ can independently be joined to one or both of $R^4$ and $R^5$ to form alkylene bridges between the terminal nitrogen and the alkyl portion of the A group wherein the bridge contains from 1 to 5 carbon atoms; and pharmaceutically acceptable salts thereof.

Still further preferred compounds of the instant invention are realized in the above structural formula when;

n is 0 or 1;

p is 0 to 2;

q is 1;

w is 1;

X is $S(O)_m$ or $-CH=CH-$;

m is 0 or 1;

$R^1$, $R^2$, $R^{1a}$, $R^{2a}$, $R^{1b}$, and $R^{2b}$ are independently hydrogen, halogen, $C_1$–$C_7$ alkyl, $C_1$–$C_3$ perfluoroalkyl, —S(O)$_m R^{7a}$, $R^{7b}$O(CH$_2$)$_v$—, $R^{7b}$COO(CH$_2$)$_v$—, phenyl or substituted phenyl where the substituents are from 1 to 3 of halogen, $C_1$–$C_6$ alkyl, $C_1$–$C_6$ alkoxy, or hydroxy;

$R^{7a}$ and $R^{7b}$ are independently hydrogen, $C_1$–$C_6$ alkyl, substituted $C_1$–$C_6$ alkyl, where the substituents are phenyl, and v is 0 or 1;

$R^{3a}$ and $R^{3b}$ are as defined above.

$R^4$ and $R^5$ are independently hydrogen, $C_1$–$C_{10}$ alkyl, substituted $C_1$–$C_{10}$ alkyl, where the substituents on the alkyl are from 1 to 3 of hydroxy, $C_1$–$C_3$ alkoxy, fluoro, $R^1$, $R^2$ independently disubstituted phenyl, $C_1$–$C_{20}$ alkanoyloxy, $C_1$–$C_5$ alkoxycarbonyl or carboxy;

$R^6$ is hydrogen;

A is

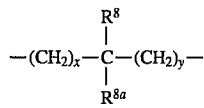

where x and y are independently 0–1;

$R^8$ and $R^{8a}$ are independently hydrogen, $C_1$–$C_{10}$ alkyl, substituted $C_1$–$C_{10}$ alkyl where the substituents are from 1 to 3 of imidazolyl, indolyl, hydroxy, fluoro, S(O)$_m R^{7a}$, $C_1$–$C_6$ alkoxy, $R^1$, $R^2$ independently disubstituted phenyl, $C_1$–$C_5$-alkanoyloxy, $C_1$–$C_5$ alkoxycarbonyl, carboxy; or $R^8$ and $R^{8a}$ can be taken together to form —(CH$_2$)$_t$— where t is 2; and $R^8$ and $R^{8a}$ can independently be joined to one or both of $R^4$ and $R^5$ to form alkylene bridges between the terminal nitrogen and the alkyl portion of the A group wherein the bridge contains from 1 to 5 carbon atoms; and pharmaceutically acceptable salts thereof.

Representative preferred growth hormone releasing compounds of the present invention include the following:

1. 3-[2(S),3-Dihydroxypropyl)amino-3-methyl-N-[2,3,4,5-tetrahydro-2-oxo-1-[[2'-(1H-imidazol-2-yl)[1,1'-biphenyl]-4-yl]methyl]-1H-1-benzazepin-3(R)-yl]-butanamide
2. 3-[(2R)-Hydroxypropyl)amino]-3-methyl-N-[2,3,4,5-tetrahydro-2-oxo-1-[[2'-(1H-imidazol-4-yl)[1,1'-biphenyl]-4-yl]methyl]-1H-1-benzazepin-3(R)-yl]-butanamide
3. 3-[2(S),3-Dihydroxypropyl]amino-3-methyl-N-([2,3,4,5-tetrahydro-2-oxo-1-[[2'-(1H-imidazol-4-yl)(1,1'-biphenyl]-4-yl]methyl]-1H-1-benzazepin-3(R)-yl]-butanamide
4. 3-[(2R)-Hydroxypropyl)amino]-3-methyl-N-[2,3,4,5-tetrahydro-2-oxo-1-[[2'-(1H-1,2,3-triazol-4yl)[1,1'-biphenyl]-4-yl]methyl]-1H-1-benzazepin-3(R)-yl]-butanamide
5. 3-[2(S),3-Dihydroxypropyl]amino-3-methyl-N-[2,3,4,5-tetrahydro-2-oxo-1-[[2'-(1H-1,2,3-triazol-4-yl)-[1,1'-biphenyl]-4-yl]methyl]-1H-1-benzazepin-3(R)-yl]-butanamide
6. 3-[(2R)-Hydroxypropyl)amino)-3-methyl-N-[2,3,4,5-tetrahydro-2-oxo-1-[[2'-(1H-1,2,4-triazol-3-yl)[1,1'-biphenyl]-4-yl]methyl]-1H-1-benzazepin-3(R)-yl]-butanamide
7. 3-[2(S),3-Dihydroxypropyl)amino-3-methyl-N-[2,3,4,5-tetrahydro-2-oxo-1-[[2'-(1H-1,2,4-triazol-3-yl)-[1,1'-biphenyl]-4-yl]methyl]-1H-1-benzazepin-3(R)-yl]-butanamide
8. 3-[(2R)-Hydroxypropyl)amino]-3-methyl-N-[2,3,4,5-tetrahydro-2-oxo-1-[[2'-[(4,5-dihydro-2-oxazolyl)-amino][1,1'-biphenyl]-4-yl]methyl]-1H-1-benzazepin-3(R)-yl]-butanamide
9. 3-[2(S),3-Dihydroxypropyl]amino-3-methyl-N-[2,3,4,5-tetrahydro-2-oxo-1-[[2'-[(4,5-dihydro-2-oxazolyl)amino][1,1'-biphenyl]-4-yl]methyl]-1H-1-benzazepin-3(R)-yl]-butanamide
10. 3-[2(R)-Hydroxypropyl]amino-3-methyl-N-[2,3,4,5-tetrahydro-2-oxo-1-[[2'-[[(1H-imidazol-4-yl)-acetamido]methyl][1,1'-biphenyl]-4-yl]methyl]-1H-1-benzazepin-3(R)-yl]-butanamide
11. 3-[2(S),3-Dihydroxypropyl]amino-3-methyl-N-[2,3,4,5-tetrahydro-2-oxo-1-[[2'-[[(1H-imidazol-4-yl)acetamido]methyl][1,1'-biphenyl]-4-yl]-methyl]-1H-1-benzazepin-3(R)-yl]-butanamide
12. 3-Amino-3-methyl-N-[2,3,4,5-tetrahydro-2-oxo-1-[[2'-[(4,5-dihydro-1H-imidazol-2-yl)amino][1,1'-biphenyl]-4-yl]methyl]-1H-1-benzazepin-3(R)-yl]-butanamide
13. 3-[(2(R)-Hydroxypropyl)amino]-3-methyl-N-[2,3,4,5-tetrahydro-2-oxo-1-[[2'-[4,5-dihydro-1H-imidazol-2-yl)amino][1,1'-biphenyl]-4-yl]methyl]-1H-1-benzazepin-3(R)-yl]-butanamide
14. 3-[2(S),3-Dihydroxypropyl]amino-3-methyl-N-[2,3,4,5-tetrahydro-2-oxo-1-[[2'-[(4,5-dihydro-1H-imidazoyl-2-yl)amino][1,1'-biphenyl]-4-yl]-methyl]-1H-1-benzazepin-3(R)-yl]-butanamide
15. 3-Amino-3-methyl-N-[2,3,4,5-tetrahydro-2-oxo-1-[[2'-[(1H-imidazol-2-yl)amino][1,1'-biphenyl]-4-yl]methyl]-1H-1-benzazepin-3(R)-yl]butanamide
16. 3-[(2(R)-Hydroxypropyl)amino]-3-methyl-N-[2,3,4,5-tetrahydro-2-oxo-1-[[2'-[(1H-imidazol-2-yl)amino]-[1,1'-biphenyl]-4-yl]methyl]-1H-1-benzazepin-3(R)-yl]-butanamide
17. 3-[2(S),3-Dihydroxypropyl]amino-3-methyl-N-[2,3,4,5-tetrahydro-2-oxo-1-[[2'-[(1H-imidazol-2-yl amino][1,1'-biphenyl]-4-yl]methyl]-1H-1-benzazepin-3(R)-yl]-butanamide
18. 3-Amino-3-methyl-N-[2,3,4,5-tetrahydro-2-oxo-1-[[2'-[(1H-tetrazol-5-yl)amino][1,1'-biphenyl]-4-yl]methyl]-1H-1-benzazepin-3(R)-yl]-butanamide
19. 3-[(2(R)-Hydroxypropyl)amino]-3-methyl-N-[2,3,4,5-tetrahydro-2-oxo-1-[[2'-[(1H-tetrazol-5-yl)amino][1,1'-biphenyl]-4-yl]methyl]-1H-1-benzazepin-3(R)-yl]-butanamide
20. 3-[2(S), 3-Dihydroxypropyl]amino-3-methyl-N-[2,3,4,5-tetrahydro-2-oxo-1-[[2'-[(1H-tetrazol-5-yl)amino][1,1'-biphenyl]-4-yl]methyl]-1H-1-benzazepin-3(R)-yl]-butanamide
21. 3-Amino-3-methyl-N-[2,3,4,5-tetrahydro-2-oxo-1-[[2'-(4,5-dihydro-5-oxo-1H-1,2,4-triazol-1-yl)-[1,1'-biphenyl]-4-yl]methyl]-1H-1-benzazepin-3(R)-yl]-butanamide
22. 3-[(2(R)-Hydroxypropyl)amino]-3-methyl-N-[2,3,4,5-tetrahydro-2-oxo-1-[[2'-(4,5-dihydro-5-oxo-1H-1,2,4-triazol-1-yl)[1,1'-biphenyl]-4-yl]methyl]-1H-1-benzazepin-3(R)-yl]-butamide
23. 3-[2(S),3-Dihydroxypropyl]amino-3-methyl-N-[2,3,4,5-tetrahydro-2-oxo-1-[[2'-(4,5-dihydro-5-oxo-1H-1,2,4-triazol-1-yl)[1,1'-biphenyl]-4-yl]methyl]-1H-1-benzazepin-3(R)-yl]-butanamide
24. 3-Amino-3-methyl-N-[2,3,4,5-tetrahydro-2-oxo-1-[[2'-(4,5-dihydro-3,5-dioxo-1,2,4-triazin-2(3H)-yl[1,1'-biphenyl]-4-yl]methyl]-1H-1-benzazepin-3(R)-yl]-butanamide
25. 3-[(2(R)-Hydroxypropyl)amino]-3-methyl-N-[2,3,4,5-tetrahydro-2-oxo-1-[[2'-(4,5-dihydro-3,5-dioxo-1,2,4-triazin-2(3H)-yl)[1,1'-bipenyl]-4-yl]methyl]-1H-1-benzazepin-3(R)-yl]-butanamide
26 3-[2(S),3-Dihydroxypropyl]amino-3-methyl-N-[2,3,4,5-tetrahydro-2-oxo-1-[2'-[(4,5-dihydro-3,5-dioxo-1,2,4-triazin-2(3H)-yl)[1,1'-biphenyl]-4-yl]methyl]-1H-1-benzazepin-3(R)-yl]-butanamide 27. 2-Amino-2-methyl-N-[2,3,4,5-tetrahydro-2-oxo-1-[[2'-(1H-imidazol-2-yl)[1,1'-biphenyl]-4-yl]methyl]-1H-1-benzazepin-3(R)-yl]-propanamide
28. 2-Amino-2-methyl-N-[2,3,4,5-tetrahydro-2-oxo-1-[[2'-(1H-imidazol-4-yl)[1,1'-biphenyl]-4-yl]methyl]-1H-1-benzazepin-3(R)-yl]-propanamide
29. 2-Amino-2-methyl-N-[2,3,4,5-tetrahydro-2-oxo-1-[[2'-(1H-1,2,3-triazol-4-yl)[1,1'-biphenyl]-4-yl]methyl]-1H-1-benzazepin-3(R)-yl]-propanamide
30. 2-Amino-2-methyl-N-[2,3,4,5-tetrahydro-2-oxo-1-[[2'-(1H-1,2,4-triazol-3-yl)[1,1'-biphenyl]-4-yl]methyl]-1H-1-benzazepin-3(R)-yl]-propanamide
31. 2-Amino-2-methyl-N-[2,3,4,5-tetrahydro-2-oxo-1-[[2'-[(4,5-dihydro-2-oxazolyl)amino][1,1'-biphenyl]-4-yl]methyl]-1H-1-benzazepin-3(R)-yl]-propanamide
32. 2-Amino-2-methyl-N-[2,3,4,5-tetrahydro-2-oxo-1-[[2'-[[(1H-imidazol-4-yl)acetamido]methyl][1,1'-biphenyl]-4-yl]methyl]-1H-1-benzazepin-3(R)-yl]-propanamide
33. 2-Amino-2-methyl-N-[2,3,4,5-tetrahydro-2-oxo-1-[[2'-(4,5-dihydro-3,5-dioxo-1,2,4-triazin-2-(3H)-yl)[1,1'-biphenyl]-4-yl]methyl]-1H-1-benzazepin-3(R)-yl]-propanamide
34. 2-Amino-2-methyl-N-[2,3,4,5-tetrahydro-2-oxo-1-[[2'-(4,5-dihydro-5-oxo-1H-1,2,4-triazol-1-yl)[1,1'-biphenyl]-4-yl]methyl]-1H-1-benzazepin-3(R)-yl]-propanamide
35. 2-Amino-2-methyl-N-[2,3,4,5-tetrahydro-2-oxo-1-[[2'-[(1H-imidazol-2-yl)amino][1,1'-biphenyl]-4-yl]methyl]-1H-1-benzazepin-3(R)-yl]-propanamide
36. 2-Amino-2-methyl-N-[2,3,4,5-tetrahydro-2-oxo-1-[[2'-[(1H-tetrazol-5-yl)amino][1,1'-biphenyl]-4-yl]methyl]-1H-1-benzazepin-3(R)-yl]-propanamide
37. 2-Amino-2-methyl-N-[2,3,4,5-tetrahydro-2-oxo-1-[[2'-[(4,5-dihydro-1H-imidazol-2-yl)amino][1,1'-biphenyl]-4-yl]methyl]-1H-1-benzazepin-3(R)-yl]-propanamide
38. 3-Amino-3-methyl-N-[7-trifluoromethyl-2,3,4,5-tetrahydro-2-oxo-1-[[2'-(1H-imidazol-2-yl)[1,1'-biphenyl]-4-yl]methyl]-1H-1-benzazepin-3(R)-yl]-butanamide
39. 3-Amino-3-methyl-N-[7-trifluoromethyl-2,3,4,5-tetrahydro-2-oxo-1-[[2'-(1H-imidazol-4-yl)[1,1'-biphenyl]-4-yl]methyl]-1H-1-benzazepin-3(R)-yl]-butanamide
40. 3-Amino-3-methyl-N-[7-trifluoromethyl-2,3,4,5-tetrahydro-2-oxo-1-[[2'-(1H-1,2,3-triazol-4-yl)[1,1'-biphenyl]-4-yl]methyl]-1H-1-benzazepin-3(R)-yl]-butanamide
41. 3-Amino-3-methyl-N-[7-fluoro-2,3,4,5-tetrahydro-2-oxo-1-[[2'-(1H-1,2,4-triazol-3-yl)[1,1'-biphenyl]-4-yl]methyl]-1H-1-benzazepin-3(R)-outanamide
42. 3-Amino-3-methyl-N-[7-fluoro-2,3,4,5-tetrahydro-2-oxo-1-[[2'-[(4,5-dihydro-2-oxazolyl)amino][1,1'-biphenyl]-4-yl]methyl]-1H-1-benzazepin-3(R)-yl]-butanamide
43. 3-Amino-3-methyl-N-[7-fluoro-2,3,4-tetrahydro-2-oxo-1-[[2'-(1H-imidazol-4-yl)acetamido]methyl][1,1'-biphenyl]-4-yl]methyl]-1H-1-benzazepin-3(R)-yl]-butanamide
44. 3-[2(S), 3-Dihydroxypropyl]amino-3-methyl-N-[7-fluoro-2,3,4,5-tetrahydro-2-oxo-1-[[2'-(1H-imidazol-2-yl)[1,1'-biphenyl]-4-yl]methyl]-1H-1-benzazepin-3(R)-yl]-butanamide
45. 3-[(2(R)-Hydroxypropyl)amino]-3-methyl-N-[7-trifluoromethyl-2,3,4,5-tetrahydro-2-oxo-1-[[2'-(1H-imidazol-4-yl)[1,1'-biphenyl]-4-yl]methyl]-1H-1-benzazepin-3(R)-yl]-butanamide
46. 3-[(2(R)-Hydroxypropyl)amino]-3-methyl-N-[7-fluoro-2,3,4,5-tetrahydro-2-oxo-1-[[2'-(1H-1,2,3-triazol-4-yl)[1,1'-biphenyl]-4-yl]methyl]-1H-1-benzazepin-3(R)-yl]-butanamide
47. 3-[2(S),3-Dihydroxypropyl]amino-3-methyl-N-[7-fluoro-2,3,4,5-tetrahydro-2-oxo-1-[[2'-(1H-1,2,3-triazol-4-yl)[1,1'-biphenyl]-4-yl]methyl]-1H-1-benzazepin-3(R)-yl]-butanamide
48. 3-[(2(R)-Hydroxypropyl)amino]-3-methyl-N-[7-trifluoromethyl-1,2,3,4,5-tetrahydro-2-oxo-1-[[2'-(1H-1,2,4-triazol-3-yl)[1,1'-biphenyl]-4-yl]methyl]-1H-1-benzazepin-3(R)-yl]-butanamide
49. 3-[2(R)-Hydroxypropyl)amino]-3-methyl-N-[7-fluoro-2,3,4,5-tetrahydro-2-oxo-1-[[2'-[(4,5-dihydro-2-oxazolyl)amino][1,1'-biphenyl]-4-yl]methyl]-1H-1-benzazepin-3(R)-yl]-butanamide
50. 3-[2(S),3-Dihydroxypropyl]amino-3-methyl-N-[7-trifluoromethyl-1,2,3,4,5-tetrahydro-2-oxo-1-[[2-[(4,5-dihydro-2-oxazolyl)amino][1,1'-biphenyl]-4-yl]methyl]-1H-1-benzazepin-3(R)-yl]-butanamide
51. 3-[2(S),3-Dihydroxypropyl]amino-3-methyl-N-[7-trifluoromethyl-2,3,4,5-tetrahydro-2-oxo-1-[[2'-[[(1H-imidazol-4-yl)acetamido]methyl][1,1'-biphenyl]-4-yl]methyl]-1H-1-benzazepin-3-(R)-yl]-butanamide
52. 3-[(2(R)-Hydroxypropyl)amino]-3-methyl-N-[7-fluoro-2,3,4,5-tetrahydro-2-oxo-1-[[2'-[(1H-imidazol-2-yl)amino][1,1'-biphenyl]-4-yl]methyl]-1H-1-benzazepin-3(R)-yl]-butanamide
53. 3-[2(S),3-Dihydroxyproyl]amino-3-methyl-N-[7-fluoro-2,3,4,5-tetrahydro-2-oxo-1-[[2'-(1H-tetrazol-5-yl)amino][1,1'-biphenyl]-4-yl]methyl]-1H-1-benzazepin-3(R)-yl]-butanamide
54. 3-[2(R)-Hydroxypropyl]amino]-3-methyl-N-[7-fluoro-2,3,4,5-tetrahydro-2-oxo-1-[[2'-(4,5-dihydro-5-oxo-1H-1,2,4-triazol-1-yl)[1,1'-biphenyl]-4-yl]methyl]-1H-1-benzazepin-3(R)-yl]-butanamide
55. 3-[2(S), 3-Dihydroxypropyl]amino-3-methyl-N-[7-trifluoromethyl-2,3,4,5-tetrahydro-2-oxo-1-[[2'-(4,5-dihydro-5-oxo-1H-1,2,4-triazol-1-yl)[1,1'-biphenyl]-4-yl]methyl]-1H-1-benzazepin-3(R)-yl]-butanamide
56. 3-[(2(R)-Hydroxypropyl)amino]-3-methyl-N-[7-methoxy-2,3,4,5-tetrahydro-2-oxo-1-[[2'-(4,5-dihydro-3,5-dioxo-1,2,4-triazin-2(3H)-yl)[1,1'-biphenyl]-4-yl]methyl]-1H-1-benzazepin-3(R)-yl]-butanamide
57. 3-Amino-3-methyl-N-[2,3,4,5-tetrahydro-4-oxo-5-[[2'-(1H-imidazol-2-yl)[1,1'-biphenyl]-4-yl]methyl]-1,5-benzothiazepin-3(S)-yl]-butanamide
58. 3-Amino-3-methyl-N-[2,3,4,5-tetrahydro-4-oxo-5-[[2'-(1H-imidazol-4-yl)[1,1'-biphenyl]-4-yl]methyl]-1,5-benzothiazepin-3(S)-yl]-butanamide
59. 3-Amino-3-methyl-N-[2,3,4,5-tetrahydro-4-oxo-5-[[2'-(1H-1,2,3-triazol-4-yl)[1,1'-biphenyl]-4-yl]methyl]-1,5-benzothiazepin-3(S)-yl]-butanamide
60. 3-Amino-3-methyl-N-[2,3,4,5-tetrahydro-4-oxo-5-[[2'-[4,5-dihydro-2-oxazolyl)amino][1,1'-biphenyl]-4-yl]methyl]-1,5-benzothiazepin-3(S)-yl]-butanamide
61. 3-[(2(R)-Hydroxypropyl)amino]-3-methyl-N-[2,3,4,5-tetrahydro-4-oxo-5-[[2'-(1H-imidazol-2-yl)[1,1'-biphenyl]-4-yl]methyl]-1,5-benzothiazepin-3(S)-yl]-butanamide
62. 3-Amino-3-methyl-N-2,3,4,5-tetrahydro-4-oxo-5-[[2'-[[(1H-imidazol-4-yl)acetamido]methyl][1,1'-biphenyl]-4-yl]methyl]-1,5-benzothiazepin-3(S)-yl]-butanamide
63. 3-[2(R)-Hydroxypropyl]amino]-3-methyl-N-[2,3,4,5-tetrahydro-4-oxo-5-[[2'-[[(1H-imidazol-4-yl)acetamido]methyl][[1,1'-biphenyl]-4-yl]methyl]-1,5-benzothiazepin-3(S)-yl]-butanamide
64. 3-[(2(R)-Hydroxypropyl)amino]-3-methyl-N-[2,3,4,5-tetrahydro-4-oxo-5-[[2'-(1H-1,2,3-triazol-4-yl)-[1,1'-biphenyl]-4-yl]methyl]-1,5-benzothiazepin-3(S)-yl]-butanamide
65. 3-[(2(R)-Hydroxypropyl)amino]-3-methyl-N-[2,3,4,5-tetrahydro-4-oxo-5-[[2'-[(4,5-dihydro-2-oxazolyl)amino][1,1'-biphenyl]-4-yl]methyl]-1,5-benzothiazepin-3(S)-yl]-butanamide 66. 3-[2(R)-Hydroxypropyl]amino-3-methyl-N-[7-fluoro-2,3,4,5-tetrahydro-4-oxo-5-[[2'-[[(1H-imidazol-4-yl)-acetamido]methyl][1,1'-biphenyl]-4-yl]methyl]-1,5-benzothiazepin-3(S)-yl]-butanamide
67. 3-[2(S), 3-Dihydroxypropyl]amino-3-methyl-N-[2,3,4,5-tetrahydro-4-oxo-5-[[2'-[[(1H-imidazol-4-yl)acetamido]methyl][1,1'-biphenyl]-4-yl]methyl]-1,5-benzothiazepin-3(S)-yl]-butanamide
68. 2-Amino-2-methyl-N-[2,3,4,5-tetrahydro-4-oxo-5-[[2'-(1H-imidazol-2-yl)[1,1'-biphenyl]-4-yl]methyl]-1,5-benzothiazepin-3(S)-yl]propanamide
69. 2-Amino-2-methyl-N-[2,3,4,5-tetrahydro-4-oxo-5-[[2'-(1H-imidazol-4-yl)[1,1'-biphenyl]-4-yl]methyl]-1,5-benzothiazepin-3(S)-yl]-propanamide
70. 2-Amino-2-methyl-N-[2,3,4,5-tetrahydro-4-oxo-5-[[2'-(1H-1,2,3-triazol-4-yl)[1,1'-biphenyl]-4-yl]methyl]-1,5-benzothiazepin-3(S)-yl]-propanamide
71. 2Amino-2-methyl-N-[2,3,4,5-tetrahydro-4-oxo-5-[[2'-[[(1H-imidazol-4-yl)acetamido]methyl][1,1'-biphenyl]-4-yl]methyl]-1,5-benzothiazepin-3(S)-yl]-propanamide
72. 2-Amino-2-methyl-N-[2,3,4,5-tetrahydro-4-oxo-5-[[2'-[(4,5-dihydro-5-oxo-1H-1,2,4-triazol-1-yl)amino][1,1'-biphenyl]-4-yl]methyl]-1,5-benzothiazepin-3(S)-yl]-propanamide Representative examples of the nomenclature employed are given below:

3-Amino-3-methyl-N-[2,3,4,5-tetrahydro-2-oxo-1-[[2'-(thizaol-2-yl)[1,1'-biphenyl]-4-yl]methyl]-1H-1-benzazepin-3(R)-yl]-butanamide

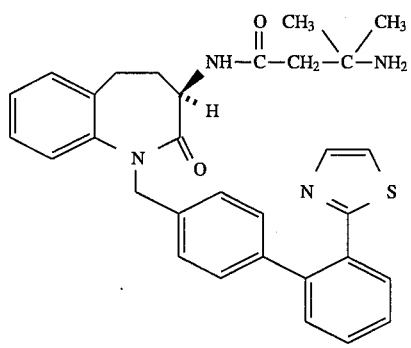

N-[1-[[2'-[[(Thiazol-2-yl)aminocarbonyl]amono][1,1'-biphenyl]-4-yl]methyl]-7-fluoro-2,3,4,5-tetrahydro-2-oxo-1H-1-benzazepin-3(R)-yl]-2-amino-2-methylpropanamide

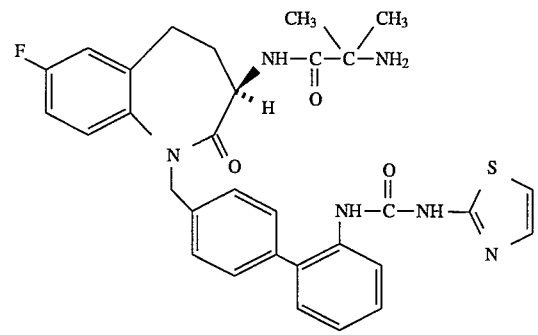

3-[(2(R)-Hydroxypropyl)amino]-3-methyl-N-[2,3,4,5-tetrahydro-2-oxo-1-[[2'-[(4,5-dihydro-2-thiazolyl)amino][1,1'-biphenyl]-4-yl]methyl]-1H-1-benzazepin-3(R)-yl]-butanamide

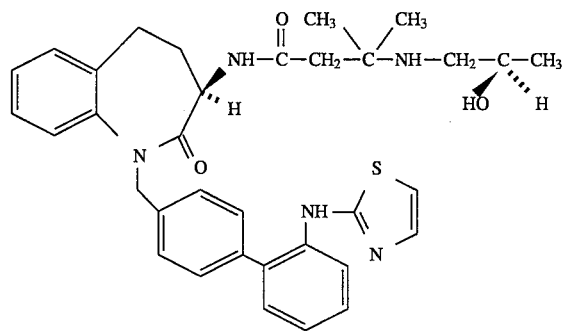

3-[(2(S),3-Dihydroxypropyl)amino]-3-methyl-N-[2,3,4,5-tetrahydro
3-[(2(S),3-Dihydroxypropyl)amino]-3-methyl-N-[2,3,4,5-tetrahydro [1,1'-biphenyl]-4-yl]methyl]-1,5-benzothiazepin-3(S)-yl]-butanamide

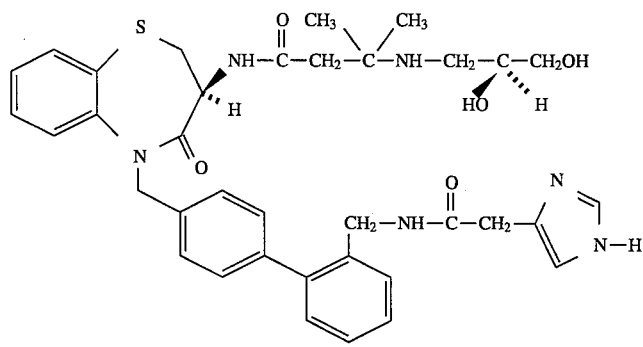

The compounds of the instant invention all have at least one asymmetric center as noted by the asterisk in the structural Formula I above. Additional asymmetric centers may be present on the molecule depending upon the nature of the various substituents on the molecule. Each such asymmetric center will produce two optical isomers and it is intended that all such optical isomers, as separated, pure or partially purified optical isomers or racemic mixtures thereof, be included within the ambit of the instant invention. In the case of the asymmetric center represented by the asterisk in Formula I, it has been found that the compound in which the 3-amino substituent is above the plane of the structure, as seen in Formula Ia, is more active and thus more preferred over the compound in which the 3-amino substituent is below the plane of the structure. In the substituent $(X)_n$, when n=0, the asymmetric center is designated as the R-isomer. When n=1, this center will be designated according to the R/S rules as either R or S depending upon the value of X.

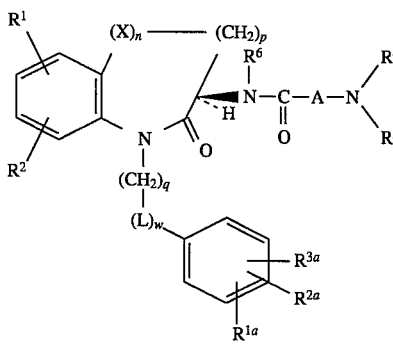

Ia

The instant compounds are generally isolated in the form of their pharmaceutically acceptable acid addition salts, such as the salts derived from using inorganic and organic acids. Examples of such acids are hydrochloric, nitric, sulfuric, phosphoric, formic, acetic, trifluoroaetic, propionic, maleic, succinic, malonic and the like. In addition, certain compounds containing an acidic function such as a carboxy can be isolated in the form of their inorganic salt in which the counterion can be selected from sodium, potassium, lithium, calcium, magnesium and the like, as well as from organic bases.

The compounds (I) of the present invention are prepared from aminolactum intermediates such as those of formula II. The preparation of these intermediates is described in the following reaction Schemes.

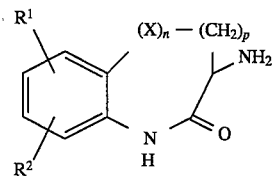

II

Benzo-fused lactams 3 wherein the lactam is a seven-membered ring are conveniently prepared from substituted tetralones 2 using known procedures. The substituted tetralones are, in some cases, commercially available or are prepared from a suitably substituted derivative of 4-phenyl-butyric acid 1. Cyclization of 1 can be achieved by a number of methods well known in the literature including treatment with polyphosphoric acid at elevated temperatures as shown in Scheme 1.

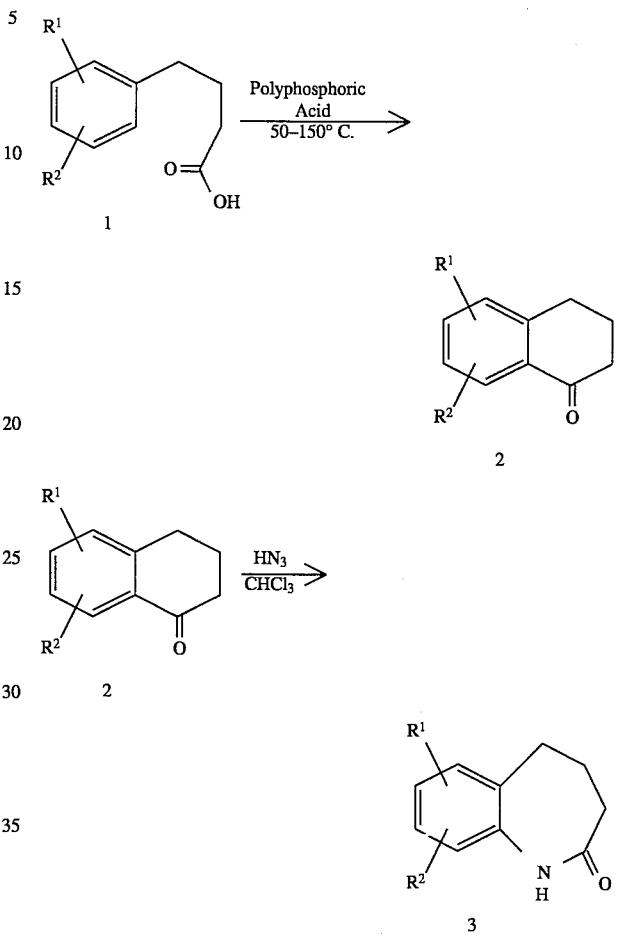

Conversion of substituted tetralones 2 to benzolactams 3 can be achieved by a number of methods familiar to those skilled in the art. A suitable method involves the use of hydrazoic acid (Schmidt reaction) to form the substituted benzolactam 3.

Benzo-fused lactams wherein the lactam is an eight-membered ring (6) are prepared as described by D. E. Jones, et al, J. Chem. Soc. C, 2176–2181 (1969) by an analogous series of transformations starting from a substituted derivative of 5-phenylpentanoic acid 4 as shown in Scheme 2.

SCHEME 2

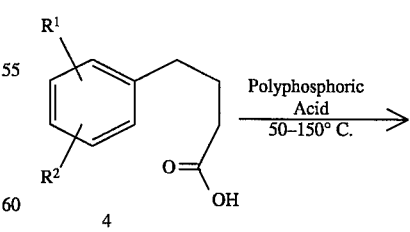

-continued
SCHEME 2

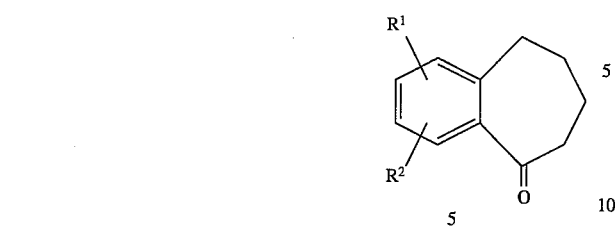

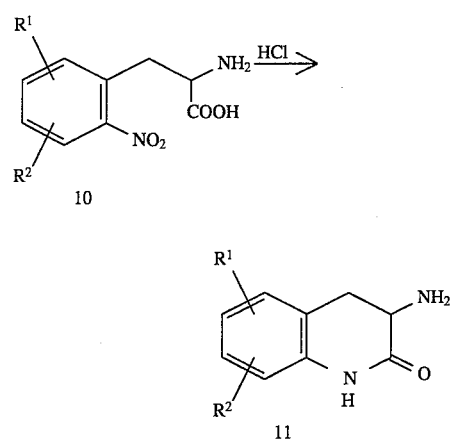

As shown in Scheme 3, 3-aminobenzolactam analogs wherein the lactam is a six-membered ring (11) are prepared from a substituted derivative of 2-nitrobenzyl chloride (or bromide) 7 by the method of A. L. David, et al, Arch. Biochem. Biophys, 102, 48–51 (1963) and reference cited therein.

-continued
SCHEME 3

Conversion of substituted benzo-fused lactams to the requisite 3-amino derivatives can be achieved by a number of methods familiar to those skilled in the art, including those described by Watthey, et al, J. Med. Chem., 28, 1511–1516 (1985) and reference cited therein. One common route proceeds via the intermediacy of a 3-halo (chloro. bromo or iodo) intermediate which is subsequently displaced by a nitrogen nucleophils, typically azide. A useful method of forming the 3-iodobenzolactam intermediate 12 involves treating the benzolactam with two equivalents each of iodotrimethylisilane and iodine at low temperature, as illustrated in Scheme 4 for the seven-membered ring analog 3.

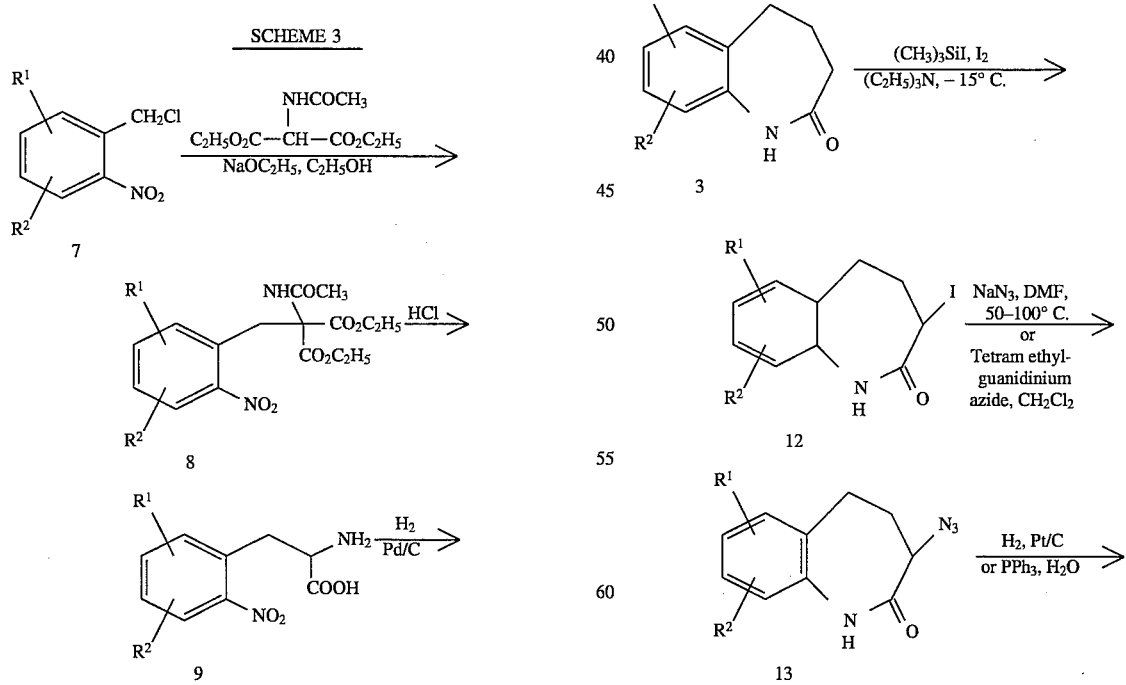

-continued
SCHEME 4

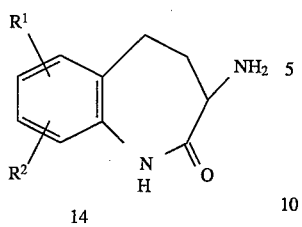

14

Elaboration of the iodo-benzolactams to the desired aminolactam intermediates II is achieved by a two-step procedure illustrated in Scheme 4. Typically, iodo-benzolactams 12 are treated with sodium azide in N,N-dimethylformamide at 50°–100° C. to give the 3-azido derivatives 13. Alternatively, tetramethylguanidinium azide in a solvent such as methylene chloride can be employed to achieve similar results. Hydrogenation with a metal catalyst, such as platinum on carbon, or alternatively, treatment with triphenylphosphine in wet toluene, results in formation of the amine derivative 14. Formation of the analogous derivatives of the eight-membered benzolactams is also achieved by the routes shown in Scheme 4.

Chiral aminobenzolactams are obtained by resolution of the racemates by classical methods familiar to those skilled in the art. For example, resolution can be achieved by formation of diastereomeric salts of the racemic amines with optically active acids such as D- and L-tartaric acid. Determination of absolute stereochemistry can be achieved in a number of ways including X-ray analysis of a suitable crystalline derivative.

A useful preparation of the chiral intermediate 19 is shown n Scheme 5.

SCHEME 5

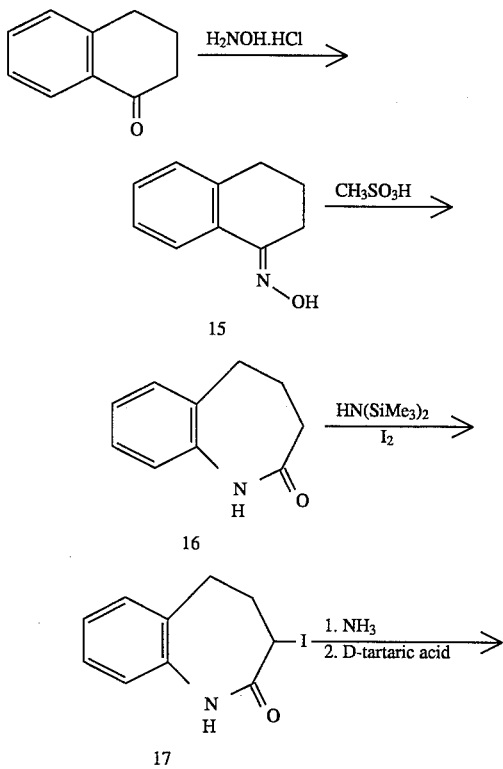

-continued
SCHEME 5

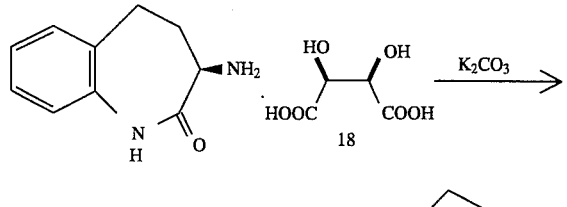

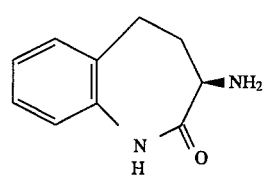

19

Conversion of 1-tetralone to the seven-membered benzolactam 16 is achieved by Beckman rearrangement of the intermediate oxime 15. rearrangement of the intermediate oxime 15. gives the 3-iodo derivative 17 which is sequentially treated with ammonia and D-tartaric acid to give the diastereomeric D-tartrate salt 18 after recrystallization. Liberation of the free amine 19 is achieved by neutralization of the D-tartrate salt with potassium carbonate followed by extractive isolation.

Intermediates of Formula II wherein X is a sulfur atom are prepared by methods described in the literature and known to those skilled in the art. As illustrated in Scheme 6, the seven-membered ring analog 27 is prepared from a protected derivative of cysteine 21 by the method of Slade, et al, J. Med. Chem., 28, 1517–1521 (1985) and references cited therein (CBz=benzyloxycarbonyl).

SCHEME 6

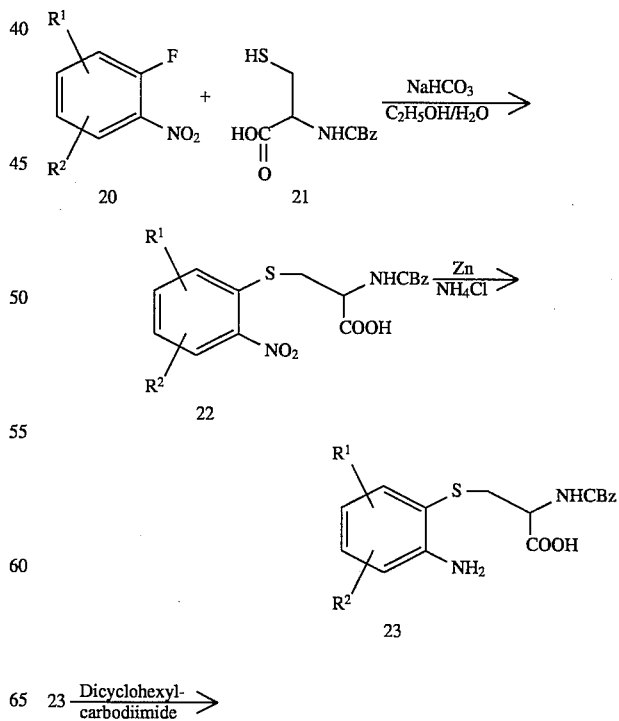

23 $\xrightarrow{\text{Dicyclohexyl-carbodiimide}}$

SCHEME 6 (continued)

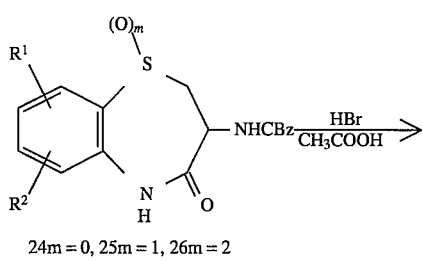

24 m = 0, 25 m = 1, 26 m = 2

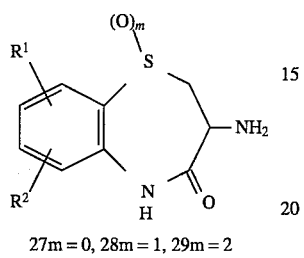

27 m = 0, 28 m = 1, 29 m = 2

Sulfoxide and sulfone intermediates 28 and 29 are prepared by oxidation of 24 with various oxidants such as sodium periodate or meta-chloro-perbenzoic acid. Eight-membered ring intermediates of Formula II wherein X is sulfur can be prepared by an analogous route starting from derivatives of homo-cysteine.

Intermediates of Formula II wherein X is an oxygen atom are prepared by methods described in the literature and known to those skilled in the art. For example, the seven-membered ring analog 26 can be prepared from a substituted derivative of 3-(2-nitrophenoxy) propanoic acid 30 by the method of J. Ott, Arch. Pharm (Weinheim. Ger.), 323(9), 601–603 (1990).

SCHEME 7

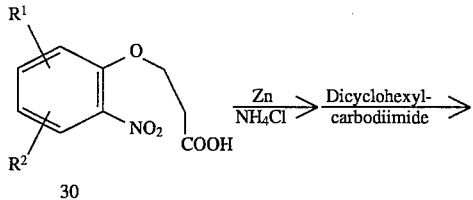

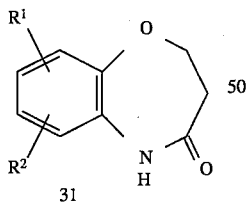

Six-membered ring analogs wherein X is oxygen (33) may be prepared by reaction of a substituted derivative of 2-aminophenol 32 with chloroacetyl chloride by the method of Huang and Chen, Synthesis, 10, 851 (1984) and references cited therein. Subsequent incorporation of an amino group at the 3 position of either 31 or 33 is achieved by the methods described in Scheme 4.

SCHEME 8

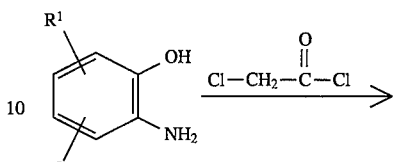

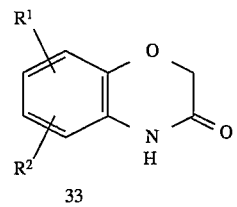

Seven-membered ring analogs of Formula II wherein X is C=O can be prepared from derivatives of tryptophan as described in the Australian Journal of Chemistry, 33, 633–640 (1980). Seven-membered ring analogs of Formula II wherein X is CH=CH can be prepared from the aforementioned analogs wherein X is C=O. Treatment of 34 with chemical reducing agents such as sodium borohydride in a polar solvent such as methanol or ethanol results in reduction to give the secondary alcohol derivative 35 (X=CHOH).

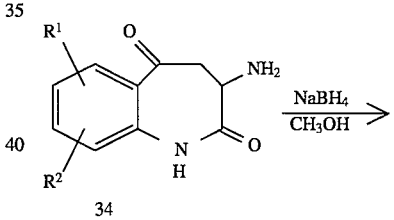

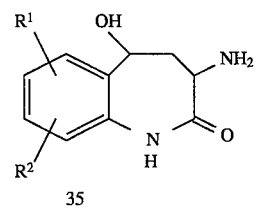

Dehydraton of 35 can be achieved by several methods described in the literature and familiar to those skilled in the art. For examle, treatment of 35 in an inert solvent, such as benzene, with a strong acid such as p-toluenesulfonic acid, will result in dehydration to the unsatured analog 36.

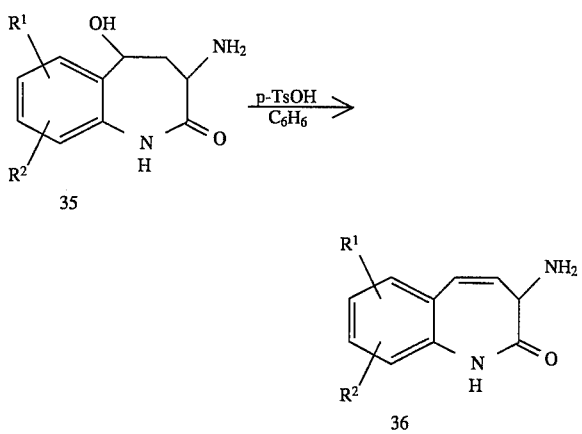

Intermediates of formula II can be further elaborated to new intermediates (formula III) which are substituted on the amino group (Scheme 9). Reductive alkylation of II with an aldehyde is carried out under conditions known in the art: for example, by catalytic hydrogenation with hydrogen in the presence of platinum, palladium or nickel catalysts or with chemical reducing agents such as sodium cyanoborohydride in an inert solvent such as methanol or ethanol.

SCHEME 9

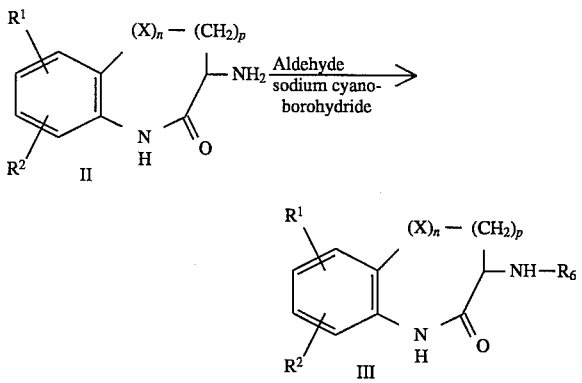

Attachment of the amino acid sidechain to intermediates of formula III is accomplished by the route shown in Scheme 10. Coupling is conveniently carried out by the use of an appropriately protected amino acid derivative, such as that illustrated by formula IV, and a coupling reagent such as benzotriazol-1-yloxytris(dimethylamino)phosphonium hexafluorophosphate ("BOP") in an inert solvent such as methylene chloride. Separation of unwanted side products, and purification of intermediates is achieved by chromatography on silica gel, employing flash chromatography (W. C. Still, M. Kahn and A. Mitra, J. Org. Chem., 43, 2923 (1978) or by medium pressure liquid chromatography.

SCHEME 10

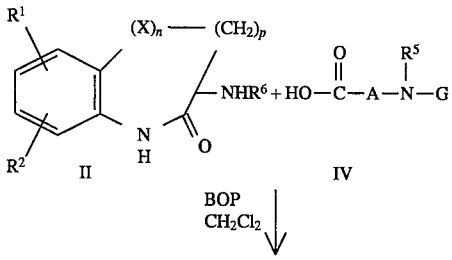

-continued
SCHEME 10

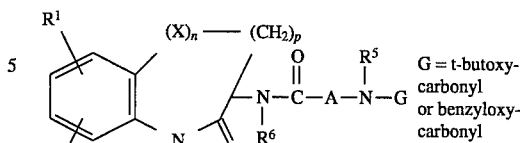

The protected amino acid derivatives IV are, in many cases, commercially available in t-butoxycarbonyl (BOC) or benzyloxycarbonyl (CBz) forms. A useful method to prepare the preferred sidechain 41 is shown in Scheme 11.

SCHEME 11

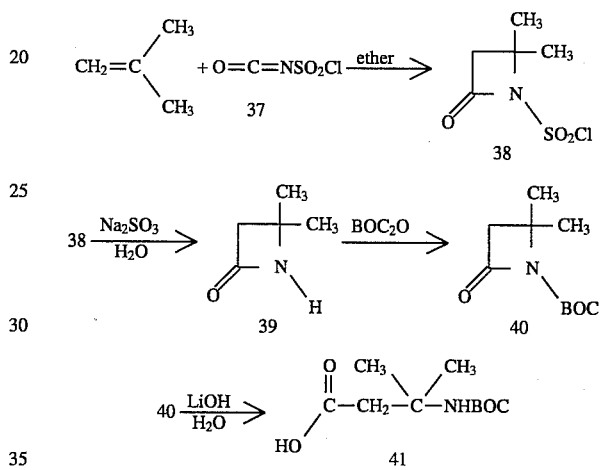

Reaction of isobutylene with N-chlorosulfonylisocyanate 37 in diethyl ether gives the azetidinone derivative 38. Removal of the chlorosulfonyl group with aqueous sodium sulfite followed by reaction with di-t-butyl-dicarbonate gives the BOC-protected intermediate 40. Alkaline hydrolysis gives the protected amino acid derivative 41 in good overall yield.

Intermediates of formula VII can be prepared as shown in Scheme 12 by treatment of the desired lactam intermediate V with an alkylating agent VI, wherein L is a good leaving group such as Cl, Br, I, O-methanesulfonyl or O-(p-toluenesulfonyl). Alkylation of intermediates of formula V is conveniently carried out in anhydrous dimethyl formamide (DMF) in the presence of bases such as sodium hydride or potassium t-butoxide for a period of 0.5 to 24 hours at temperaturs of 20°–100° C. Substituents on the alkylating agent VI may need to be protected during alkylation. A description of such protecting groups may be found in *Protective Groups in Organic Synthesis*, T. W. Greene, John Wiley and Sons, New York, 1981.

SCHEME 12

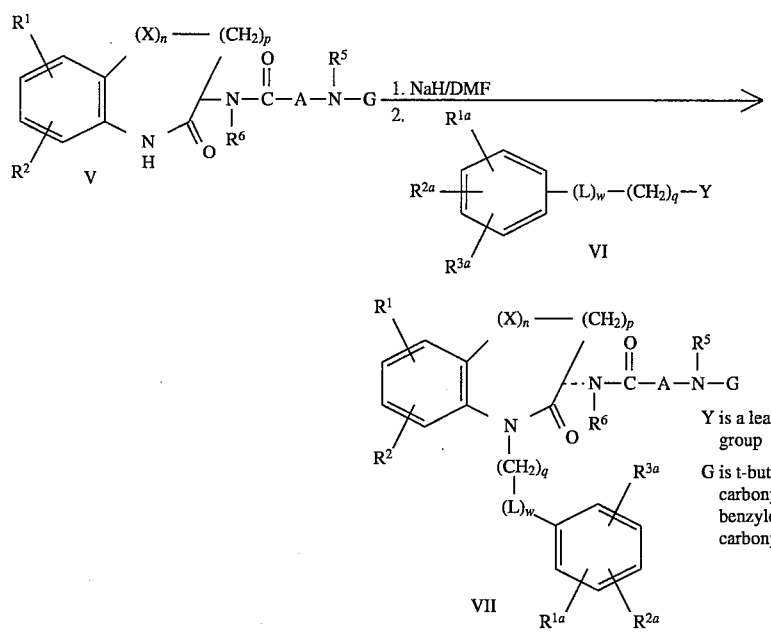

Alkylaying agents VI are in some cases commercially available or may be prepared by methods described in the literature and familiar to one skilled in the art. In general, compounds VIIa where $R^{3a}$ or $R^{3b}$ is $R^9$ can be prepared from intermediates of formula VII wherein $R^{3a}$ or $R^{3b}$ is an appropriate functional group that can be elaborated into the desired heterocycle $R^9$ by methods described in the literature and familiar to one skilled in the art. An alternative and preferred route is shown in Scheme 13 and involves reaction of intermediates of formula V with alkylating agents VIa, into which the heterocyclic moiety $R^9$ has already been incorporated.

Scheme 13

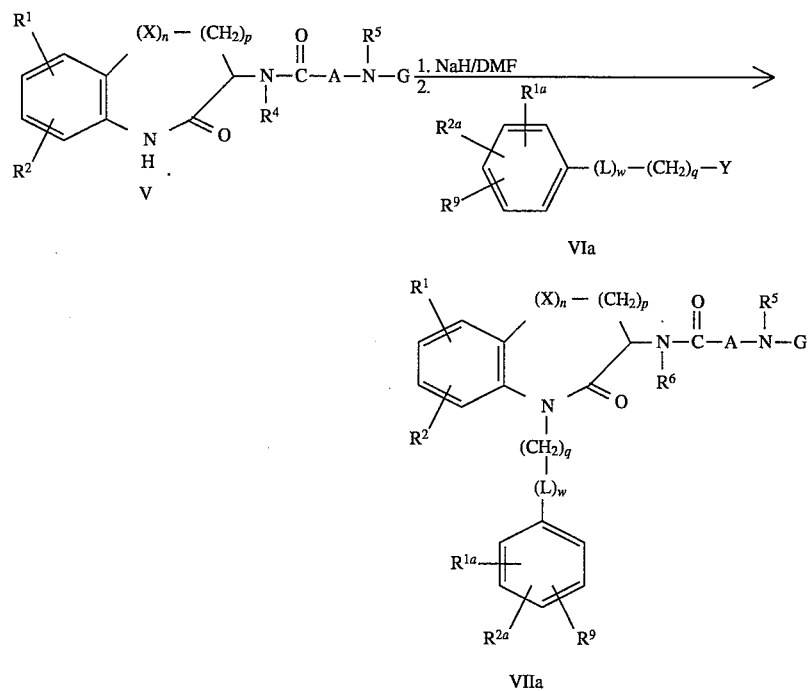

Y is a leaving group
G is t-butoxycarbonyl or benzyloxycarbonyl

Compounds VIIa wherein $R^9$ is a substituted 2-thiazolyl group may be prepared from nitrile intermediates 42 as indicated in Scheme 14. Formation of the thioamide intermediate 43 can be achieved through treatment of 42 with hydrogen sulfide in the presence of a base such as triethylamine, in a polar solvent such as pyridine. Reaction of 43 with bromo-ketal 44 in the presence of dilute aqueous acid will afford the thiazole product 45.

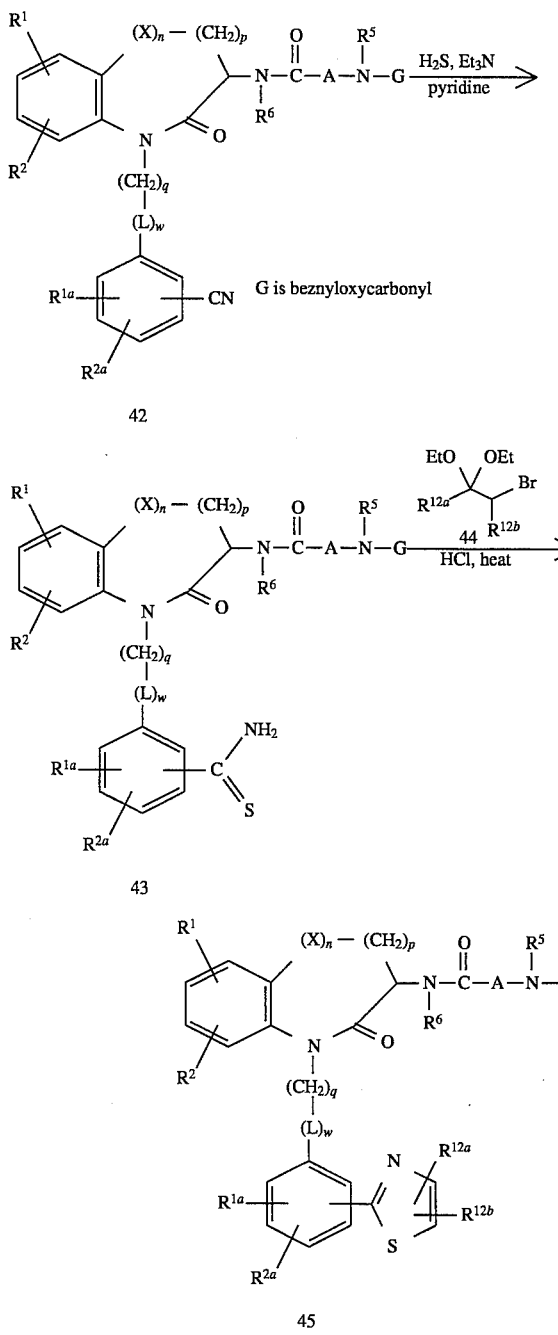

Scheme 14

42

43

45

A convenient route to the useful thiazole intermediate 50 is shown in Scheme 15. Thioamide 46 is obtained from 2-bromobenzonitrile by treatment with hydrogen sulfide and trietylemine in pyridine. Conversion to the thiazole intermediate 47 is achieved by treatment of 46 with bromoacetaldehyde diethylacetal in the presence of aqueous hydrochloric acid at elevated temperature. Coupling of 47 with 4-methylphenyltrimethylstannane 48 is conveniently carried out by treatment with a metal catalyst, such as bis(triphenylphosphine)palladium(II) chloride, in a polar solvent, such as dimethylformamide, at elevated temperature. Intermediate 49 is elaborated to the desired alkylating agent 50 by free radical bromination with N-bromo-succinimde and azobisisobutyronitrile (AIBN). Coupling of the alkylating agent 50 with compounds of formula V is carried out according to the conditions described in Scheme 13.

SCHEME 15

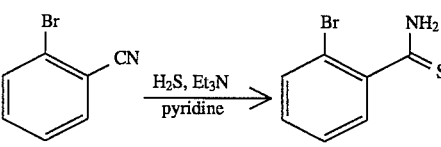

46

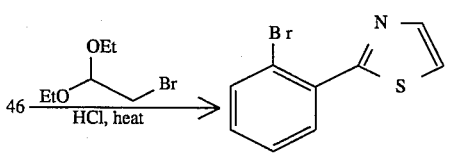

47

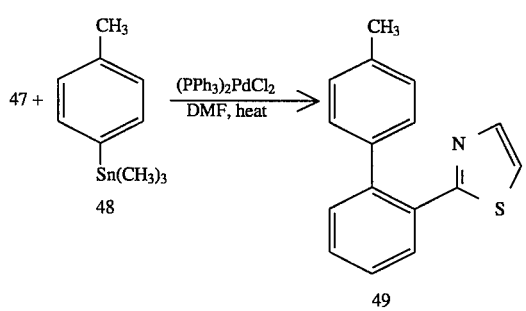

49

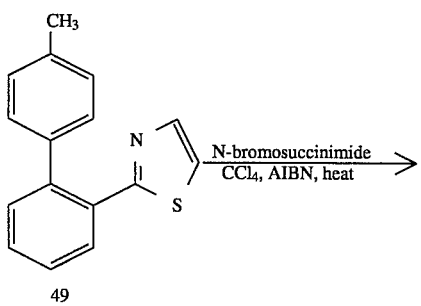

49

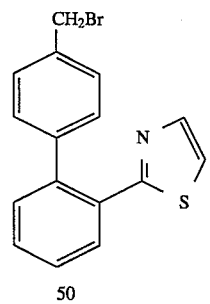

50

Scheme 16 describes a general route to 2-thienyl substituted compounds 54. Reduction of the nitro intermediate 51 is conveniently carried out by hydrogenation in the presence of a metal catalyst, such as palladium on carbon, in a polar solvent such as methanol or ethanol. It may be appreciated by one skilled in the art that the protecting group G in 51 must therefore be compatible with the conditions employed for its reduction. Diazotization of 52 may be carried out by treatment with isomylnitrite; the intermediate diazonium species 53 can be converted in situ to the desired thiophene compound 54 by treatment with thiophene at elevated temperature.

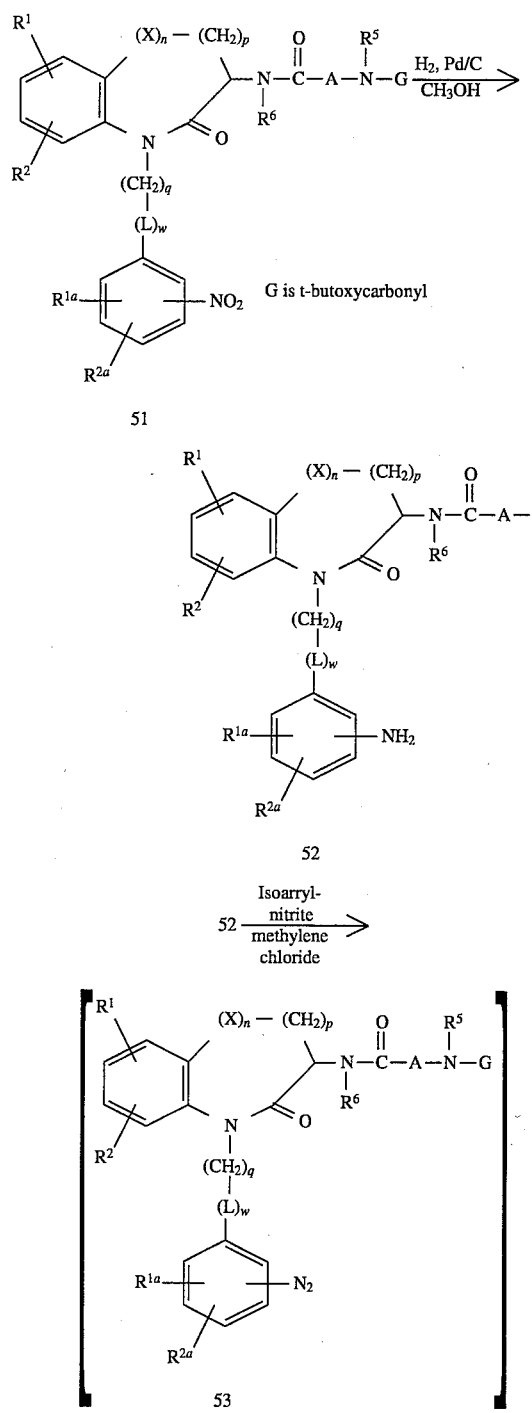

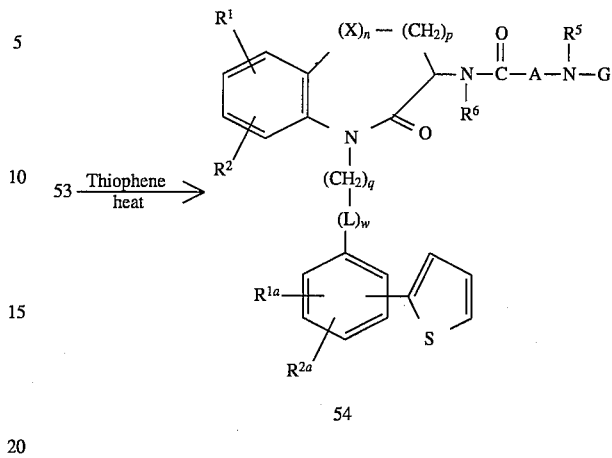

A useful preparation of the thienyl intermediate 57 is presented in Scheme 17. Thienylation of 2-bromoaniline is accomplished by formation of the diazonium salt, followed by treatment with thiophene. Coupling of 55 with 4-methylphenyltrimethylstannane 48 and subsequent bromination to give the desired intermediate 57 is achieved by the conditions described previously in Scheme 15. Coupling of the alkylating agent 57 with compounds of formula V is carried out according to the conditions described in Scheme 13.

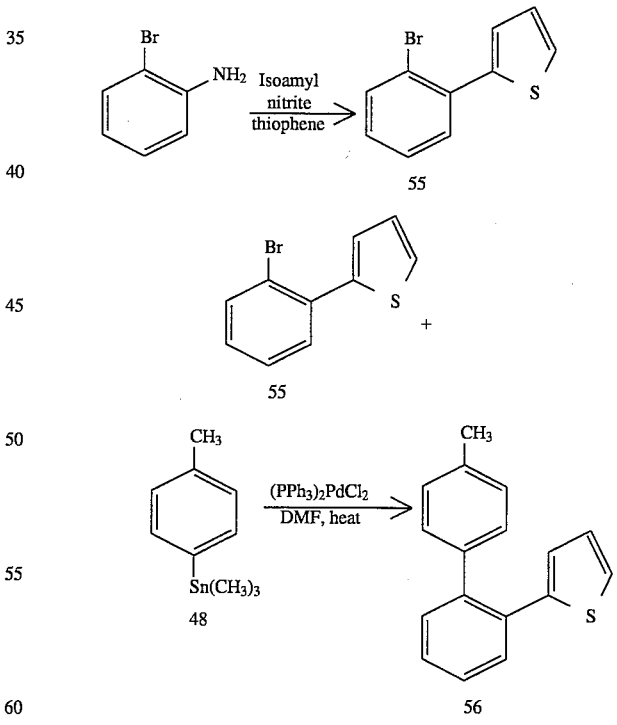

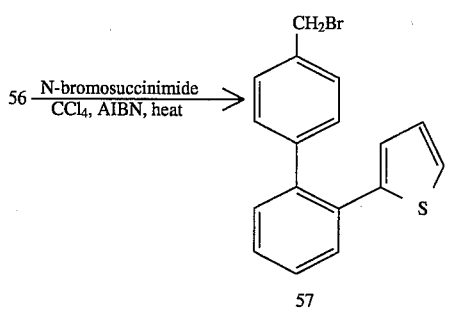

Scheme 8 describes a general route to 3-substituted pyrazole compounds 60. Formylation of acetyl compound 58 can be carried out by treatment with ethyl formate and sodium in a polar solvent such as ethanol. The formyl derivative, 59, isolated as its sodium salt, can be converted directly to the pyrazole product 60 by treatment with hydrazine.

SCHEME 18

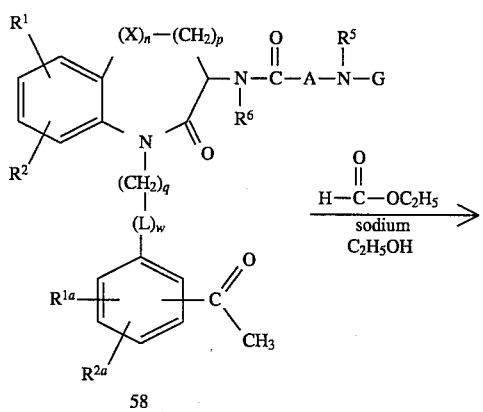

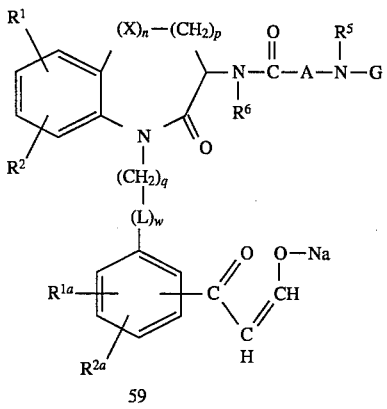

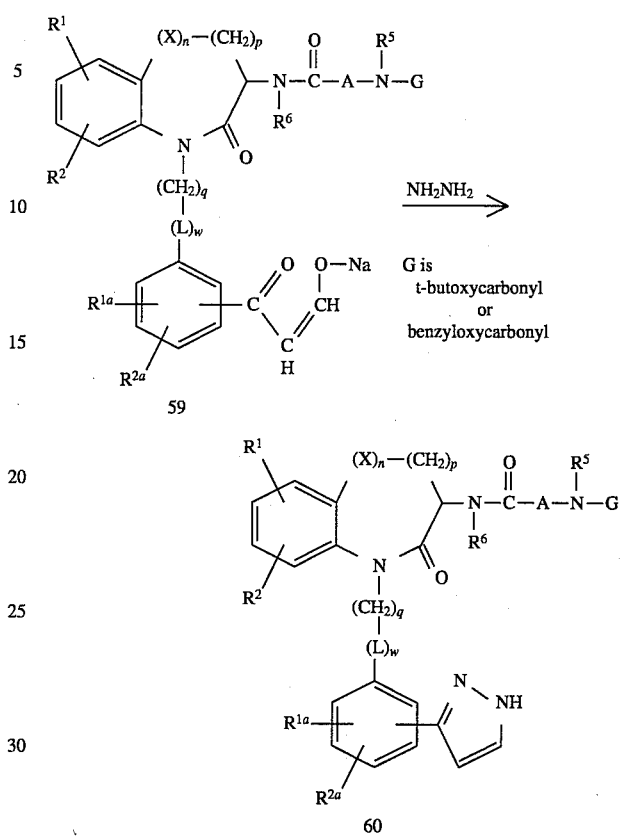

A convenient route to a preferred 3-substituted pyrazole intermediate 65 is shown in Scheme 19. Acetylbiphenyl 61, prepared from 2'-bromoacetophenone and 4-methylphenyltrimethylstannane according to the conditions described in Scheme 15, is converted to the sodium salt of the formyl derivatives 62 by treatment with sodium and ethyl formate. Reaction of 62 with hydrazine under basic conditions at elevated temperature affords the pyrazole 63 in moderate yield. Protection of the pyrazole ring as a tripheny methyl (trityl) derivative is achieved by treatment with triphenylmethylchloride in an inert solvent, such as methylene chloride, in the presence of a base, such as triethylamine. Bromination of 64 is accomplished with N-bromosuccinimide according to the procedure described in Scheme 15. Coupling of 65 with compounds of formula V is then carried out using the conditions described in Scheme 13.

Scheme 19

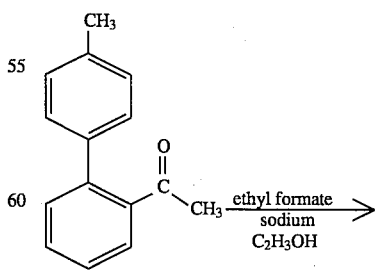

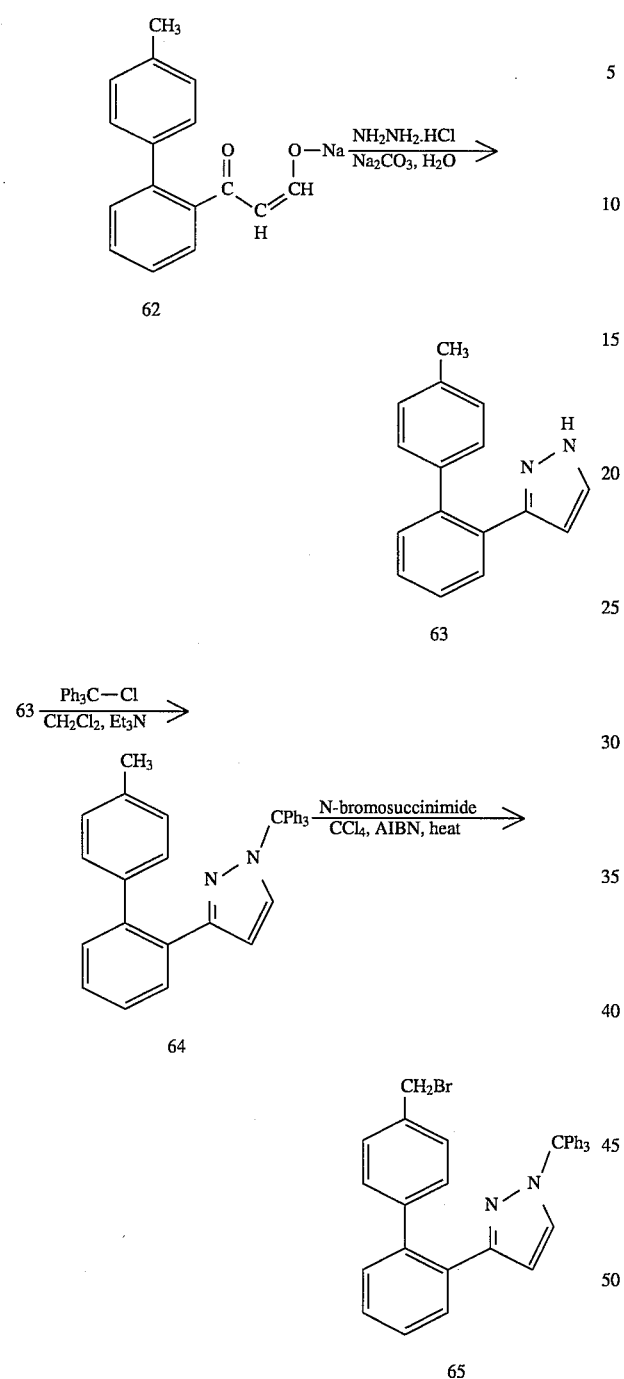

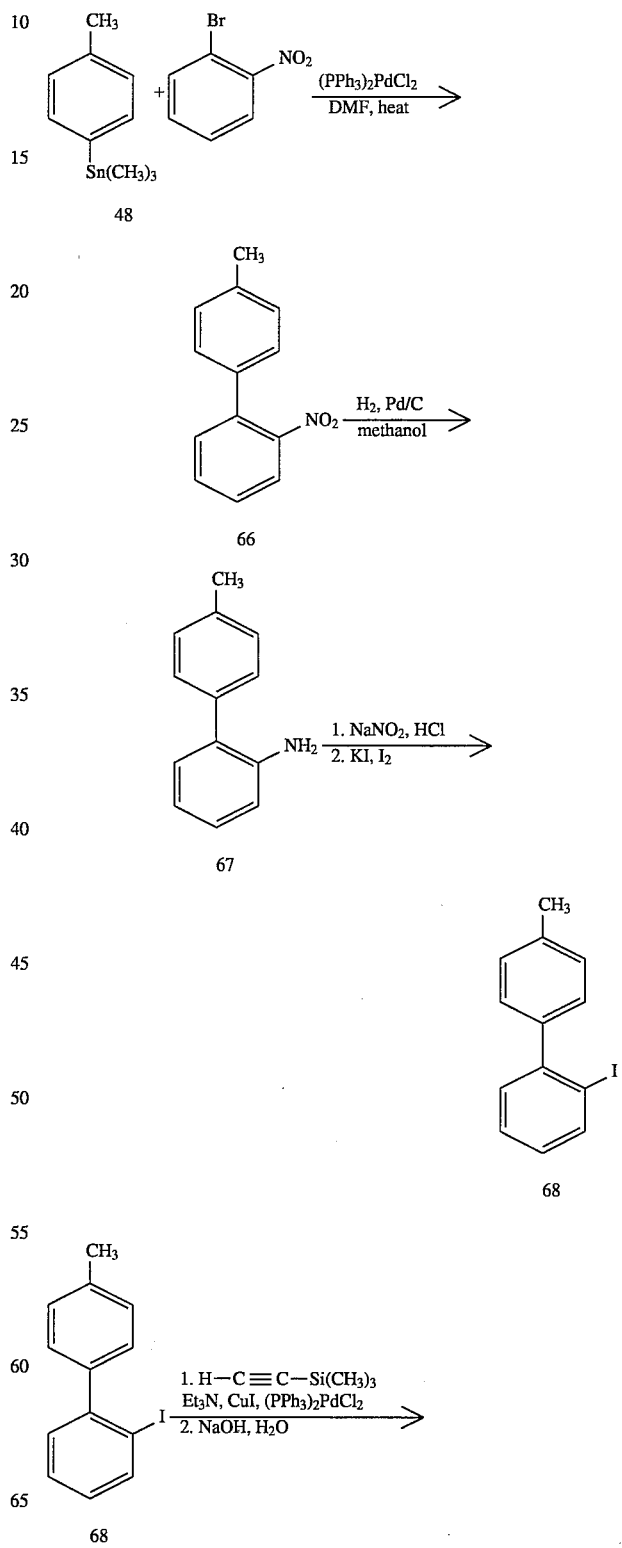

Desilylation with aqueous sodium hydroxide gives 69 which is converted to the 1,2,3-triazole compound 70 by treatment with trimethylsilyl azide at elevated temperature. Tritylation and bromination by the methods described previously afford the alkylating reagent 72. Reaction of 72 with compounds of formula V is then carried out using the conditions described in Scheme 13.

4-Substituted-1,2,3-triazole derivatives can also be prepared by a convergent route involving initial assembly of the appropriate triazole-containing alkylating agent. A useful preparation of the intermediate 72 is described in Scheme 20. Formation of 2'-nitro-4-methyl-1,1'-biphenyl 66 is carried out by coupling of the tin reagent 48 with 2-bromonitrobenzene under the conditions outlined in Scheme 15. Replacement of the 2'-nitro group with iodine is achieved by a three step sequence involving reduction to the amine compound 67 followed by diazotization and treatment with potassium iodide and iodine. Coupling of 68 with trimethylsilylacetylene is carried out with bis(triphenylphosphine)palladium(II) chloride, and cuprous iodide in triethylamine.

SCHEME 20 -continued

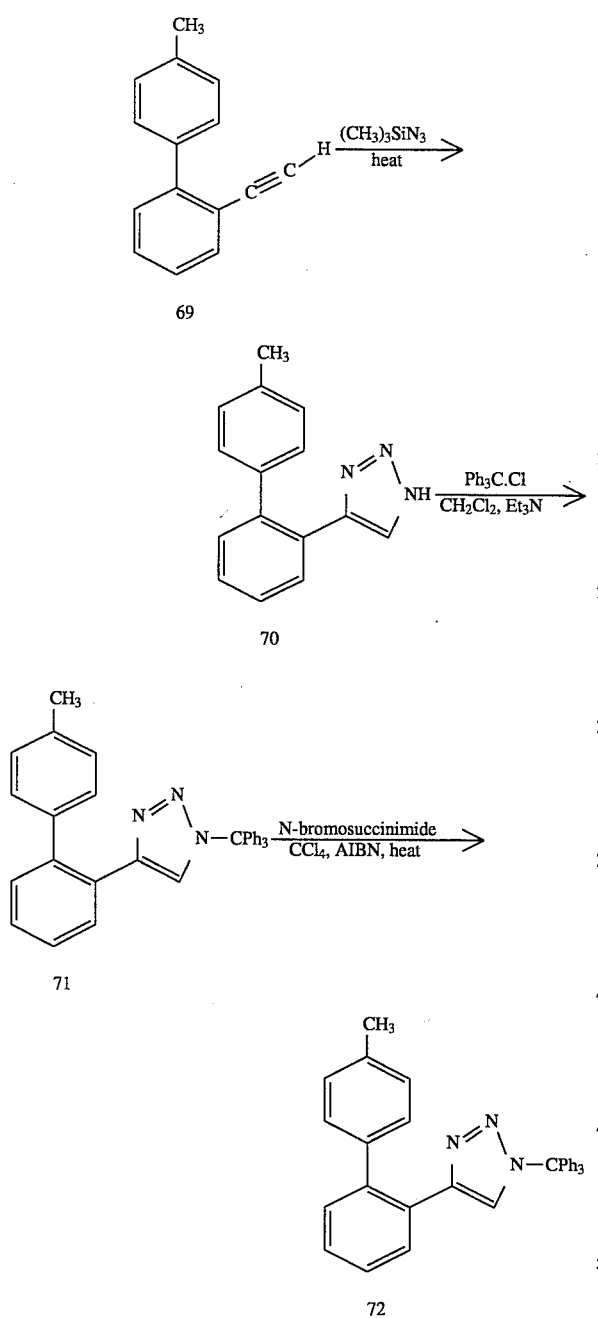

SCHEME 21

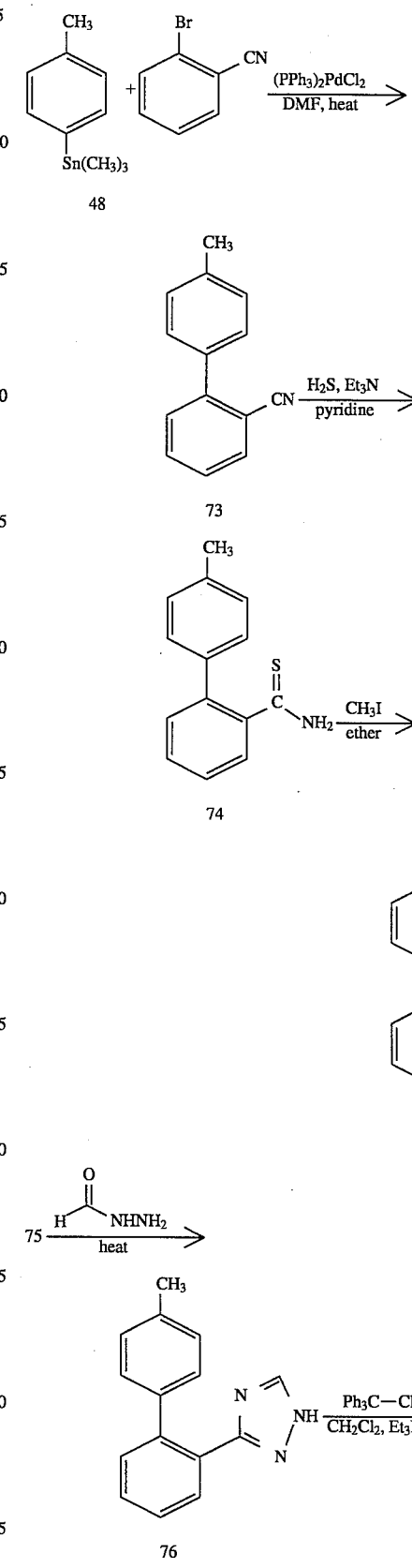

above. Reaction of 78 with compounds of formula V is then carried out using the conditions described in Scheme 13.

Isomeric 3-substituted-1,2,4-triazole derivatives are prepared in a similar manner. As indicated in Scheme 21, formation of 2'-cyano-4-methyl-1,1'-biphenyl 73 is carried out by coupling of the tin reagent 48 with 2-bromobenzonitrile using the conditions outlined in Scheme 15. Conversion to the thioamide 74 is performed at elevated temperature with hydrogen sulfide and triethylamine in pyridine under pressure. Treatment of 74 with methyl iodide gives the activated intermediate 75, which is elaborated to the 1,2,4-triazole compound 76 by treatment with formic hydrazide in dimethylformamide at elevated temperature. Protection as the trityl derivative 77 and conversion to the bromo compound 78 are carried out using the conditions described

SCHEME 21 -continued

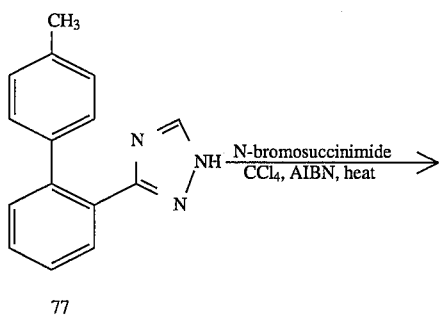

77

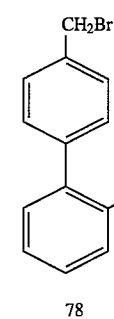

78

Scheme 22 describes a general route to 2-substituted imidazole compounds 82. Methyl ester 79 can be reduced with a complex metal hydride reagent such as diisobutylaluminum hydride (DIBAL) to the aldehyde 80. An alternate four-step route would involve hydrolysis of ester 79 under basic conditions, followed by formation of a mixed anhydride using isobutyl chloroformate; reduction of the mixed anhydride with sodium borohydride and subsequent oxidation of the benzyl alcohol product with dimethyl sulfide and oxalyl chloride (Swern conditions). Elaboration of aldehyde 80 to the desired imidazole compound 82 can be achieved by reaction with diketone 81 in the presence of an ammonium salt, such as ammonium acetate, in a polar solvent such as methanol or ethanol.

SCHEME 22

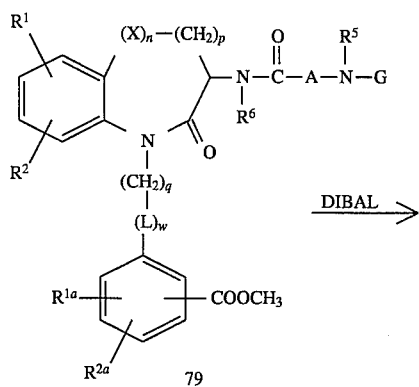

79

SCHEME 22 -continued

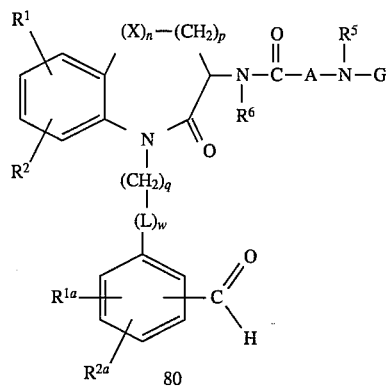

80

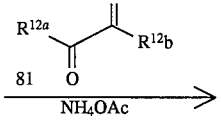

81

NH₄OAc

G is t-butoxycarbonyl
or
benzyloxycarbonyl

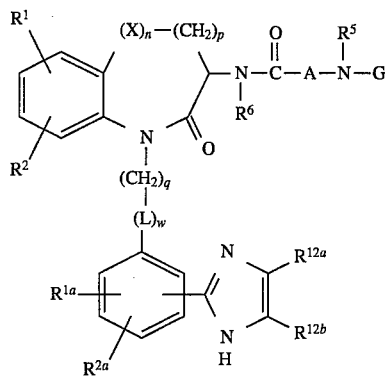

82

Intermediate 82 can be converted to a new intermediate 83 as indicated in Scheme 23 by alkylation with $R^{13}$-Cl in the presence of a base, such as sodium hydride, in a polar solvent, such as dimethyl formamide.

SCHEME 23

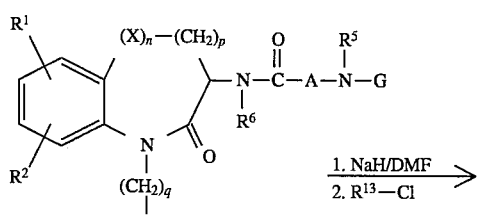

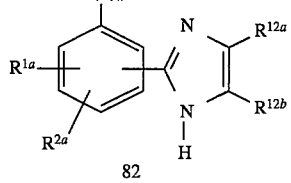

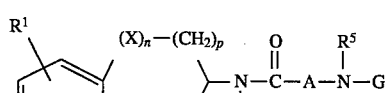

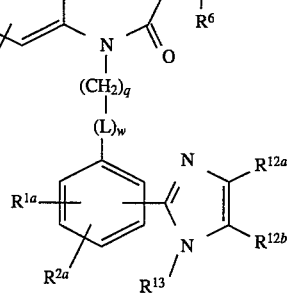

A convergent route to the useful intermediate 89 is outlined in Scheme 24. Metallation of 4-bromobenzyl t-butyldimethylsilylether 84 with t-butyllithium followed by treatment with zinc chloride gives the intermediate zinc compound 85 which is subsequently coupled with 86 through the use of a transition metal catalyst, such as bis(triphenylphosphine)nickel(II) chloride. Elaboration of the biphenyl compound 87 to the alkylating agent 88 is accomplished by sequential removal of the silyl protecting group by treatment with tetra-n-butylammonium fluoride followed by reaction with methanesulfonic anhydride and triethylamine. Reaction of 88 with compounds of formula V to give 89 is carried out using the conditions described in Scheme 13.

SCHEME 24

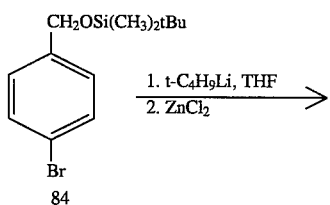

-continued
SCHEME 24

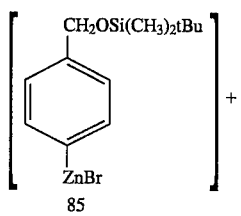

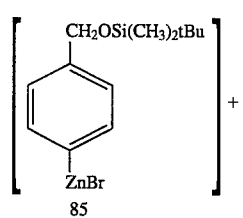

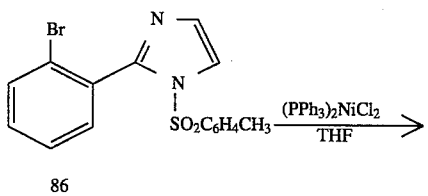

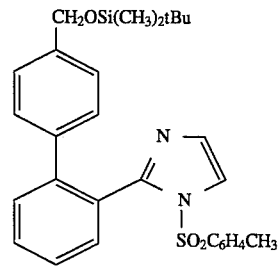

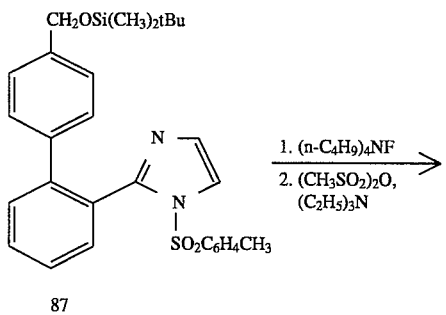

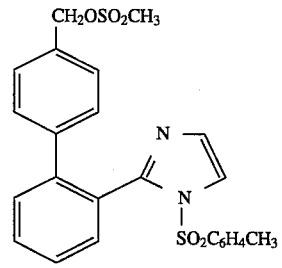

SCHEME 24 -continued

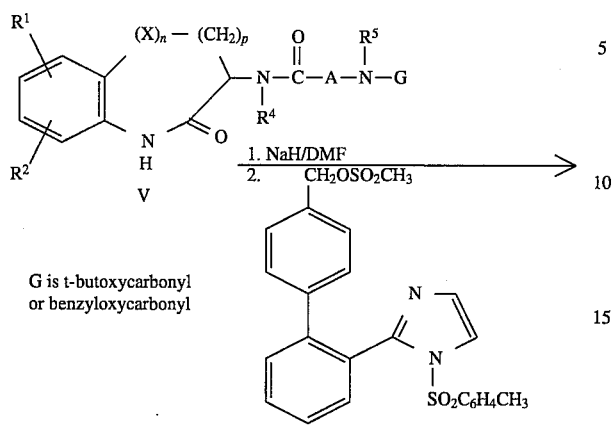

88

G is t-butoxycarbonyl
or benzyloxycarbonyl

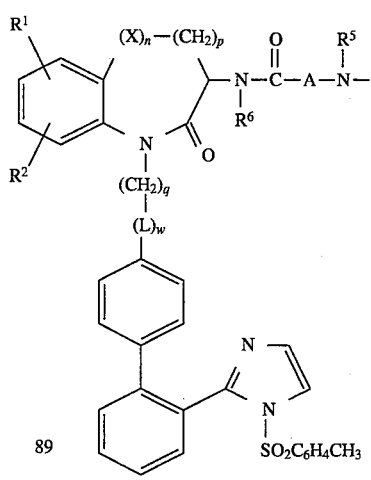

89

SCHEME 25

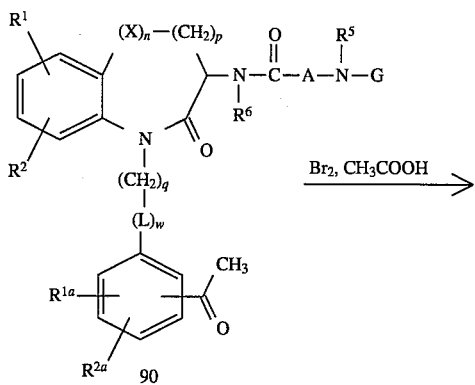

90

A general route to 4-substituted imidazole derivatives 92 is depicted in Scheme 25. Acetyl compound 90 can be brominated through the use of bromine in acetic acid. Reaction of the bromide 91 with formamidine acetate in a polar solvent will give the imidazole product 92.

SCHEME 25 -continued

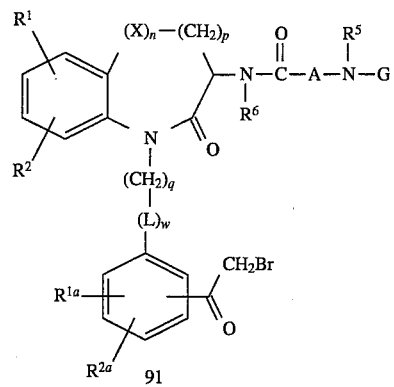

91

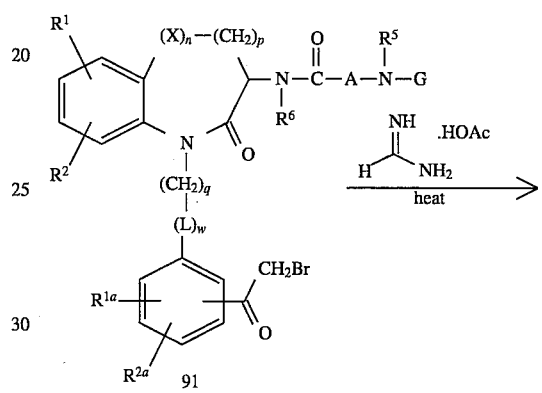

91

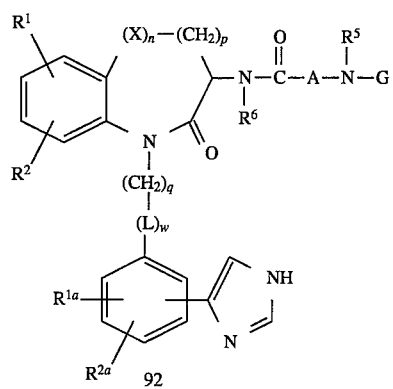

92

A useful route to the protected 4-substituted imidazole intermediate 96 is illustrated in Scheme 26. Coupling of 2'-bromoacetophenone and 4-methylphenyltrimethylstannan according to the conditions described in Scheme 15 gives 2'-acetyl-4-methyl-1,1'-biphenyl 61 which is brominated with bromine in acetic acid to give the phenacyl derivative 93. Imidazole formation is achieved by reaction of 93 with formamidine acetate in a polar solvent at elevated temperature. Protection of 94 as the trityl derivative 95 and conversion to the bromo compound 96 are carried out using the conditions described above. Reaction of 96 with compounds of formula V is then carried out using the conditions described in Scheme 13.

SCHEME 26

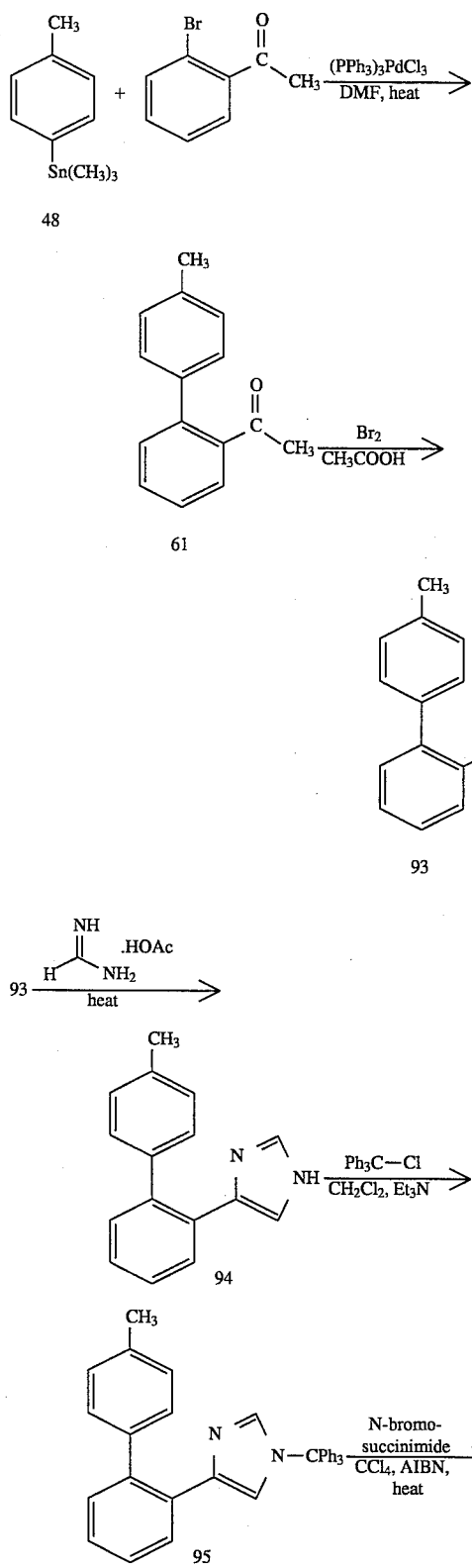

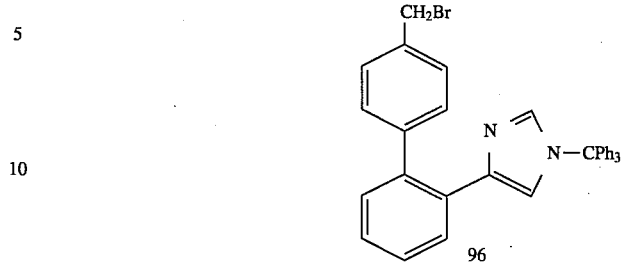

Compounds of formula I wherein $R^9$ is a substituted triazolinone, such as compound 99, can be prepared from intermediates described herein by methods described in the literature, such as those detailed by J. Lyga, et al. in Synth. Comm., 16, 163 (1986) and illustrated in Scheme 27. Amine 52 can be transformed to the corresponding hydrazine derivative 97 by a two-step sequence involving formation of a diazonium salt, followed by reduction with tin(II) chloride. Treatment of 97 with an appropriately substituted pyruvic acid reagent 98 followed by reaction with diphenylphosphoryl acids will give the desired triazolinone 99.

SCHEME 27

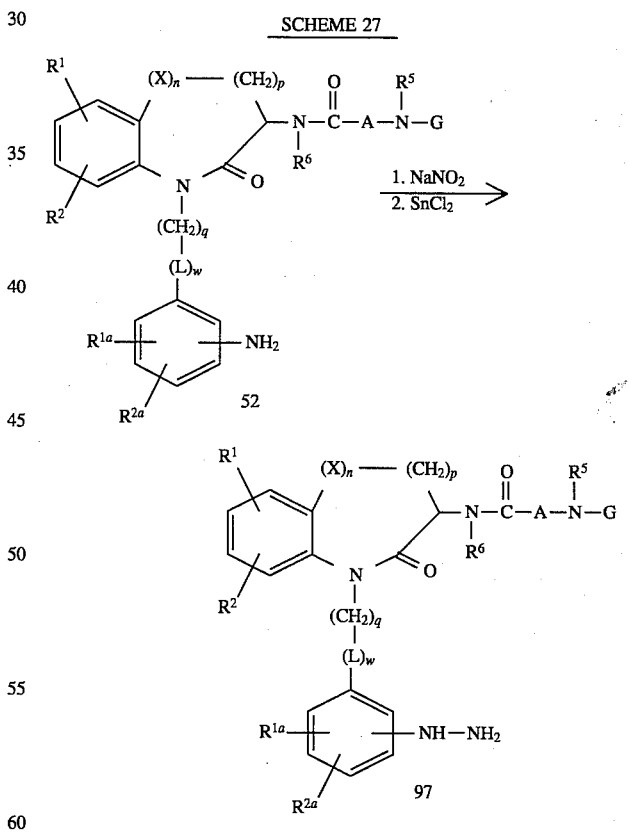

-continued
SCHEME 27

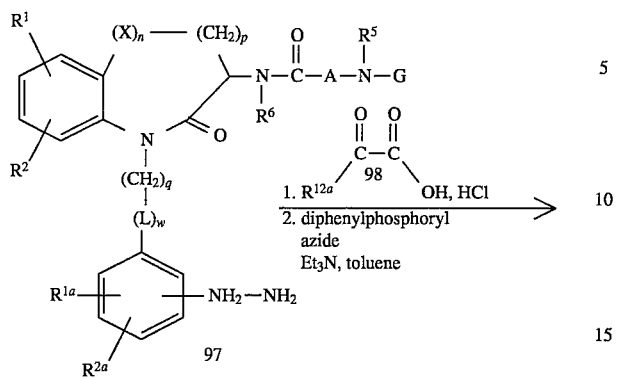

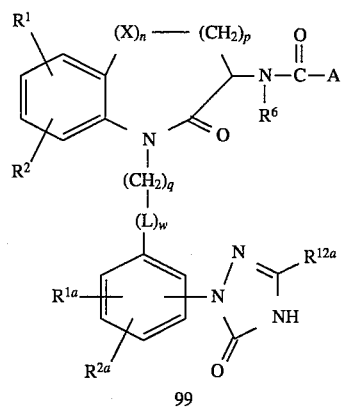

SCHEME 28

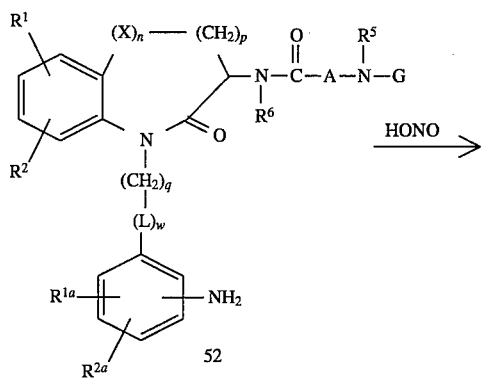

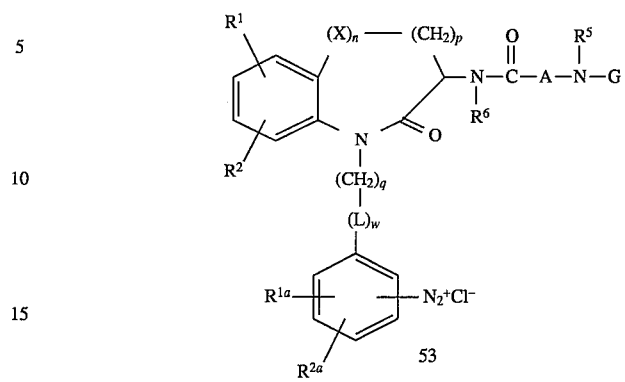

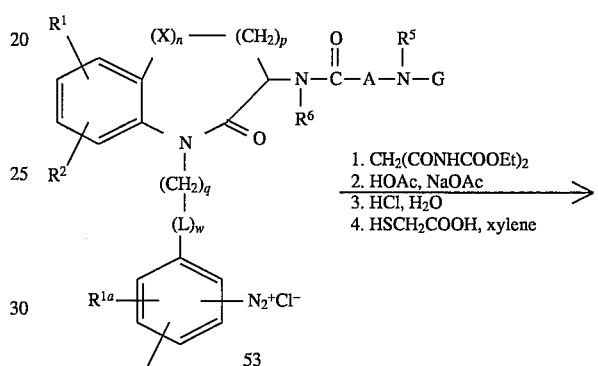

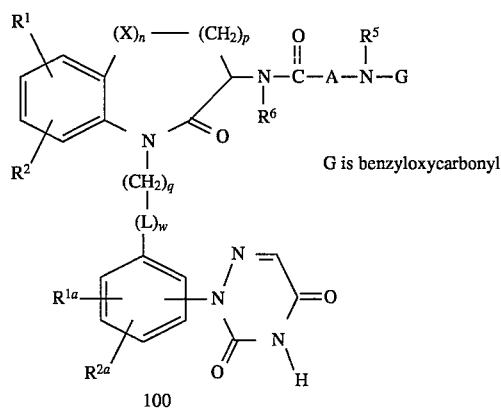

G is benzyloxycarbonyl

Analogs wherein $R^9$ is a substituted triazinone, such as compound 100, can be prepared from intermediates described herein by methods described in the literature, such as those detailed by M. Miller, et al, in J. Med. Chem., 24, 1337 (1981) and illustrated in Scheme 28. Diazonium salt 53, available from amine 52 by treatment with nitrous acid, can be converted into the desired compound 100 by a four-step sequence involving: 1) reaction with malonyldiurethane; 2) treatment with acetic acid and sodium acetate; 3) hydrolysis with aqueous hydrochloric acid, and 4) treatment with thioglycolic acid in xylene at elevated temperature.

Compounds of formula I wherein E is a carbamate or ester linkage can be prepared from acetophenone intermediates 58 as shown in Scheme 29. Reaction of 58 with a peroxycarboxylic acid, such as m-chloroperbenzoic acid (Baeyer-Villager reaction), leads to formation of the corresponding ester 101 which can be hydrolyzed under basic conditions to give phenol 102.

SCHEME 29
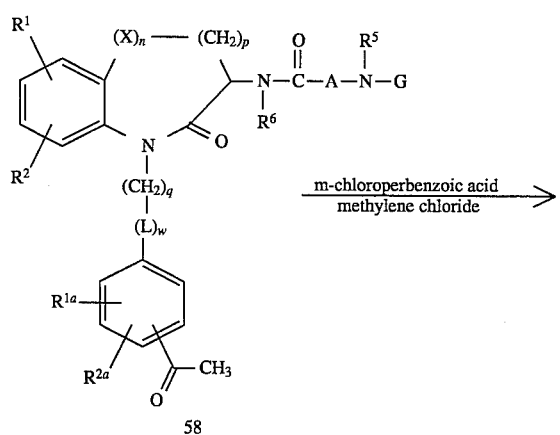
58
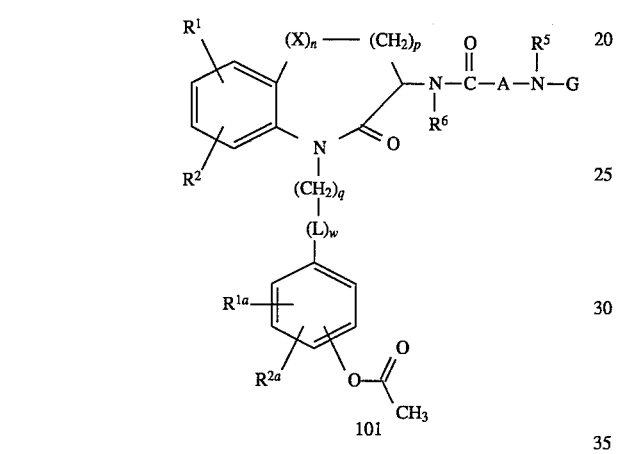
101
$101 \xrightarrow{\text{LiOH}}_{\text{H}_2\text{O}}$
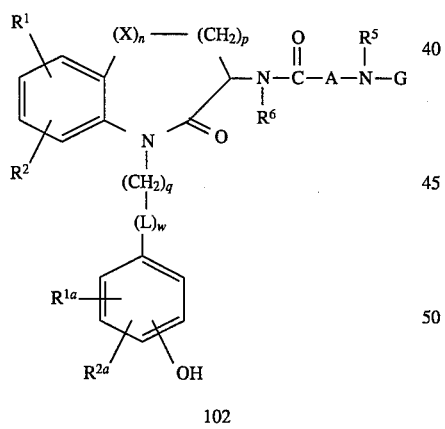
102
SCHEME 30
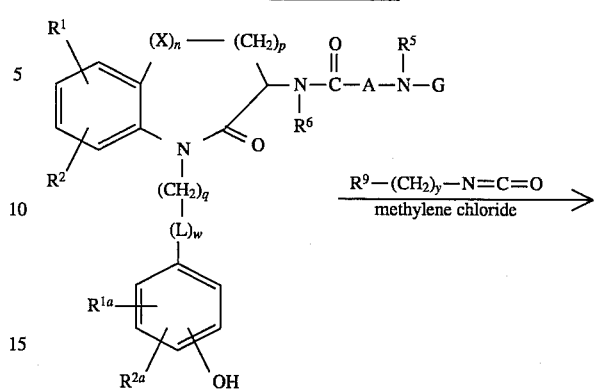
102
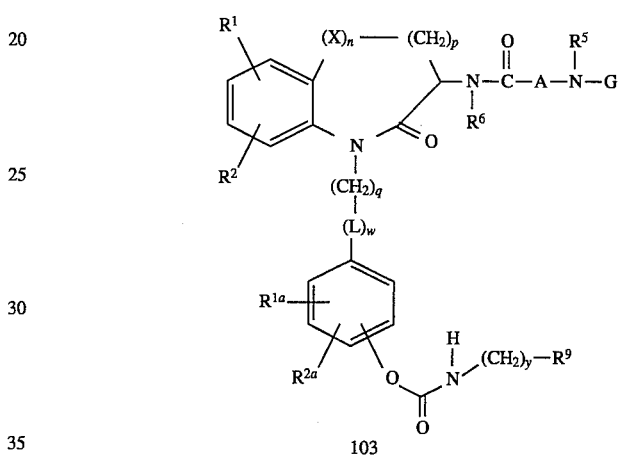
103
G is t-butoxycarbonyl
or
benzyloxycarbonyl
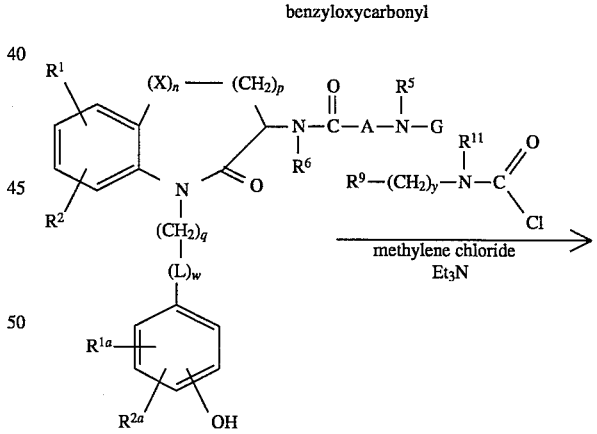
102
Illustrated in Scheme 30 are reactions of phenol 102 with suitable reagents to give carbamate compounds 103 and 104, and ester compounds 105.

SCHEME 30 -continued

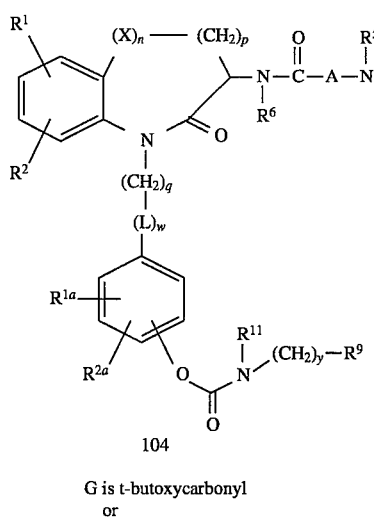

104

G is t-butoxycarbonyl
or
benzyloxycarbonyl

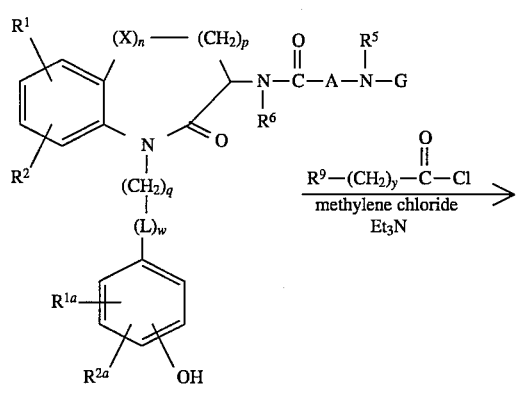

102

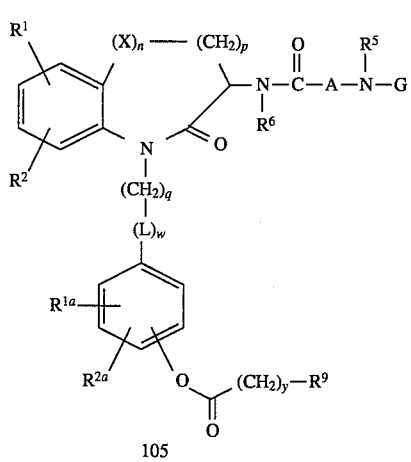

105

G is t-butoxycarbonyl
or
benzyloxycarbonyl

Compounds of formula I wherein E is a urea or carbamate linkage can be prepared from nitro compounds 51 as shown in Scheme 31. Reduction of 51 is conveniently carried out by hydrogenation in the presence of a metal catalyst, such as palladium on carbon, in a polar solvent such as methanol or ethanol. It may be appreciated by one skilled in the art that the protecting group G in 51 must therefore be compatible with the conditions employed for its reduction, hence G is taken as t-butoxycarbonyl. Reaction of 52 with phosgene, or an equivalent reagent such as bis(trichloromethyl)carbonate (triphosgene), results in formation of isocyanate 106.

SCHEME 31

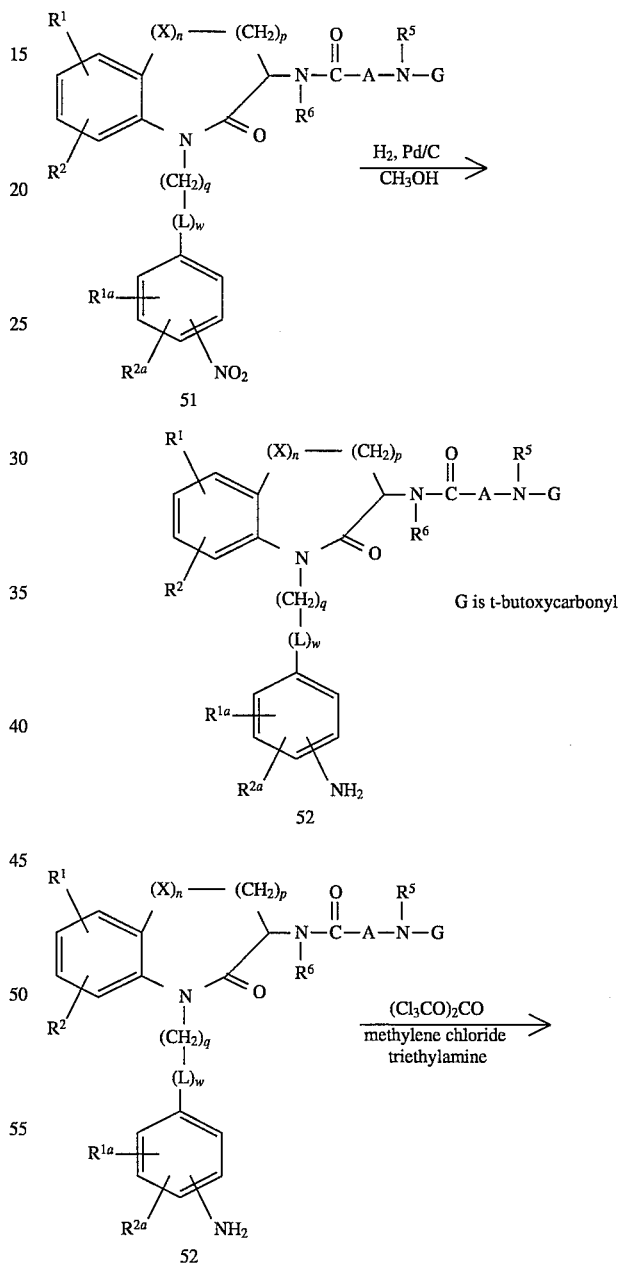

-continued
SCHEME 31

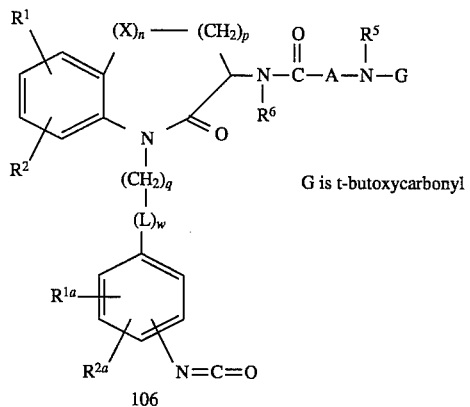

G is t-butoxycarbonyl

Scheme 32 illustrates the reactions of isocyanate 106 with appropriate reagents to form urea-linked compounds 107 and carbamate-linked compounds 108.

SCHEME 32

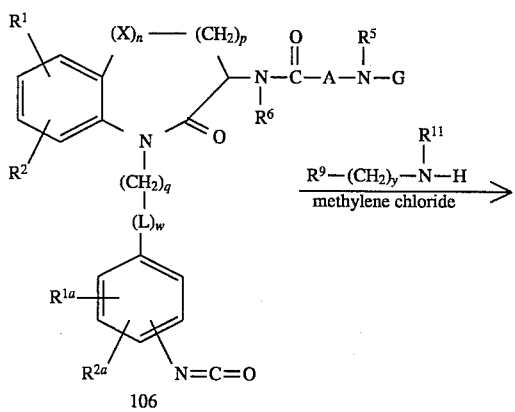

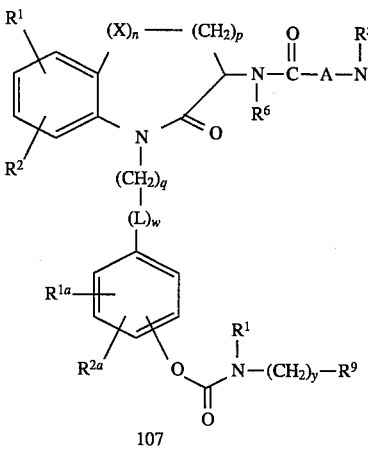

107

G is t-butoxycarbonyl

-continued
SCHEME 32

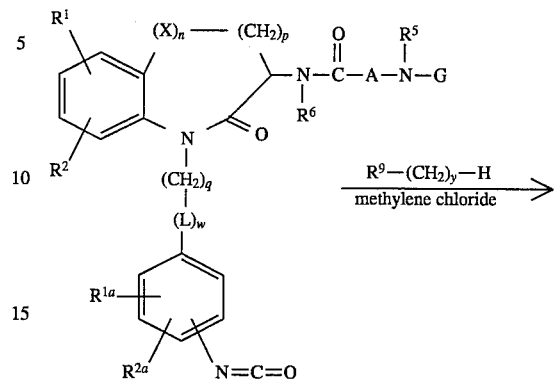

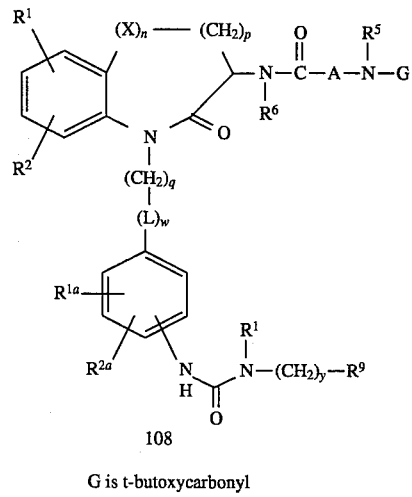

108

G is t-butoxycarbonyl

Aniline derivative 52 may be further converted to a substituted amine 109 by reductive amination with an aldehyde and a reducing agent such as sodium cyanoborohydride, as shown in Scheme 33.

SCHEME 33

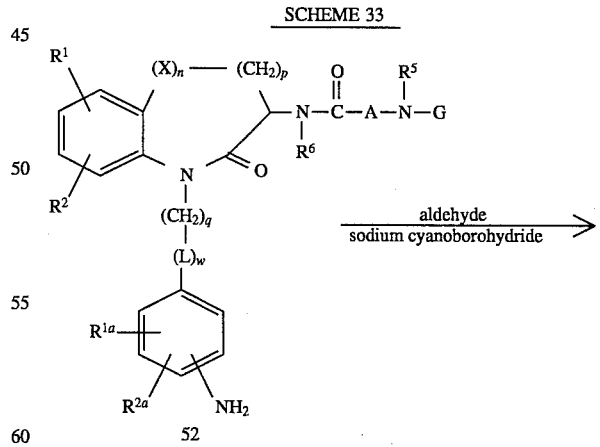

52

SCHEME 33 -continued
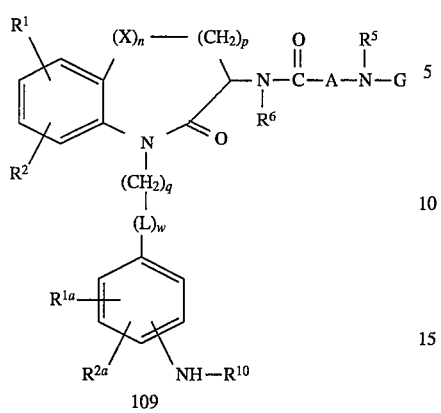
109
Scheme 34 shows transformations of amine 109 with the appropriate reagents to form urea-linked compounds 110 and 111, carbamate-linked compounds 112 and amide-linked analogs 113.
SCHEME 34
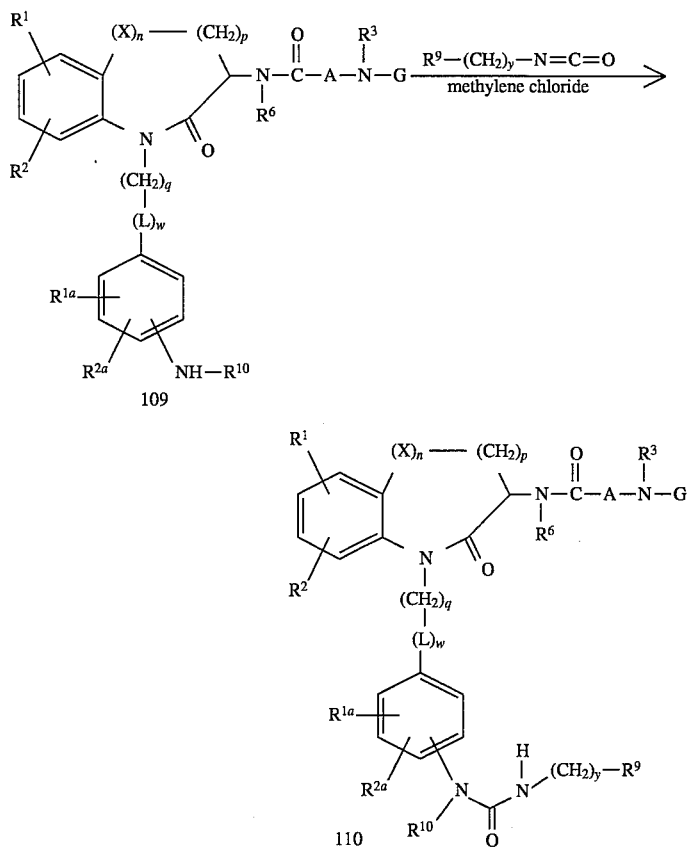
G is t-butoxycarbonyl or benzyloxycarbonyl -continued
SCHEME 34
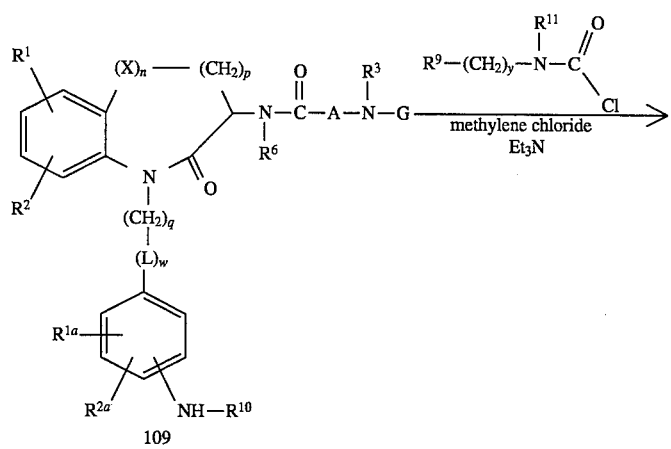
109
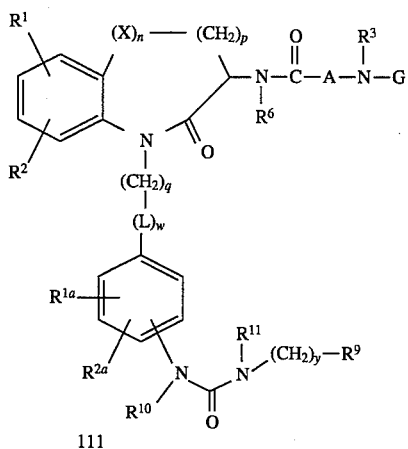
111
G is t-butoxycarbonyl or benzyloxycarbonyl
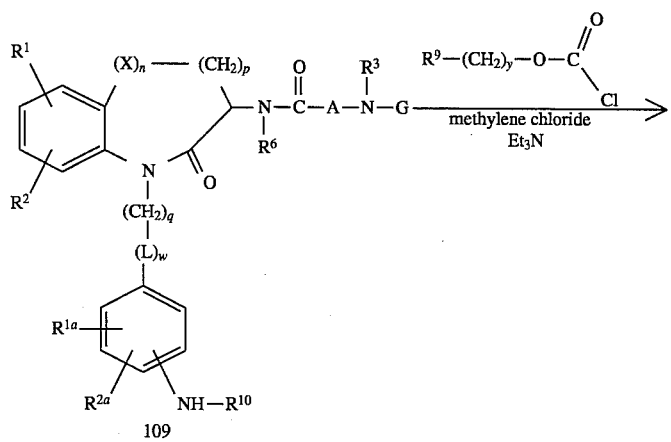
109

-continued
SCHEME 34

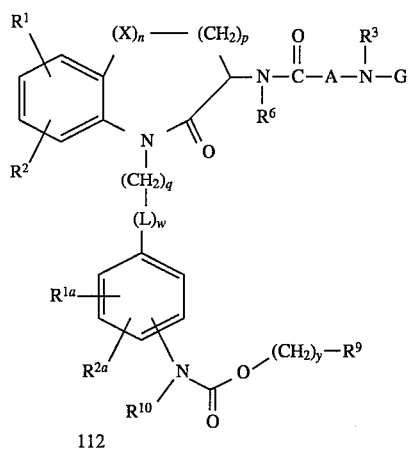

112

G is t-butoxycarbonyl or benzyloxycarbonyl

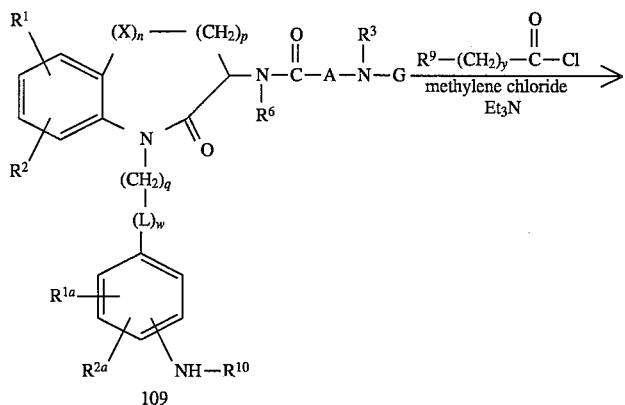

109

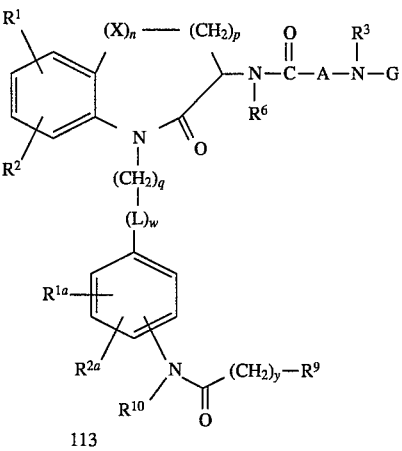

113

G is t-butoxycarbonyl or benzyloxycarbonyl

Compounds of formula I wherein E is —$CH_2N(R^{10})$— can be prepared from the t-butyl ester intermediate 114 as described in Scheme 35. Removal of the t-butyl ester through the use of trifluoroacetic acid will give the carboxylic acid 115. It may be appreciated by one skilled in the art that the protecting group G in 114 must therefore be compatible with the strongly acidic conditions employed for ester cleavage, hence G is taken as benzyloxycarbonyl. Conversion of the carboxylic acid to the benzylamine derivative 116 can be achieved by a five-step sequence consisting of: 1) formation of a mixed anhydride with isobutyl chloroformate; 2) reduction with sodium borohydride to the benzyl alcohol; 3) formation of the mesylate with methanesulfonyl chloride; 4) formation of the azide by reaction with sodium azide, and finally, 5) reduction of the azide with tin(II) chloride. The benzylamine intermediate 116 can be further elaborated to 117 by the aforementioned reductive amination procedure.

SCHEME 35
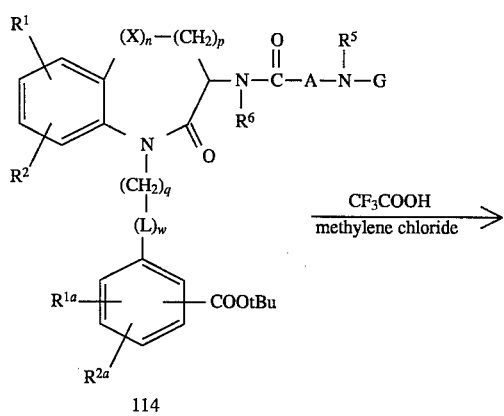
114
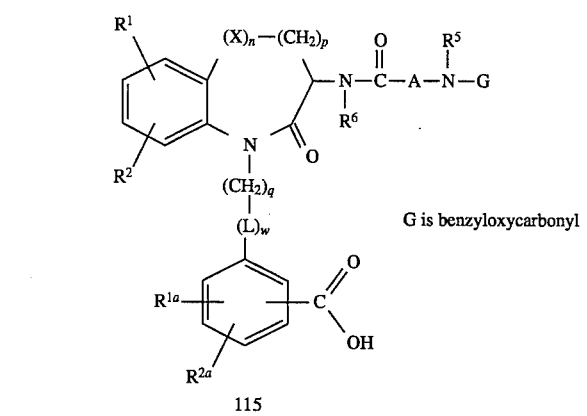
115
G is benzyloxycarbonyl
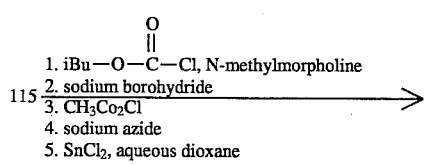
1. iBu—O—C(=O)—Cl, N-methylmorpholine
2. sodium borohydride
3. CH₃Co₂Cl
4. sodium azide
5. SnCl₂, aqueous dioxane
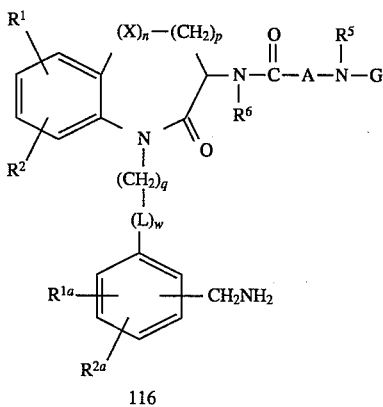
116
-continued
SCHEME 35
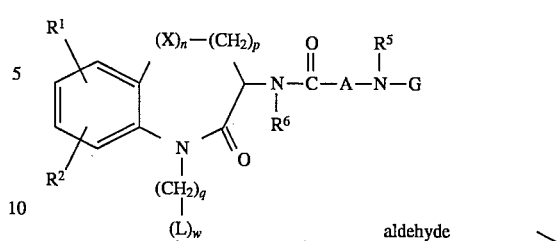
116
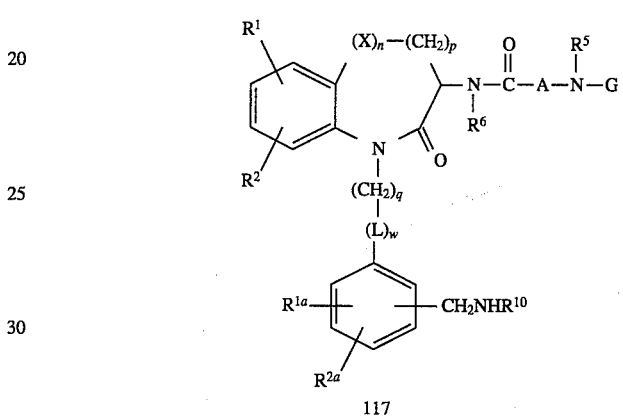
117
G is benzyloxycarbonyl
Reactions of amine 117 with the appropriate reagents to form urea-linked compounds 118 and 119, carbamate linked compounds 120, and amide-linked structures 121 are illustrated in Scheme 36.
SCHEME 36
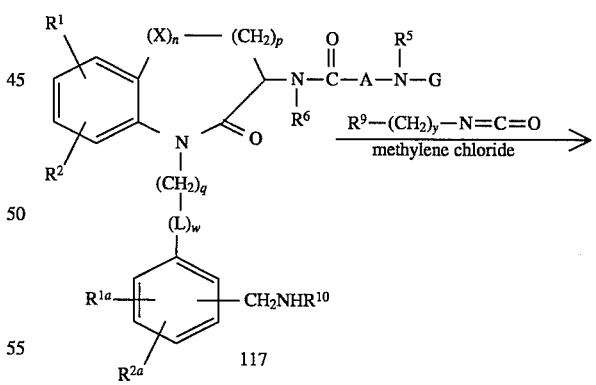
117

SCHEME 36 -continued

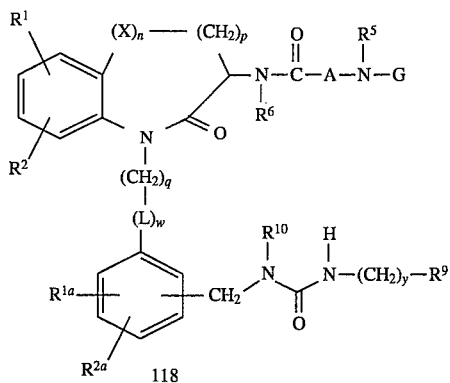
118
G is benzyloxycarbonyl

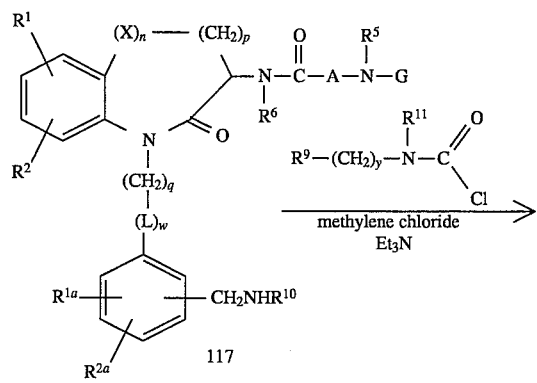
117

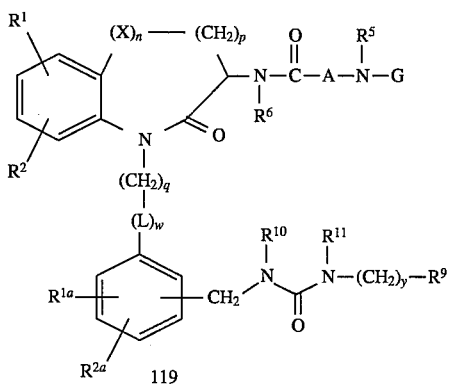
119
G is benzyloxycarbonyl

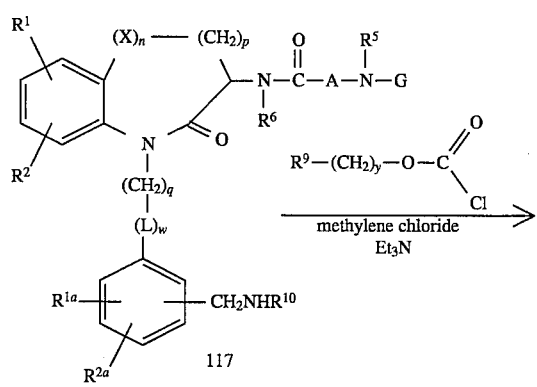
117

SCHEME 36 -continued

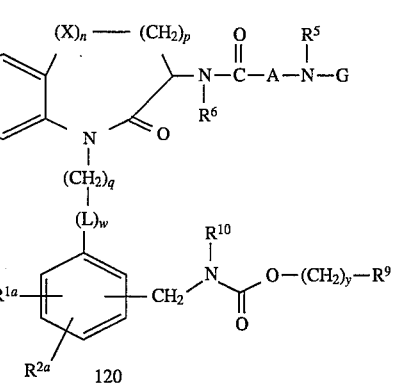
120
G is benzyloxycarbonyl

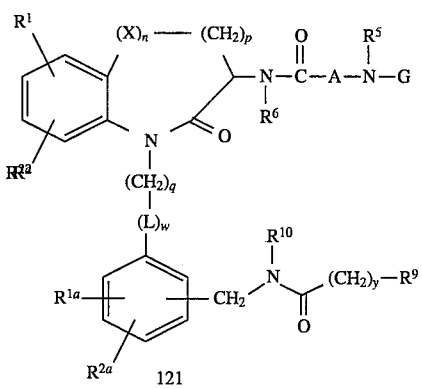
117

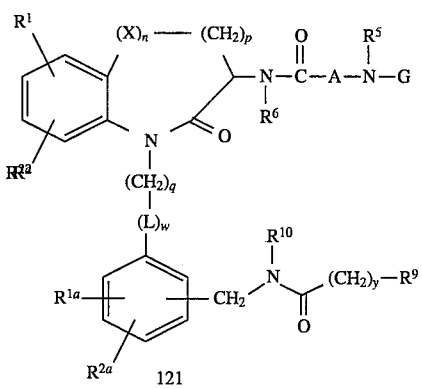
121
G is benzyloxycarbonyl

A useful preparation of the protected benzylamine intermediate 125 is shown in Scheme 37. Metallation of 4-bromobenzyl t-butyldimethylsilylether 84 with n-butyllithium followed by treatment with trimethyl borate gives the aryl boronic acid 122. Reaction of 122 with 2-bromo-N-(t-butoxycarbonyl)-benzylamine 123 in the presence of tetrakis(triphenyl-phosphine)palladium(0) and barium hydroxide in aqueous 1,2-dimethoxyethane at elevated temperature gives the coupled product 124 in good yield. Desilylation and conversion to the O-methanesulfonate 125 is achieved using the conditions described in Scheme 24. Reaction of 125 with compounds of formula V is carried out using the conditions described in Scheme 13.

SCHEME 37

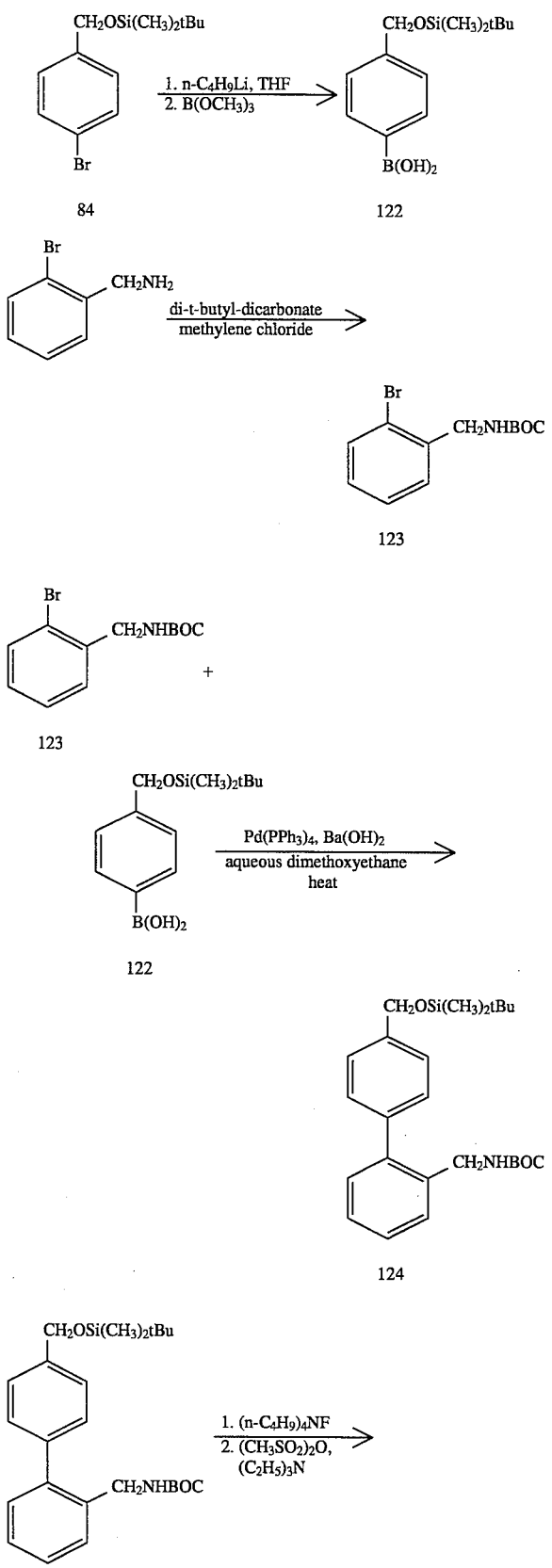

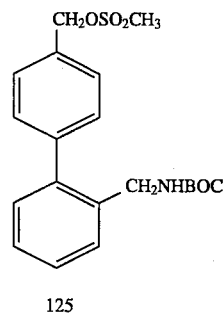

Compounds of formula I wherein $R^{3a}$ or $R^{3b}$ is a (4,5-dihydro-2-oxazolyl)amino group are prepared from isocyanate 106 as demonstrated in Scheme 38. Reaction of 106 with ethanolamine in methylene chloride gives the hydroxyethyl urea 126 in high yield. Treatment of 126 with methanesulfonyl chloride and triethylamine in methylene chloride in the presence of 4-dimethyl-aminopyridine leads to the (4,5-dihydro-2-oxazolyl)-amino product 127 in fair yield.

SCHEME 38

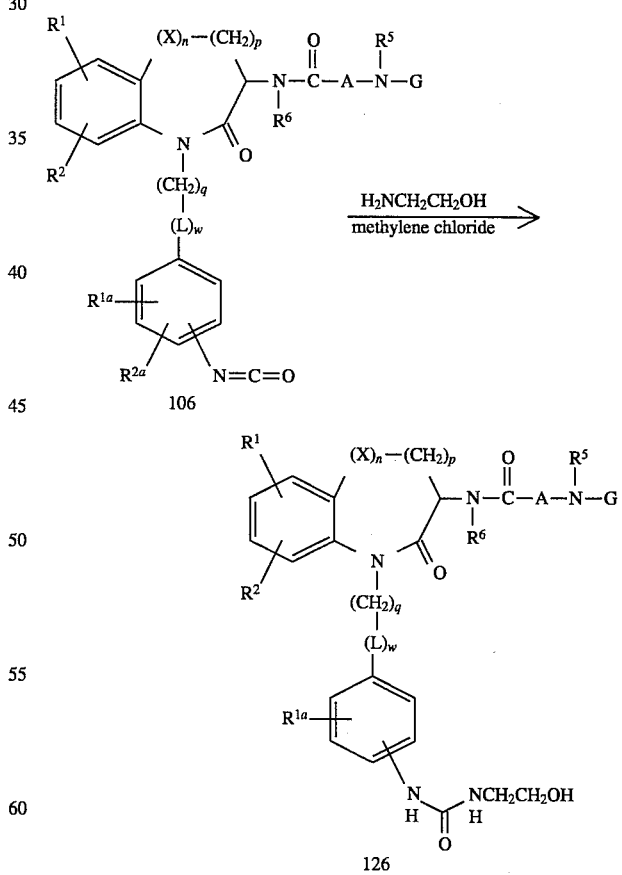

63
-continued
SCHEME 38

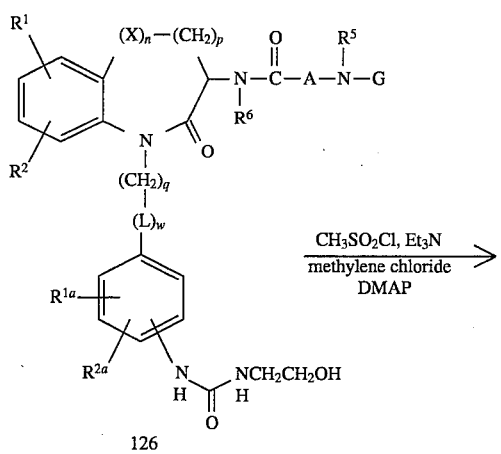

126

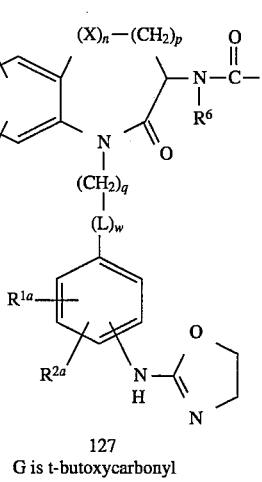

127
G is t-butoxycarbonyl

The six-membered ring analogs of 127 can also be prepared from isocyanate 106 by the procedure of Y. Iwakura, et al, J. Org. Chem., 30, 3410 (1965). As shown in Scheme 39, reaction of isocyanate 106 with azetidine in methylene chloride will give the urea product 128. Rearrangement of 128 through the use of picric acid in boiling toluene leads to the desired product 129.

SCHEME 39

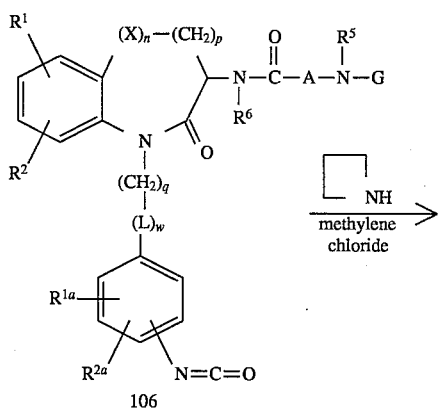

106

64
-continued
SCHEME 39

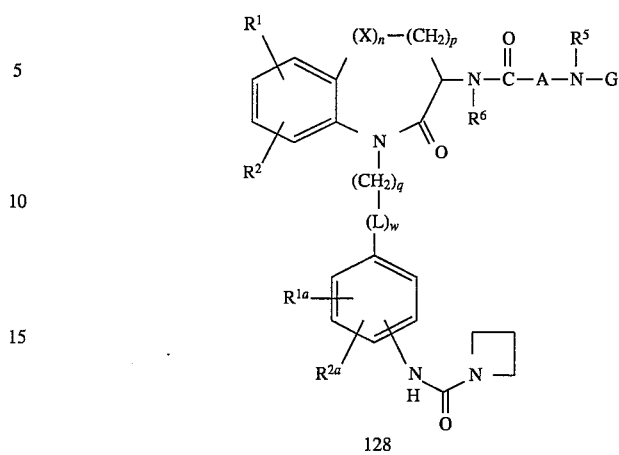

128

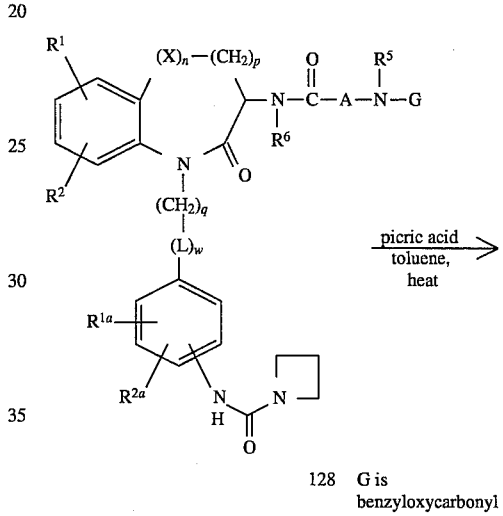

128  G is benzyloxycarbonyl

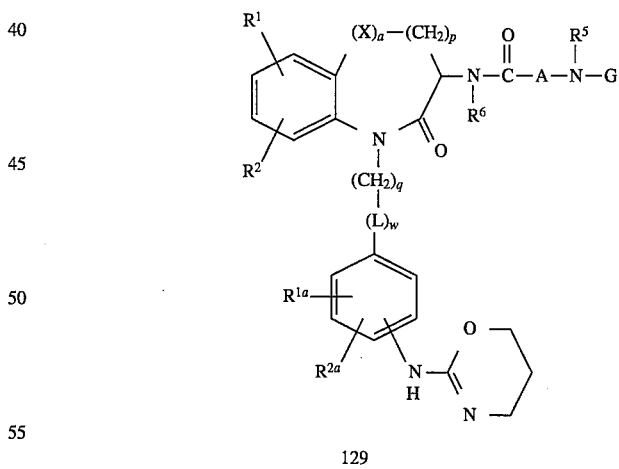

129

Compounds of formula I wherein $R^{3a}$ or $R^{3b}$ is a (4,5-dihydro-2-imidazolyl)amino group can be prepared from amine 52 as demonstrated in Scheme 40. Formation of the isothiocyanate 130 by treatment with thiocarbonyldiimidazole, followed by reaction with ethylenediamine will give the intermediate aminoethyl urea 131. Thermal rearrangement of 131 in an inert solvent will give the desired (4,5-dihydro-2-imidazolyl)amino compound 132.

SCHEME 40
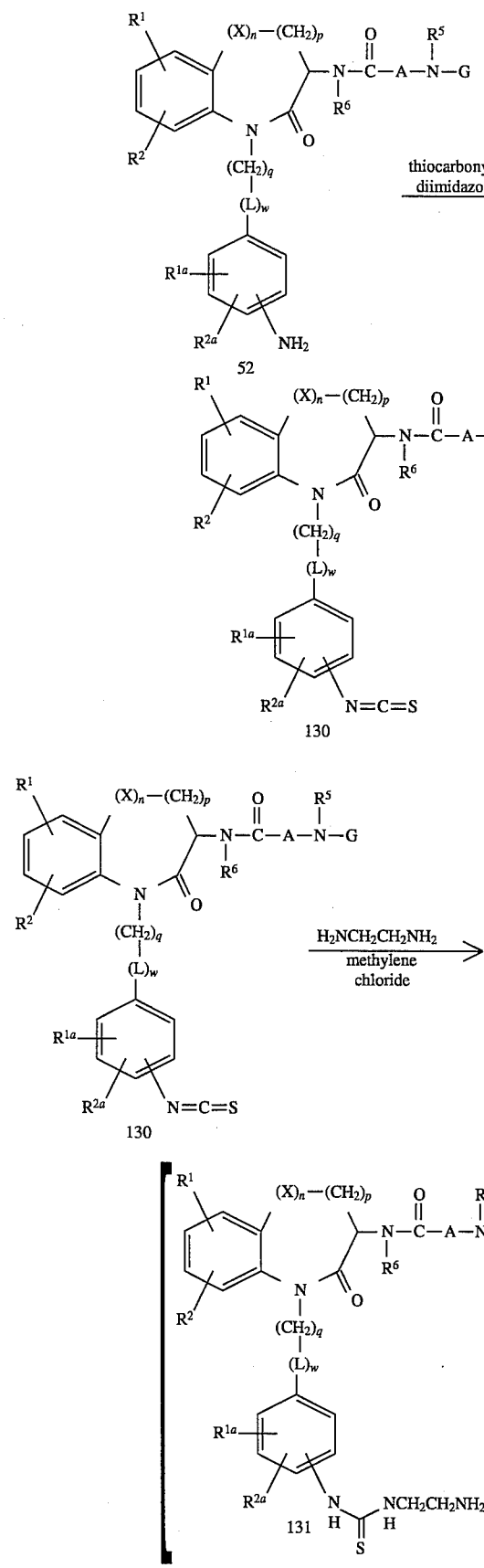
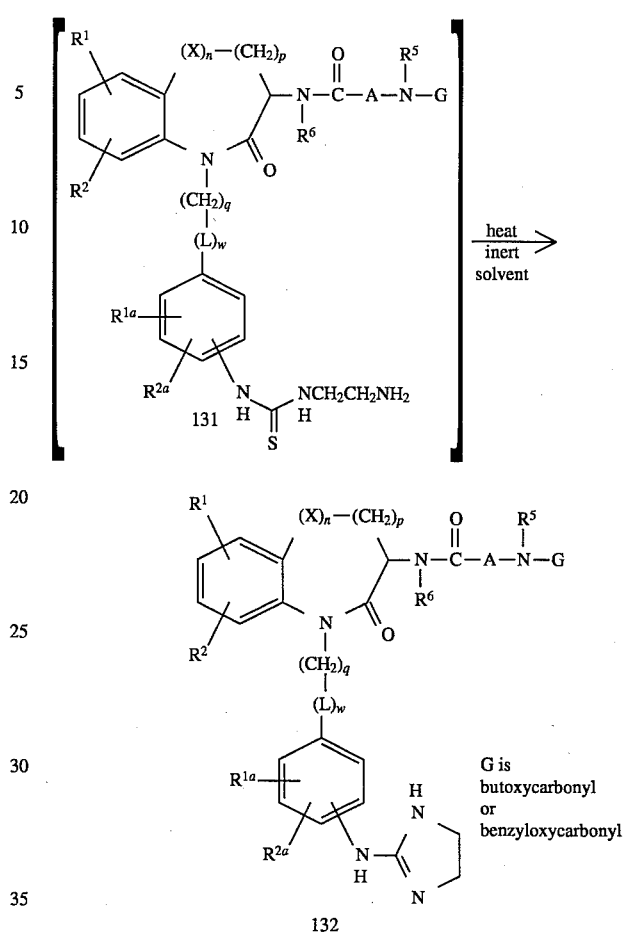
G is butoxycarbonyl or benzyloxycarbonyl
Conversion to the final products of formula I wherein $R^4$ is hydrogen, is carried out by simultaneous or sequential removal of all protecting groups from intermediate VII as illustrated in Scheme 41.
SCHEME 41
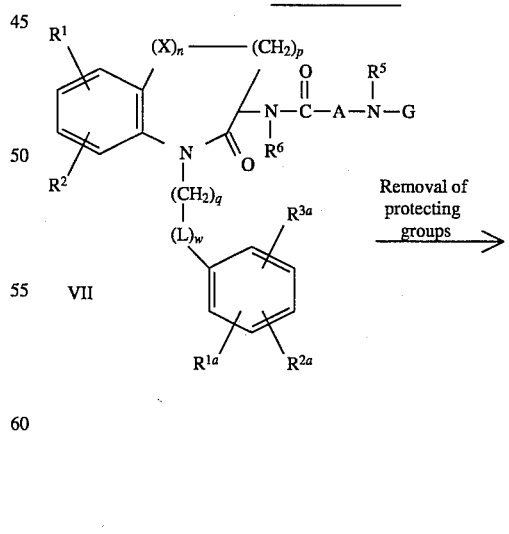

-continued
SCHEME 41

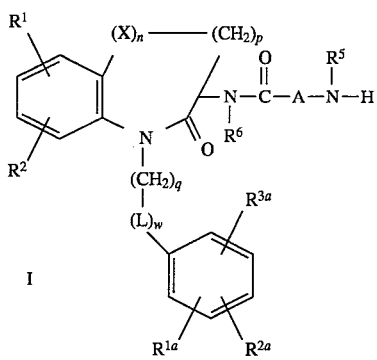

I

Removal of benzyloxycarbonyl groups can be achieved by a number of methods known in the art; for example, catalytic hydrogenation with hydrogen in the presence of a platinum or palladium catalyst in a protic solvent such as methanol. In cases where catalytic hydrogenation is contraindicated by the presence of other potentially reactive functionality, removal of benzyloxycarbonyl groups can also be achieved by treatment with a solution of hydrogen bromide in acetic acid. Removal of t-butoxycarbonyl (BOC) protecting groups is carried out by treatment of a solution in a solvent such as methylene chloride or methanol, with a strong acid, such as hydrochloric acid or trifluoroacetic acid. Conditions required to remove other protecting groups which may be present can be found in *Protective Groups in Organic Synthesis* T. W. Greene, John Wiley & Sons, NY, 1981.

Compounds of formula I wherein $R^4$ and $R^5$ are each hydrogen can be further elaborated by reductive alkylation with an aldehyde by the aforementioned procedures or by alkylations such as by reaction with various epoxides. The products, obtained as hydrochloride or trifluoroacetate salts, are conveniently purified by reverse phase high performance liquid chromatogrphy (HPLC) or by recrystallization.

It is noted that the order of carrying out the foregoing reaction schemes is not significant and it is within the skill of one skilled in the art to vary the order of reactions to facilitate the reaction or to avoid unwanted reaction products.

The growth hormone releasing compounds of Formula I are useful in vitro as unique tools for understanding how growth hormone secretion is regulated at the pituitary level. This includes use in the evaluation of many factors thought or known to influence growth hormone secretion such as age, sex, nutritional factors, glucose, amino acids, fatty acids, as well as fasting and non-fasting states. In addition, the compounds of this invention can be used in the evaluation of how other hormones modify growth hormone releasing activity. For example, it has already been established that somatostatin inhibits growth hormone release. Other hormones that are important and in need of study as to their effect on growth hormone release include the gonadal hormones, e.g., testosterone, estradiol, and progesterone; the adrenal hormones, e.g., cortisol and other corticoids, epinephrine and norepinephrine; the pancreatic and gastrointestinal hormones, e.g., insulin, glucagon, gastrin, secretin; the vasoactive intestinal peptides, e.g., bombesin; and the thyroid hormones, e.g., thyroxine and triidothyronine. The compounds of Formula I can also be employed to investigate the possible negative or positive feedback effects of some of the pituitary hormones, e.g., growth hormone and endorphin peptides in the pituitary to modify growth hormone release. Of particular scientific importance is the use of these compounds to elucidate the subcellular mechanisms mediating the release of growth hormone.

The compounds of Formula I can be administered to animals, including man, to release growth hormone in vivo. For example, the compounds can be administered to commercially important animals such as swine, cattle, sheep and the like to accelerate and increase their rate and extent of growth, and to increase milk production in such animals. In addition, these compounds can be administered to humans in vivo as a diagnostic tool to directly determine whether the pituitary is capable of releasing growth hormone. For example, the compounds of Formula I can be administered in vivo to children. Serum samples taken before and after such administration can be assayed for growth hormone. Comparison of the amounts of growth hormone in each of these samples would be a means for directly determining the ability of the patient's pituitary to release growth hormone.

Accordingly, the present invention includes within its scope pharmaceutical compositions comprising, as an active ingredient, at least one of the compounds of Formula I in association with a pharmaceutical carrier or diluent. Optionally, the active ingredient of the pharmaceutical compositions can comprise a growth promoting agent in addition to at least one of the compounds of Formula I or another composition which exhibits a different activity, e.g., an antibiotic or other pharmaceutically active material.

Growth promoting agents include, but are not limited to, TRH, diethylstilbesterol, theophylline, enkephalins, E series prostaglandins, compounds disclosed in U.S. Pat. No. 3,239,345, e.g., zeranol, and compounds disclosed in U.S. Pat. No. 4,036,979, e.g., sulbenox or peptides disclosed in U.S. Pat. No. 4,411,890.

A still further use of the disclosed novel benzo-fused lactam growth hormone secretagogues is in combination with other growth hormone secretagogues such as GHRP-6, GHRP-1 as described in U.S. Pat. Nos. 4,411,890; and publications WO 89/07110 and WO 89/07111 and B-HT920 or growth hormone releasing factor and its analogs or growth hormone and its analogs or somatomedins including IGF-1 and IGF-2.

A still further use of the instant novel benzo-fused lactam growth hormone secretagogues is in combination with a $_2$-adrenergic agonists in the treatment of obesity (see U.S. Pat. No. 5120713) or in combination with a parathyroid hormone in the treatment of osteoporosis (see WO 92/09304).

As is well known to those skilled in the art, the known and potential uses of growth hormone are varied and multitudinous. Thus, the administration of the compounds of this invention for purposes of stimulating the release of endogenous growth hormone can have the same effects or uses as growth hormone itself. These varied uses of growth hormone may be summarized as follows: stimulating growth hormone release in elderly humans; Prevention of catabolic side effects of glucocorticoids, treatment of osteoporosis, stimulation of the immune system, treatment of retardation, acceleration of wound healing, accelerating bone fracture repair, treatment of growth retardation, treating renal failure or insufficiency resulting in growth retardation, treatment of physiological short stature, including growth hormone deficient children, treating short stature associated with chronic illness, treatment of obesity and growth retardation associated with obesity, treating growth retardation associated with Prader-Willi syndrome and Turner's syndrome; Accelerating the recovery and reducing hospitalization of burn patients; Treatment of intrauterine growth retardation, skeletal dysplasia, hypercortisolism and Cushings syndrome; Induction of pulsatile growth hormone release; Replacement of growth hormone in stressed patients; Treatment of osteochondrodysplasias, Noonans syndrome, schizophrenia, depression, Alzheimer's disease, delayed wound healing, and psychosocial deprivation; treatment of pulmonary dysfunction and ventilator dependency; Attenuation of protein catabolic response after a major operation; reducing cachexia and protein loss due to chronic illness such as cancer or AIDS. Treatment of hyperinsulinemia including nesidioblastosis; Adjuvant treatment for ovulation induction; To stimulate thymic development and prevent the age-related decline of thymic function; Treatment of immunosuppressed patients; Improvement in muscle strength, mobility maintenance of skin thickness, metabolic homeostasis, renal hemeostasis in the frail elderly; Stimulation of osteoblasts, bone remodelling, and cartilage growth; Stimulation of the immune system in companion animals and treatment of disorders of aging in companion animals; Growth promotant in livestock; and stimulation of wool growth in sheep.

The compounds of this invention can be administered by oral, parenteral (e.g., intramuscular, intraperitoneal, intravenous or subcutaneous injection, or implant), nasal, vaginal, rectal, sublingual, or topical routes of administration and can be formulated in dosage forms appropriate for each route of administration.

Solid dosage forms for oral administration include capsules, tablets, pills, powders and granules. In such solid dosage forms, the active compound is admixed with at least one inert pharmaceutically acceptable carrier such as sucrose, lactose, or starch. Such dosage forms can also comprise, as is normal practice, additional substances other than inert diluents, e.g., lubricating agents such as magnesium stearate. In the case of capsules, tablets and pills, the dosage forms may also comprise buffering agents. Tablets and pills can additionally be prepared with enteric coatings.

Liquid dosage forms for oral administration include pharmaceutically acceptable emulsions, solutions, suspensions, syrups, the elixirs containing inert diluents commonly used in the art, such as water. Besides such inert diluents, compositions can also include adjuvants, such as wetting agents, emulsifying and suspending agents, and sweetening, flavoring, and perfuming agents.

Preparations according to this invention for parenteral administration include sterile aqueous or non-aqueous solutions, suspensions, or emulsions. Examples of non-aqueous solvents or vehicles are propylene glycol, polyethylene glycol, vegetable oils, such as olive oil and corn oil, gelatin, and injectable organic esters such as ethyl oleate. Such dosage forms may also contain adjuvants such as preserving, wetting, emulsifying, and dispersing agents. They may be sterilized by, for example, filtration through a bacteria-retaining filter, by incorporating sterilizing agents into the compositions, by irradiating the compositions, or by heating the compositions. They can also be manufactured in the form of sterile solid compositions which can be dissolved in sterile water, or some other sterile injectable medium immediately before use.

Compositions for rectal or vaginal administration are preferably suppositories which may contain, in addition to the active substance, excipients such as cocoa butter or a suppository wax.

Compositions for nasal or sublingual administration are also prepared with standard excipients well known in the art.

The dosage of active ingredient in the compositions of this invention may be varied; however, it is necessary that the amount of the active ingredient be such that a suitable dosage form is obtained. The selected dosage depends upon the desired therapeutic effect, on the route of administration, and on the duration of the treatment. Generally, dosage levels of between 0.0001 to 100 mg/kg. of body weight daily are administered to patients and animals, e.g., mammals, to obtain effective release of growth hormone.

The following examples are provided for the purpose of further illustration only and are not intended to be limitations on the disclosed invention.

EXAMPLE 1

3-Amino-3-methyl-N-[2,3,4,5-tetrahydro-2-oxo-1-[[2'-(1H-imidazol-2-yl)[(1,1'-biphenyl]-4-yl]methyl]-1H-1-benzazepin-3(R)-yl]-butanamide, di(trifluoroacetate)

Step A: 1-Tetralone oxime

To 4.6 L of water at room temperature in a 4-neck 50 L flask sitting in a steam bath apparatus equipped with an overhead stirrer, a temperature probe and reflux condenser was added 3.72 Kg (27.36 mol) of sodium acetate with stirring, followed by 1.9 Kg of hydroxylamine hydrochloride (27.36 mol). To this slurry at room temperature, 12 L of ethanol was added followed by 1.994 Kg (13.68 mol) of 1-tetralone. Additional ethanol (1.7 L) was used to rinse off the funnel and added to the reaction mixture. The resulting light orange slurry was heated to 75° C. over 40 minutes and maintained at 75°–85° C. for another 75 minutes. The reaction mixture was cooled with the aid of ice packed around the flask. When the internal temperature reached 32° C., the reaction mixture was pumped over 15 minutes into 60 L of ice contained in a 200 L vessel. The reaction vessel was washed with an additional 2 L of water which was added to the 200 L vessel. When the ice melted, the mixture was filtered through a filter pad and the wet cake washed with 4 L of water. The wet cake was suction dried for 1 hour then transferred to two trays and dried under vacuum at 40° C. for 2 days to give 2.094 Kg (13.01 mol, 95%) of product, $^1$H NMR (250 MHz, CDCl$_3$): 1.90 (m, 2H), 2.80 (t, 6 Hz, 2H), 2.88 (t, 6 Hz, 2H), 7.15–7.35 (m, 3H), 7.90 (d, 8 Hz, 1H), 8.9 (br s, 1H).

Step B: 2,3,4,5-Tetrahydro-1H-1-benzazepin-2-one

To 10 L of methanesulfonic acid in a 22 L 3-neck flask equipped with an overhead stirrer, a temperature probe, nitrogen inlet and reflux condenser was added 2.6 Kg (18.61 mol) of phosphorus pentoxide. An additional 1.6 L of methansulfonic acid was used to wash all the phosphorus pentoxide into the vessel. The mixture was heated at 90° C. for 2.5 hours then cooled to 50° C. using an ice bath and treated with 2.00 Kg (12.41 mol) of 1-tetralone oxime in several portions over 15 minutes. The mixture was heated at 63° C. for 10 minutes then slowly heated to 80° C. and kept at 80° C. for 3 hours. The reaction mixture was pumped into 70 L of ice then treated slowly with 11.25 L of 50% aqueous sodium hydroxide over 90 minutes at such a rate so as to maintain the temperature below 28° C. The mixture was filtered and 4 L of the filtrate was used to rinse the vessel. The wet cake (pink) was washed with 8 L of water then suction dried for 45 minutes then transferred to two trays and dried under vacuum at 40° C. for 2 days to give 1.9 Kg (11.79 mol, 95%) of product, $^1$H NMR (250 MHz, CDCl$_3$): 2.24 (m, 2H), 2.38 (t, 6 Hz, 2H), 2.82 (t, 6 Hz, 2H), 7.03 (d, 8 Hz, 1H), 7.13 (m, 1H), 7.24 (m, 2H), 8.63 (br s, 1H).

Step C: 3-Iodo-2,3,4,5-tetrahydro-1H-1-benzazepin-2-one

A suspension of 1.8 Kg (11.17 mol) of 2,3,4,5-tetrahydro-1H-1-benzazepin-2-one in a mixture of 22.33 L of methylene chloride and 11.78 L (55.83 mol) of hexamethyldisilazane was heated at reflux for 10 minutes then cooled to 30° C. and treated with 8.503 Kg (33.5 mol) of iodine in one portion. The mixture was heated at reflux for 2.5 hours then cooled to room temperature. Aqueous sodium sulfite containing 4.926 Kg of sodium sulfite in 44 L of water was cooled to 0° C. and into it was poured the reaction mixture in several portions with vigorous stirring while maintaining the temperature below 10° C. The reaction vessel was rinsed with 22.33 L of methylene chloride and the washing transferred to the quenching mixture. The quenching mixture was stirred vigorously and the layers allowed to separate. The aqueous layer was removed and reextracted with 22.33 L of methylene chloride. The combined organic layers were washed with 11 L of water and concentrated under vacuum to a final volume of /5 L. The residue was treated with 55 L of toluene and concentrated under vacuum to a final volume of 10 L. The resulting slurry was removed by filtration and the filter cake washed with an additional 5 L of toluene and dried under vacuum at ambient temperature for 24 hours to give 1.842 Kg (6.42 mol. 57%) of product. $^1$H NMR (200 MHz, CDCl$_3$): 2.6–2.8 (m,3H), 2.93 m, 1H), 4.64 (t, 8 Hz, 1H), 6.97 (d, 8 Hz, 1H), 7.10–7.35 (m, 3H), 7.55 (br s, 1H).

Step D: 3(R)-Amino-2,3,4,5-tetrahydro-1H-1-benzazepin-2-one, D-tartaric acid salt 3-Iodo-2,3,4,5-tetrahydro-1H-1-benzazepin-2-one (1.79 Kg, 6.24 mol) was slurried in 6.2 L of methanol and the slurry charged into an autoclave. Condensed ammonia (1.55 L) was added and the autoclave closed, with stirring, and heated to 100° C. over 1 hour. Heating at 100° C. was continued for 2 hours then the autoclave was allowed to cool to room temperature over 1 hour, during which time the internal pressure was 150–155 psi. The reaction mixture was transferred to a polyethylene jug and the autoclave rinsed with 2×8 L of methanol. The washings were concentrated under vacuum at 30° C. then combined with the reaction mixture and concentrated to near dryness under vacuum at 30° C. The resulting residue was dissolved in 4 L of ethyl acetate then concentrated to dryness under vacuum at 30° C.

Sodium chloride (712 g) was dissolved in 2 L of water and 1.0 Kg of sodium carbonate was dissolved in 6 L of water. Two liters of the sodium carbonate solution was added to the concentrated residue and the resulting slurry transferred to an extraction flask. Another 2 L portion of the sodium carbonate solution was added to the residue flask and the solution transferred to the extraction flask. The remaining sodium carbonate solution was used in the same way. The sodium chloride solution was added to the sodium carbonate/aminolactam emulsion and the resulting mixture stirred for 10 minutes then extracted with four 6 L portions of methylene chloride. The combined methylene chloride layers were concentrated to dryness; the residue was treated with 2 L of 200 proof ethanol and the resulting slurry concentrated to dryness under vacuum to give 1.171 Kg of crude product.

The crude product was slurried in 8 L of ethanol and treated with 900 g of D-tartaric acid in one portion. Water (7 L) was added and the mixture heated to 77° C., then additional ethanol (45 L) was added and heating continued. The solution was cooled to 43° C. and treated with the seed slurry. (The seed slury was prepared by the route described above starting with 10.50 g of crude product and 9.1 g of D-tartaric acid.) The solution was aged at room temperature for 48 hours. The slurry formed was removed by filtration and the wet cake washed with 1.8 L of ethanol. The resulting filter cake was suction dried with nitrogen bleeding for 20 hours then transferred into a drying tray and dried under vacuum for 24 hours to give 354 g (1.085 mol, 17.4%) of the product. $^1$H NMR (250 MHz, CDCl$_3$); 2.13 (m, 1H), 2.51 (m, 2H), 2.73 (m, 2H), 3.68 (t, 6 Hz, 1H), 3.98 (s, 2H), 7.05 (d, 8 Hz, 1H), 7.16 (t, 8 Hz), 1H), 7.30 (m, 2H), 7.6 (br s, 5H), 10.26 (br s, 1H).

Step E: 3(R)-Amino-2,3,4,5-tetrahydro-1H-1-benzazepin-2-one

A Solution of 229.23 g (0.700 mol) of 3(R)-amino-2,3,4,5-tetrahydro-1H-1-benzazepin-2-one, D-tartrate in 4.1 L of water was treated with 194 g (1.40 mol) of potassium carbonate. Subsequent portions of 100 g and 135 g of potassium carbonate were added until the pH was 10.5. The mixture was extracted with four 4 L portions of methylene chloride which were then combined and dried over magnesium sulfate. The aqueous layer was treated with 1.4 Kg of sodium chloride and reextracted with four 4 L portions of methylene chloride which were then combined and dried over magnesium sulfate. The two 16 L batches of extracts were combined, filtered and concentrated to dryness under vacuum to give 115.5 g of product which contained 1.6% of an impurity identified as 7-iodo-3(R)-amino-2,3,4,5-tetrahydro-1H-1-benzazepin-2-one.

A solution of 107.02 g (0.607 mol) of the intermediate obtained above in 1.712 L of ethanol was hydrogenated at room temperature and 40 psi over 4.00 g of 10% palladium on carbon for 4 hours. The catalyst was removed by filtration through solkaflok and the filtrate concentrated to dryness under vacuum to give 101.08 g (0.574 mol, 94.4%) of product.

Step F: 4,4-Dimethylazetidin-2-one

A 3-neck 3 L round bottom flask equipped with a magnetic stirrer, thermometer, cold finger condenser and nitrogen bubbler was charged with 1 L of ether. The flask was cooled to −65° C. and into it was condensed 500–600 mL of isobutylene. The cold finger condenser was replaced with a dropping funnel and 200 mL (325 g, 2.30 mol) of chlorosulfonyl isocyanate was added dropwise over 1.5 hours. The mixture was maintained at −65° C. for 1.5 hours then the dry ice/acteone cooling bath replaced with methanol/ice and the internal temperature slowly increased to −5° C. at which time the reaction initiated and the internal temperature rose to 15° C. with evolution of gas. The internal temperature remained at 15° C. for several minutes then dropped back down to −5° C. and the mixture stirred at −5° C. for 1 hour. The methanol/ice bath was removed and the reaction mixture warmed to room temperature and stirred overnight.

The reaction mixture was transferred to a 3-neck 12 L round bottom flask fitted with a mechanical stirrer and diluted with 2 L of ether. The well stirred reaction mixture was treated with 2 L of saturated aqueous sodium sulfite. After 1 hour, an additional 1 L of saturated aqueous sodium sulfite was added followed by sufficient sodium bicarbonate to adjust the pH to approximately 7. The mixture was stirred another 30 minutes then the layers allowed to separate. The ether layer was removed and the aqueous layer reextracted with 2×1 L of ether. The combined ether extracts were washed once with 500 mL of saturated aqueous sodium bicarbonate and once with 500 mL of saturated aqueous sodium chloride. The ether layer was removed, dried over magnesium sulfate, filtered and concentrated under vacuum to give 33 g of a pale yellow oil. The aqueous layer was made basic by the addition of solid sodium bicarbonate and extracted with 3×1 L of ether. The combined ether extracts were washed and dried as described above, then combined with the original 33 g of pale yellow oil and concentrated under vacuum to give 67.7 g of product. Further extraction of the aqueous layer with 4×1 L of methylene chloride and washing and drying as before gave an additional 74.1 g of product. Still further extraction of the aqueous layer with 4×1 L of methylene chloride gave an additional 21.9 g of product. The combined product (163.7 g, 1.65 mol, 72%) was used in Step G without purification. $^1$H NMR (200

MHz, CDCl$_3$): 1.45 (s, 6H), 2.75 (d, 3 Hz, 2H), 5.9 (br s, 1H).

Step G: N-(t-Butoxycarbonyl)-4,4-dimethylazetidin-2-one

A 5 L, 3-neck round bottom flask equipped with a magnetic stirrer, thermometer, nitrogen bubbler and addition funnel was charged with 88.2 g (0.89 mol) of 4,4-dimethylazetidin-2-one (Step F), 800 mL of methylene chloride, 150 mL of triethylamine (1.08 mol) and 10.9 g (0.089 mol) of 4-dimethylaminopyridine. To the stirred solution at room temperature was added dropwise over 15 minutes a solution of 235 g (1.077 mol) of di-t-butyl-dicarbonate in 300 mL of methylene chloride. The reaction mixture was stirred at room temperature overnight then diluted with 1 L of methylene chloride and washed with 500 mL of saturated aqueous ammonium chloride, 500 mL of water, and 500 mL of saturated aqueous sodium chloride. The organic layer was separated, dried over magnesium sulfate, filtered and concentrated under vacuum to afford 180.3 g of crude product as an organic solid. The material was used directly in Step H without purification. $^1$H NMR 200 MHz, CDCl$_3$): 1.50 (s, 9H), 1.54 (s, 6H), 2.77 (s, 2H). Step H: 3-t-Butoxycarbonylamino-3-methylbutanoic acid A 3 L, 3-neck round bottom flask equipped with a magnetic stirrer, thermometer, nitrogen bubbler and addition funnel was charged with 180.3 g (0.89 mol) of N-(t-butoxycarbonyl)-4,4-dimethylazetidin-2-one dissolved in 1 L of tetrahydrofuran. The solution was cooled to 0°–5° C. and treated dropwise with 890 mL of 1.0M aqueous lithium hydroxide over 30 minutes. The reaction mixture was stirred at 0°–5° C. for 2 hours then diluted with 1 L of ether and 1 L of water. The layers were allowed to separate and the aqueous layer reextracted with an additional 1 L of ether. The aqueous layer was acidified by the addition of 1 L of saturated aqueous sodium bisulfate, then extracted with 1×1 L and 2×500 mL of ether. The combined organic layer and ether extracts were washed with 500 mL of saturated aqueous sodium chloride, dried over magnesium sulfate and concentrated under vacuum to 173 g of a yellow oil that solidified upon standing. The material was slurried with warm hexane then filtered and dried under high vacuum to afford 168.5 g (0.775 mol, 87%) of product as a white solid. $^1$H NMR (200 MHz, CDCl$_3$): 1.39 (s, 6H), 1.44 (s, 9H), 2.72 (s, 2H). FAP-MS calculated for C$_{10}$H$_{19}$NO$_4$ 217; found 218 (M+H, 54%).

Step I: 3-t-Butoxycarbonylamino-3-methyl-N-[2,3,4,5-tetrahydro-2-oxo-1H-1-benzazepin-3(R)-yl]-butanamide A solution of 8.70 g (49.4 mmol) of 3(R)-amino-2,3,4,5-tetrahydro-1H-1-benzazepin-2-one (Step E) in 100 mL of methylene chloride was treated with 10.73 g (49.4 mmol) of 3-t-butoxycarbonylamino-3-methylbutanoic acid (Step H) and 13.8 mL of triethylamine (10.0 g, 99 mmol, 2 eq.). The reaction flask was immersed in an ambient temperature water bath then 26 g of benzotriazol-1-yloxytris(dimethylamino) phosphonium hexafluorophosphate (59 mmol, 1.2 eq) was added all at once and the mixtrue stirred at room temperature for 2 hours. The reaction mixture was added to 300 mL of ethyl acetate and washed three times with 5% aqueous citric acid, twice with saturated aqueous sodium bicarbonate and once with saturated aqueous sodium chloride. The organic layer was removed, dried over magnesium sulfate, filtered and the filtrate concentrated under vacuum. The residue was purified by preparative high pressure liquid chromatography on silica, eluting with ethyl acetate/hexane (4:1), to afford 17.42 g (46.4 mmol, 94%) of the product as a white solid. $^1$H NMR (200 MHz, CDCl$_3$): 1.37 (s,6H), 1.44 (s,9H), 1.95 (m,1H), 2.46 (d, 15 Hz, 1H), 2.59 (d, 15 Hz, 1H), 2.6–3.0, (m,3H), 4.53 (m,1H), 5.30 (br s, 1H), 6.72 (d, 7 Hz, 1H), 6.98 (d, 8 Hz, 1H), 7.1–7.3 (m,3H), 7.82 (br s, 1H), FAB-MS: calculated for C$_{20}$H$_{29}$N$_3$O$_4$375; found 376 (M+H, 70%).

Step J: 4-(t-Butyldimethylsiloxymethyl)bromobenzene

A solution of 26.28 g (0.141 mol) of 4-bromobenzyl alcohol and 19.1 g (0.28 mol) of imidazole in 100 mL of methylene chloride was treated dropwise with a solution of 21.18 g (0.14 mol) of t-butyldimethylsilyl chloride in 50 mL of methylene chloride. The reaction mixture was stirred at room temperature for 30 minutes then transferred to a separatory funnel and washed with water, 1N hydrochloric acid, saturated aqueous sodium bicarbonate and saturated aqueous sodium chloride. The organic layer was removed, dried over magnesium sulfate, filtered and solvents removed under vacuum giving 41 g of the product as a colorless, viscous oil. $^1$H NMR (200 MHz, CDCl$_3$): 0.09 (s, 6H), 0.93 (s, 9H), 4.67 (s, 2H), 7.18 (d, 8 Hz, 2H), 7.43 (d, 8 Hz, 2H).

Step K: 1-(4-Toluenesulfonyl)-2-(2-bromophenyl) imidazole

A solution of 2.50 g (11.6 mmol ) of 2-(2-bromophenyl)imidazole in 10 mL of methylene chloride was treated with 1.9 mL of triethylamine (13.8 mmol), 2.64 g (13.8 mmol) of p-toluenesulfonyl chloride and 100 mg of 4-dimethylaminopyridine. The reaction mixture was stirred at room temperature for 15 minutes then transferred to a separatory funnel and washed with water, 5% aqueous citric acid, saturated aqueous sodium bicarbonate and saturated aqueous sodium chloride. The organic layer was removed, dried over magnesium sulfate, filtered and solvents removed under vacuum. The crude product was chromatographed on silica, eluting with hexane/ethyl acetate (1:1), to give 4.16 g (11.0 mmol 95%) of the product which was recrystallized from hexane. FAB-MS: calculated for C$_{16}$H$_{13}$BrN$_2$O$_2$S 376, 378; found 377,379 (M+H, 50%). $^1$H NMR (200 MHz, CDCl$_3$): 2.32 (s, 3H), 7.09 (d, 2 Hz, 1H), 7.12 (d, 8 Hz, 2H), 7.28 (m, 5H), 7.46 (m, 1H), 7.57 (d, 2 Hz, 1H).

Step L: 1-(4-Toluenesulfonyl)-2-[4'-(t-butyldimethylsiloxymethyl)-1,1'-biphen-2-yl]imidazole A solution of 1.50 g (5.0 mmol) of 4-(t-butyl-dimethylsiloxymethyl) bromobenzene in 10 mL of dry tetrahydrofuran under a nitrogen atmosphere was cooled to −15° C. and treated with 5.88 mL of 1.7M (10.0 mmol) t-butyllithium in hexane slowly over several minutes. The mixture was stirred at −15° C. for one hour over which time it slowly turned green. A solution of anhydrous zinc chloride in ether (5.0 mL of 1.7M solution; 5.0 mmol; pre-treated with 0.5 mL of 1.7M t-butyllithium to remove traces of water) was added and the reaction mixture warmed to room temperature. In a separate flask, 1.68 g (5.0 mmol) of 1-(4-toluenesulfonyl)-2-(2-bromophenyl)imidazole and 98 mg (0.15 mmol) of bis(triphenylphosphine)nickel(II) chloride were dissolved in 10 mL of dry tetrahydrofuran and the solution cooled to 0° C. and treated with 0.10 mL of 3M methylmagnesium bromide in ether. This solution was then added by cannula to the original solution containing the zinc reagent and the resulting mixture stirred at room temperature for three hours. The reaction was treated with 10 mL of dilute aqueous acetic acid, then extracted several times with ethyl acetate. The combined extracts were dried over magnesium sulfate, filtered and solvents removed under vacuum to give 3.5 g of a brown oil which was chromatographed on silica, eluting wth hexane/ethyl acetate (1:1) giving 1.15 g (2.22 mmol, 44%) of the product. FAB-MS: calculated for C$_{29}$H$_{34}$N$_2$O$_3$Ssi 518; found 519 (M+H, 23%). $^1$H NMR (200 MHz, CDCl$_3$): 0.09 (s, 6H), 0.94 (s, 9H), 2.37 (s, 3H), 4.70 (s, 2H), 6.94 (d, 8 Hz, 2H), 6.98 (d, 2 Hz, 1H), 7.13 (m, 5H), 7.30 (m, 3H), 7.4–7.6 (m, 3H).

Step M: 1-(4-Toluenesulfonyl)-2-[4'-(hydroxymethyl)-1,1'-biphen-2-yl]imidazole

A solution of 313 mg (0.60 mmol) of the intermediate obtained in Step L in 2 mL of dry tetrahydrofuran at 0° under a nitrogen atmosphere was treated with 190 mg (0.60 mmol) of tetrabutylammonium fluoride trihydrate and the mixture stirred at 0° C. for 90 minutes. Saturated aqueous sodium bicarbonate (2 mL) was added and the mixture extracted several times with methylene chloride. The combined extracts were dried over magnesium sulfate, filtered and solvents removed under vacuum giving 220 mg of residue. Chromatography on silica, eluting with hexane/ethyl acetate (1:1), gave 96 mg (0.24 mmol, 40%) of the product as a colorless oil. $^1$H NMR (200 MHz, CDCl$_3$): 2.36 (s, 3H), 4.57 (s, 2H), 6.95 (m, 3H), 7.12 (m, 5H), 7.29 (m, 3H), 7.40 (m, 2H), 7.51 (m, 1H).

Step N: 1-(4-Toluenesulfonyl)-2-[4'-(methyanesulfonyl-oxymethyl)-1,1'-biphen-2-yl]imidazole A solution of 45 mg (0.11 mmol) of the intermediate obtained in Step M in 2 mL of methylene chloride at room temperature under a nitrogen atmosphere was treated with 0.03 mL of triethylamine (0.22 mmol) followed by 19 mg (0.11 mmol) of methanesulfonic anhydride. The mixture was stirred at room temperature for 2.5 hours. The reaction mixture was washed with water and saturated aqueous sodium chloride, then dried over magnesium sulfate, filtered and solvents removed under vacuum giving 49 mg of crude product which was used in the next step without purification.

Step O: 3-t-Butoxycarbonylamino-3-methyl-N-[2,3,4,5-tetrahydro-2-oxo-1-[[2'-[1-(4-toluenesulfonyl) imidazol-2-yl][1,1'-biphenyl]-4-yl]methyl]-1H-1-benzazepin-3(R)-yl]-butanamide A solution of 37 mg (0.10 mmol) of 3-t-butoxy-carbonyl-amino-3-methyl-N-[2,3,4,5-tetrahydro-2-oxo-1H-1-benzazepin-3(R)-yl]-butanamide in 1 mL of dry dimethylformamide at room temperature under a nitrogen atmosphere was treated with 5 mg of 60% sodium hydride oil dispersion (3 mg NaH, 0.13 mmol) and the resulting yellow solution stirred at room temperature for 20 minutes. A solution of 49 mg (0.10 mmol) of the intermediate obtained in Step N in 1 mL of dry dimethylformamide was added and the reaction mixture stirred at room temperature for two hours. To the reaction mixture was added ethyl acetate and water; the organic layer was removed, washed with water, dried over magnesium sulfate, filtered and solvents removed under vacuum. The crude product was purified by chromatography on silica, eluting with hexane/ethyl acetate (1:1), to give 28 mg (37%) of the product. FAB-MS: calculated for C$_{43}$H$_{47}$N$_5$O$_6$S 761; found 768(M+Li, 22%), $^1$H NMR (200 MHz, CDCl$_3$); 1.33 (s, 6H), 1.39 (s, 9H), 1.79 (m, 1H), 2.30–2.65 (m, 5H), 4.46 (m, 1H), 4.67 (d, 15 Hz, 1H), 5.24 (d, 15 Hz, 1H), 5.33 (s, 1H), 6.67 (d, 7 Hz, 1H), 6.88 (d, 8 Hz, 2H), 6.90–7.55 (m, 16H).

Step F: 3-Amino-3-methyl-N-[2,3,4,5-tetrahydro-2-oxo-1[[(2'-(1H-imidazol-2-yl)[1,1'-biphenyl]-4-yl]methyl]-1H-1-benzazepin-3(R)-yl]-butanamide, di(trifluoroacetate)

A solution of 28 mg (0.037 mmol) of the intermediate obtained in Step O in 1 mL of methylene chloride was treated with 10 mg (0.073 mmol) of 1-hydroxybenzotriazole hydrate. The reaction mixture was stirred for 4 hours at room temperature then evaporated to dryness under vacuum. The residue was redissolved in 1 mL of methanol and treated with 0.5 mL of concentrated hydrochloric acid. The mixture was stirred at room temperature for 14 hours then evaporated to dryness under vacuum. The residue was initially purified by reverse phase high pressure liquid chromatography on C18, eluting with methanol/0.1% aqueous trifluoroacetic acid (linear gradient: 40% methanol increased to 70% methanol over 10 minutes). Final purification by reverse phase high pressure liquid chromatography on C18, eluting with methanol/0.1% aqueous trifluoroacetic acid (isocratic 50:50) gave 15 mg of the title compound as a colorless glass, FAB-MS: calculated for C$_{31}$H$_{33}$N$_5$O$_2$ 507: found 508 (M+H, 80%). $^1$H NMR (200 MHz, CD$_3$OD): 1.31 (s, 3H), 1.35 (s, 3H), 2.08 (m, 1H), 2.2–2.6 (m, 5H), 4.36 (dd; 8.11 Hz; 1H), 4.80 (d, 15 Hz, 1H), 5.36 (d, 15 Hz, 1H), 7.04 (d, 8 Hz, 2H), 7.21 (m, 4H), 7.35 (m, 2H), 7.45 (d, 2 Hz, 1H), 7.5–7.8 (m, 5H).

EXAMPLE 2

3-Amino-3-methyl-N-[2,3,4,5-tetrahydro-2-oxo-1-[[2'-(2-thienyl)[1,1'-biphenyl]-4-yl]methyl]-1H-1-benzazepin-3(R)-yl]-butanamide, trifluoroacetate Step A: 4-Methylphenyltrimethylstannane 41.4 L of 1.0M p-tolylmagnesium bromide in diethyl ether (41.4 mol) was added dropwise, maintaining the temperature below −5° C., over 4 hours to a solution of 546 g (2.79 mol) of trimethyltin chloride in tetrahydrofuran (4 L) under nitrogen at −10° C. The suspension was allowed to warm slowly to room temperature over 12 h then saturated ammonium chloride solution (1 L) was added followed by sufficient water (approximately 1 L) to dissolve the precipitate. The solution was extracted with ether-hexane (1:1) (1×4 L, 3×2 L). The combined organic phases were washed with brine, dried over magnesium sulfate and the solvents removed under vacuum. Purification by flash chromatography on silica gel, eluting with hexane/ethyl acetate (95:5), gave a pale yellow oil containing white crystals of 4,4'-dimethylbiphenyl which were removed by filtration to leave 711.3 g (100%) of product. $^1$H NMR (300 MHz, CDCl$_3$): 0.30 (s 9H), 2.34 (s, 3H), 7.19 (d, 7.7 Hz, 2H), 7.40 (d, 7.7 Hz, 2H).

Step B: 1-Bromo-2-(2-thienyl)benzene

A solution of 8.8 mL of isoamylnitrite (65.5 mmol) in 85 mL of thiophene under a nitrogen atmosphere was heated to 50° C. and treated dropwise with a solution of 7.5 g of 2-bromoaniline (43.5 mmol) dissolved in 20 mL of thiophene. After addition was complete, the temperature was raised to 90° C. After 90 minutes, no starting aniline was observed by thin layer chromatography (hexane/ether;100:5). The reaction mixture volume was reduced by atmospheric distillation. The residue was dissolved in ether and the organic layer was washed twice with water, dried over magnesium sulfate and evaporated under vacuum. The residue was dissolved in n-hexane/ether (100:5) and passed over silica gel, eluting with n-hexane/ether (100:5) to give 3.5 g (14.6 mmol, 34%) of the product, $^1$H NMR (200 MHz, CDCl$_3$): 7.11 (m, 1H), 7.16 (dd, 1H), 7.27 (m, 2H), 7.37 (dd, 1H), 7.42 (dd, 1H), 7.66 (dd, 1H).

Step C: 4-Methyl-2'-(2-thienyl)-1,1'-biphenyl

A vigorously stirred solution of 3.4 g (14 mmol) of 1-bromo-2-(2-thienyl)benzene and 3.77 g (15 mmol) of 4-methylphenyltrimethylstannane in 50 mL of dimethylformamide under a nitrogen atmosphere was treated with 427 mg of bis(triphenylphosphine) palladium(II) chloride and the resulting mixture heated at 100° C. for 4.5 hours. The reaction mixture was cooled, poured into 250 mL of water and the resultant mixture extracted with ethyl ether. The combined extracts were washed with water (4×), dried over magnesium sulfate and evaporated under vacuum. The residue was dissolved in hexane/ether (100:5) and chromatographed on silica gel, eluting with hexane/ether (100:5) to give 2.25 g of he product. $^1$H NMR (200 MHz, CDCl$_3$): 2.33 (s, 3H), 6.48 (dd, 1H), 6.83 (dd, 1H), 7.08 (m, 4H), 7.16 (dd, 1H), 7.35 (m, 3H), 7.46 (dd, 1H).

Step D: 4-Bromomethyl-2'-(2-thienyl)-1,1'-biphenyl

A solution of 123 mg (0.492 mmol) of 4-methyl-2'-(2-thienyl)-1,1'-biphenyl, 18.5 mg of AIBN and 110 mg (0.62 mmol) of N-bromosuccinimide in 50 mL of carbon tetrachloride was heated at reflux until a negative starch iodide reaction was obtained (2 hr). The reaction mixture was evaporated under vacuum and the residue triturated with hexane. The hexane washes were filtered and the filtrate evaporated under vacuum to give 158 mg of product. $^1$H NMR (300 MHz, CDCl$_3$): 4.48 (s, 2H), 6.68 (dd, 1H), 6.88 (dd, 1H), 7.11 (m, 5H), 7.36 (m, 3H), 7.50 (dd, 1H).

Step E: 3-t-Butoxycarbonylamino-3-methyl-N-[2,3,4,5-tetrahydro-2-oxo-1-[[2'-(2-thienyl)[1,1'-biphenyl]-4-yl]methyl]-1H-1-benzazepin-3(R)-yl]-butanamide A solution of 174 mg (0.465 mmol) of 3-t-butoxycarbonylamino-3-methyl-N-[2,3,4,5-tetrahydro-2oxo-1H-1-benzazepin-3(R)-yl]-butanamide (Example 1, Step I) in 3.0 mL of dry dimethylformamide was treated with 22.2 mg of 60% sodium hydride oil dispersion (13.3 mg NaH, 0.558 mmol, 1.2 eq). The reaction mixture was stirred at room temperature for 30 minutes. To the solution was added 153 mg (0.465 mmol) of a solution of 4-bromomethyl-2'-(2-thienyl)-1,1'-biphenyl dissolved in 3 mL of dry dimethylformamide. After stirring at room temperature for 3 hours, the reaction mixture was diluted with ethyl acetate. The organic layer was washed with water (4×), dried over magnesium sulfate, filtered and evaporated under vacuum. The residue was purified by chromatography on silica gel, eluting with hexane/ethyl acetate (1:1) to give 160 mg of the product.

Step F: 3-Amino-3-methyl-N-[2,3,4,5-tetrahydro-2-oxo-1-[[2'-(2-thienyl)[1,1'-biphenyl]-4-yl]methyl]-1H-1-benzazepin-3(R)-yl]-butanamide, trifluoroacetate A solution of 154 mg (0.247 mmol) of the intermediate obtained in Step E dissolved in 12.3 mL of methanol was treated with an equivalent volume of 9N aqueous hydrochloric acid. After stirring at room temperature for 16 hours, all volatiles were removed under vacuum and the residue purified by medium pressure liquid chromatography on C8, eluting with methanol/0.1% aqueous trifluoroacetic acid (75:25). The fractions containing the product were combined and solvents removed under vacuum. The residue was lyophilized from water to give 36 mg (0.056 mmol, 23%) of the title compound as a white solid. FAB-MS: calculated for C$_{31}$H$_{32}$N$_4$O$_2$S 524; found 524 (M$^+$). $^1$H NMR (300 MHz, CD$_3$OD): 1.39 (s, 3H), 1.42 (s, 3H), 2.13 (m, 1H), 3.35 (m, 1H), 2.55 (m, 4H), 4.41 (dd, 1H), 4.85 (d, 1H), 5.39 (d, 1H), 6.61 (dd, 1H), 6.81 (d, 1H), 7.35 (dd, 2H), 7.19 (m, 2H), 7.55 (m, 8H), 7.54 (dd, 1H).

EXAMPLE 3

3-Amino-3-methyl-N-[2,3,4,5-tetrahydro-2-oxo-1-[[2'-(thiazol-2-yl)[1,1'-biphenyl]-4-yl]methyl]-1H-1-benzazepin-3-(R)-yl]-butanamide, trifluoroacetate Step A: 2-Bromo-(thiobenzamide)

Gaseous hydrogen sulfide was bubbled into a stirred solution of 1.82 g (10.0 mmol) of 2-bromobenzonitrile, 13 mL of triethylamine and 10 mL of pyridine. After 4 hours, the reaction mixture was poured into 200 mL of ice-water mixture. The resultant oil slowly crystallized. The precipitate was removed by filtration, washed with water (3×) and dissolved in methylene chloride. The organic layer was separated, dried over magnesium sulfate and filtered. The filtrate was evaporated under vacuum to give 1.46 g (6.76 mmol, 68%) of the product. $^1$H NMR (200 MHz, CDCl$_3$): 7.24 (m, 4H), 7.52 (dt, 1H), 8.59 (dd, 1H).

Step E: 1-Bromo-2-(thiazol-2-yl) enzene

A solution of 2.16 g (10.0 mmol) of the intermediate obtained in Step A dissolved in 8 mL of 95% ethanol was treated with 2.0 g (10.0 mmol) of bromoacetaldehyde diethyl acetal. The mixture was then treated with concentrated hydrochloric acid. After heating at reflux for 3 hours, the reaction mixture was cooled, diluted with 100 mL of water and the pH was adjusted to 10 with aqueous 5N sodium hydroxide. The reaction mixture was extracted with ether. The combined extracts were washed with water, dried over magnesium sulfate, filtered and evaporated under vacuum. The residue was purified by chromography over silica gel, eluting with hexane/ether (100:5), to give 1.61 g (6.70 mmol), 67%) of the product. $^1$H NMR (200 MHz, CDCl$_3$): 7.32 (dt, 1H), 7.46 (dt, 1H), 7.55 (d, 1H), 7.73 (dd, 1H), 7.99 (d, 1H), 8.02 (dd, 1H).

Step C: 4-Methyl-2'-(thiazol-2-yl)-1,1'-biphenyl

A solution of 1.18 g (4.92 mmol) of 1-bromo-2-(thiazol-2-yl)benzene and 1.67 g (6.55 mmol) of 4-metylphenyltrimethylstannane in 20 mL of dimethylformamide was treated with 621 mg of bis(triphenylphosphine)palladium(II) chloride. The reaction mixture was heated at 150° C. for 6 hours, cooled and poured into 300 mL of water. The resultant mixture was extracted with ether (3×100 mL). The combined ether extracts were washed with water (4×), dried over magnesium sulfate and evaporated under vacuum. The residue was purified by chromatography on silica gel, eluting with hexane/ether (100:10) to give 381 mg of the product. EI-MS: calculated for C$_{16}$H$_{13}$NS 251; found 250. $^1$H NMR (200 MHz, CDCl$_3$): 2.36 (s, 3H), 7.14 (s, 4H), 7.24 (d, 1H), 7.40 (m, 1H), 7.42 (m, 2H), 7.73 (d, 1H), 8.20 (dt, 1H).

Step D: 4-Bromomethyl-2'-(thiazol-2-yl)-1,1'-biphenyl

Prepared from 4-methyl-2'-(thiazol-2-yl)-1,1'-biphenyl by the procedure described in Example 2, Step D.

Step E: 3-t-Butoxycarbonylamino-3-methyl-N-[2,3,4,5-tetrahydro-2-oxo-1-[[2'-(thiazol-2-yl)[1,1'-biphenyl]-4-yl]methyl]-1H-1-benzazepin-3(R)-yl]-butanamide Prepared from 3-t-butoxycarbonylamino-3-methyl-N-[2,2,4,5-tetrahydro-2-oxo-1H-1-benzaepin-3(R)-yl]-butanamide (Example 1, Step I) and 4-bromomethyl-2'-(thiazol-2-yl)-1,1'-biphenyl by the procedure described in Example 2, Step E.

Step F: 3-Amino-3-methyl-N-[2,3,4,5-tetrahydro-2-oxo-1-[[2'-(thiazol-2-yl)[1,1'-biphenyl]-4-yl]methyl]-1H-1-benzazepin-3(R)-yl]-butanamide, trifluoroacetate Prepared from the intermediate obtained in Step E by the procedure described in Example 2. Step F FAB-MS: calculated for C$_{31}$H$_{32}$N$_4$O$_2$S 524; found 525 (M+1), $^1$H NMR (400 MHz, CD$_3$OD); 1.34 (s, 3H), 1.38 (s, 3H), 2.11 (m, 1H), 2.32 (m, 1H), 2.52 (dd, 2H), 2.57 (m, 2H), 4.39 (dd, 1H), 4.87 (d, 1H), 5.38 (d, 1H), 7.08 (d, 2H), 7.20 (d, 2H), 7.27 (m, 2H), 7.36 (m, 4H), 7.47 (m, 1H), 7.52 (m, 1H), 7.70 (d, 1H), 7.80 (dd, 1H).

EXAMPLE 4

3-Amino-3-methyl-N-[2,3,4,5-tetrahydro-2-oxo-1-[[2'-(1H-pyrazol-3-yl) [1,1'-biphenyl]-4yl]methyl]-1H-1-benzazepin-3(R)-yl]-butanamide, trifluoroacetate Step A: 4-Methyl-2'-acetyl-1,1'-biphenyl A vigorously stirred solution of 13.25 g (66 mmol) of 2-bromoacetophenone and 22.8 g (89 mmol) of 4-methylphenyltrimethylstannane in 190 mL of dimethylformamide under a nitrogen atmosphere was treated with 8.64 g (12 mmol) of bis(triphenylphosphine) palladium(II) chloride and the resulting mixture heated at 150° C. for 6 hours. The reaction mixture was cooled, poured into water (1000 mL) and the resultant suspension extracted with ethyl ether. The combined extracts were washed with water (4×), dried over magnesium sulfate and evaporated under vacuum. The residue was purified by preparative high pressure liquid chromatography on silica gel, eluting with hexane/ethyl acetate (10:1), to give 9.8 g (47 mmol, 71%) of the product as an oil. EI-MS: calculated for $C_{15}H_{14}O$ 210: found 210 (M+). $^1H$ NMR (200 MHz, $CDCl_3$): 1.98 (s, 3H), 2.37 (s, 3H), 7.20 (s, 4H), 7.3–7.5 (m, 4H).

Step B: 4-Methyl-2'-[3-hydroxypropenoyl]-1,1'-biphenyl, sodium salt

A rapidly stirred suspension of 133 mg (5.78 mmol) of finely cut sodium pieces in 25 mL of ether was treated, dropwise, with a solution of 1.05 g (5.0 mmol) of 4-methyl-2'-acetyl-1,1'-biphenyl dissolved in 1.5 mL of ethyl formate. After the addition of approximately 25% of the solution, a vigorous reaction occurred. The rate of addition was adjusted so as to moderate the reaction. After the addition was complete, the reaction mixture was stirred for an additional hour. The reaction mixture was filtered and the cake was washed with ether (4×) to yield 1.34 g of crude product which was used in the next step without purification.

Step C: 4-Methyl-2'-[1H-pyrazol-3-yl]-1,1'-biphenyl

A solution of 600 mg (2.3 mmol) of the crude intermediate obtained in Step B, dissolved in 7 mL of ethanol and 3 mL of water, was treated with 1 mL of an aqueous solution of 243 mg (2.3 mmol) of sodium carbonate. The reaction mixture was treated with 315 mg (4.6 mmol) of hydrazine hydrochloride, then heated at reflux for 30 minutes. The reaction mixture was partially concentrated under vacuum and then diluted with 70 mL of water. The resultant mixture was extracted several times with ether. The combined extracts were washed with water, dried over magnesium sulfate, filtered and evaporated under vacuum. The residue was purified by chromatography over silica gel, eluting with hexane/ethyl acetate (2:1), to yield 458 mg (1.96 mmol, 85%) of the product. FAB-MS: calculated for $C_{16}H_{14}N_2$ 234; found 233 (M-1). $^1H$ NMR (200 MHz, $CDCl_3$): 2.40 (s, 3H), 6.16 (d, 1H), 7.28 (m, 8H), 7.64 (dd, 1H).

Step D: 4-Methyl-2'-[(2-triphenylmethyl)pyrazol-3-yl]-1,1'-biphenyl and 4-methyl-2'-[(1-triphenylmethyl)pyrazol-3-yl]-1,1'-biphenyl A solution of 1.01 g (4.32 mmol) of the intermediate obtained in Step C in 6.8 mL of dry dimethylformamide was treated with 184 mg of 60% sodium hydride oil dispersion (110 mg NaH, 4.5 mmol, 1.07 eq). After stirring at room temperature for 30 minutes, the reaction mixture was treated with 1.29 g (4.62 mmol) of triphenylmethyl chloride. After stirring at room temperature for 2 hours, the reaction mixture was poured into 100 mL of water and the resultant suspension extracted several times with ether. The combined extracts were washed with water (4×), dried over magnesium sulfate, filtered and evaporated under vacuum. The residue was purified by preparative thin layer chromatography with multiple elutions of hexane/ethyl acetate (5:1) to yield 40 mg of a faster minor isomer 4-methyl-2'-[(2-triphenylmethyl)pyrazol-3-yl]-1,1'-biphenyl (200 MHz, $CDCl_3$); 2.34 (s, 3H), 6.38 (d, 1H), 7.20 (m, 23H), 7.50 (dd, 1H); as well as 310 mg of a slower major component, 4-methyl-2'-[(1-triphenylmethyl)pyrazol-3-yl]-1,1-biphenyl, (200 MHz, $CDCl_3$): 2.38 (s, 3H), 5.68 (d, 1H), 7.20 (m, 23H), 7.68 (dd, 1H).

Step E: 4-Bromomethyl-2'-[(1-triphenylmethyl)pyrazol-3-yl]-1,1'-biphenyl

Prepared from 4-methyl-2'-[(1-triphenylmethyl)pyrazol-3-yl]-1,1'-biphenyl by the procedure described in Example 2, Step D. $^1H$ NMR (200 MHz, $CDCl_3$): 4.40 (s, 2H), 5.70 (d, 1H), 7.20 (m, 23H), 7.62 (dd, 1H).

Step F: 3-t-Butoxycarbonylamino-3-methyl-N-[2,3,4,5-tetrahydro-2-oxo-1-[[(2'-triphenylmethyl)pyrazol-3-yl][1,1'-biphenyl]-4-yl]methyl]-1H-1-benzaepin-3(R)-yl]-butanamide Prepared from 3-t-butoxycarbonylamino-3-methyl-N-[2,3,4,5-tetrahydro-2-oxo-1H-1-benzazepin-3-(R)-yl]-butanamide (Example 1, Step I) and 4-bromomethyl-2'-[(1-triphenylmethyl)pyrazol-3-yl]-1,1'-biphenyl by the procedure described in Example 2, Step E.

Step G: 3-Amino-3-methyl-N-[2,3,4,5-tetrahydro-2-oxo-1-[[2-(1H-pyrazol-3-yl)[1,1'-biphenyl]-4-yl]methyl]-1H-1-benzazepin-3(R)-yl]-butanamide, trifluoroacetate The title compound was prepared from the intermediate obtained in Step F by the procedure described in Example 2, Step F. FAB-MS: calculated for $C_{31}H_{33}N_5O_2$ 507; found 508 (M+1). $^1H$ NMR (400 MHz, $CD_3OD$), 1.35 (s, 3H), 1.38 (s, 3H), 2.10 (m, 1H), 2.30 (m, 1H), 4.38 (dd, 1H), 4.82 (d, 1H), 5.32 (d, 1H), 5.55 (br s, 1H), 7.06 (d, 1H), 7.15 (d, 1H), 7.24 (m, 1H), 7.38 (m, 10H), 7.68 (dd, 1H).

EXAMPLE 5

3-Amino-3-Methyl-N-[2,3,4,5-tetrahydro-2-oxo-1-[[2'-(1H-imidazol-4-yl)[1,1'-biphenyl]-4-yl]methyl]-1H-1-benzazepin-3(R)-yl]-butanamide, di(trifluoroacetate)

Step A: 4-Methyl-2'-bromoacetyl-1,1'-biphenyl

A solution of 2.06 g (9.79 mmol) of 4'-methyl-2-acetyl-1,1'-biphenyl (Example 4, Step A) in 10 mL of glacial acetic acid was treated dropwise with a solution of bromine (1.722 g, 1.07 mmol) dissolved in 3.0 mL of glacial acetic acid. After initiating the reaction with the first few drops of the bromine/acetic acid reagent by heating the reaction mixture at 30°C., the remainder of the bromine solution was added dropwise at 25°–30° C. The reaction mixture was stirred at room temperature until the consumption of bromine was complete (approximately 2 hrs). The reaction mixture was diluted with 150 mL of hexane then washed with water (3×50 mL). The organic layer was removed, dried over magnesium sulfate, filtered and evaporated under vacuum to give 2.92 g of an oil that was used in the next step without purification. $^1H$ NMR (crude product) (200 MHz, $CDCl_3$): 2.38 (s, 3H), 3.66 (s, 2H), 7.21 (s, 4H), 7.3–7.6 (m, 4H).

Step B: 4-Methyl-2'-(1H-imidazol-4-yl)-1,1'-biphenyl

A vigorously stirred solution of 1.0 g (3.5 mmol) of 4-methyl-2'-bromoacetyl-1,1'-biphenyl and 1.86 g of formamidine acetate in 10 mL of formamide was heated at 150° C. for 6 hours. The reaction mixture was cooled, poured into 100 mL of water and the resultant mixture extracted several times with ether. The combined extracts were washed with water (3×), dried over magnesium sulfate, filtered and evaporated under vacuum. The residue was purified by chromatography over silica gel, eluting with hexane/ethyl acetate (1:1) to yield 200 mg (0.86 mmol, 24%) of the product. FAB-MS (Li spike): calculated for $C_{16}H_{14}N_2$ 234; found 241 (M+Li). $^1H$ NMR (200 MHz, $CDCl_3$); 2.34 (s, 3H), 6.61 (s, 1H), 7.10 (m, 4H), 7.30 (m, 3H), 7.48 (s, 1H), 7.68 (dd, 1H).

Step C: 4-Methyl-2'-[1-(triphenylmethyl)imidazol-4-yl]-1,1'-biphenyl

A solution of 474 mg (2.03 mmol) of the intermediate obtained in Step B in 2 mL of dry dimethylformamide was treated with 25 mg of 60% sodium hydride oil dispersion (15 mg NaH, 0.63 mmol). After stirring at room temperature for 30 minutes, the reaction mixture was treated with 160 mg (0.575 mmol) of triphenylmethyl chloride. After stirring at room temperature for 2 hours, the reaction mixture was poured into 100 mL of water and the resultant suspension extracted several times with ether. The combined extracts were washed with water (4×), dried over magnesium sulfate, filtered and evaporated under vacuum. The residue was purified by preparative thin layer chromatography with multiple elutions of hexane/ethyl acetate (2:1) to yield 110 mg (0.23 mmol, 11%) of the product. FAB-MS (Li spike): calculated for $C_{35}H_{28}N_2$ 476; found 483 (M+Li). $^1$H NMR (200 MHz, $CDCl_3$); 2.32 (s, 3H), 5.85 (d, 1H), 7.02 (m, 10H), 7.73 (m, 15H).

Step D: 4-Bromomethyl-2'-[1-(triphenylmethyl)imidazol-4-yl]-1,1'-biphenyl

Prepared from 4-methyl-2'-[1-(triphenylmethyl)imidazol-4-yl]-1,1'-biphenyl by the procedure described in Example 2, Step D. $^1$D NMR (200 MHz, $CDCl_3$): 4.2 (s, 2H), 5.92 (d, 1H), 6.92 (m, 6H), 7.25 (m, 18H), 8.01 (d, 1H).

Step E: 3-t-Butoxycarbonylamino-3-methyl-N-[2,3,4,5-tetrahydro-2-oxo-1-[[2'-[1-(triphenylmethyl) imidazol-4-yl] [1,1'-biphenyl]-4-yl]methyl]-1H-1-benzazepin-3(R)-yl]-butanamide Prepared from 3-t-butoxycarbonylamino-3-methyl-N-[2,3,4,5-tetrahydro-2-oxo-1H-1-benzazepin-3(R)-yl]-butanamide (Example 1, Step I) and 4-bromomethyl-2'-[1-(triphenylmethyl)imidazol-4-yl]-1,1'-biphenyl by the procedure described in Example 2, Step E.

Step F: 3-Amino-3-methyl-N-[2,3,4,5-tetrahydro-2-oxo-1-[[2'-(1H-imidazol-4-yl)[1,1'-biphenyl]-4yl]methyl]-1H-1-benzazepin-3(R)-yl]-butamide, di(trifluoroacetate)

The title compound was prepared from the intermediate obtained in Step E by the procedure described in Example 2, Step F. FAB-MS (Li spike); calculated for $C_{31}H_{33}N_5O_2$ 507; found 514 (M+Li). $^1$H NMR (400 MHz, $CD_3OD$): 1.34 (s, 3H), 1.38 (s, 3H), 2.10 (m, 1H), 3.32 (m, 1H), 2.52 (dd, 2H), 2.57 (m, 2H), 4.38 (dd, 1H), 4.84 (d, 1H), 5.33 (d, 1H), 6.91 (br, s, 1H), 7.11 (d, 2H), 7.21 (d, 4H), 7.39 (m, 3H), 7.51 (m, 3H), 8.86 (brs, 1H).

EXAMPLE 6

3-Amino-3-methyl-N-[2,3,4,5-tetrahydro-2-oxo-1-[[2'-(1H-1,2,3-triazol-4-yl)[1,1'-biphenyl]-4-yl]methyl]-1H-1-benzazepin-3(R)-yl]-butanamide, trifluoroacetate Step A: 4-Methyl-2'-nitro-1,1'-biphenyl A vigorously stirred mixture of 4-tolylboronic acid (34 g, 0.25 mol) and 2-bromo-1-nitrobenzene (34 g, 0.168 mol) in a mixture of 5N sodium hydroxide (170 mL), water (57 mL), isopropanol (215 mL) and benzene (1080 mL) under a nitrogen atmosphere was treated with (tetrakis)triphenylphosphine palladium (0) (11.9 g). The stirred bilayer reaction mixture was heated at reflux for 3 hours. The cooled reaction mixture was filtered through Celite and the filter cake washed with fresh benzene. The organic layer was separated and washed with water (3×), dried over magnesium sulfate and filtered. The filtrate was evaporated under vacuum and the residue (46.1 g) purified by preparative high pressure liquid chromatography on silica gel, eluting with hexane/ethyl acetate (20:1), to give 28.05 g of the product. EI-MS: calculated for $C_{13}H_{11}NO_2$ 213; found 213 (M+). $^1$H NMR (400 MHz, $CDCl_3$); 2.38 (s, 3H), 7.20 (m, 4H), 7.43 (m, 2H), 7.59 (t, 1H), 7.8 (d, 1H).

Step B: 4-Methyl-2'-amino-1,1'-biphenyl

A solution of 15 g (70 mmol) of 4-methyl-2'-nitro-1,1'-biphenyl in 160 mL of methanol containing 900 mg of 5% palladium on carbon was hydrogenated for 1.5 hours at 40 psi. The reaction mixture was filtered through Celite and the filtrate evaporated under vacuum to yield 11.94 g (65.2 mmol, 93%) of the product. FAB-MS: calculated for $C_{13}H_{13}N$ 183; found 184 (M+1).

Step C: 4-Methyl-2'-iodo-1,1'-biphenyl

A suspension of 10.0 g (54.6 mmol) of 4-methyl-2'-amino-1,1'-biphenyl in 135 mL of water containing 15 mL of concentrated hydrochloric acid was cooled at −5° C. and treated dropwise with a solution of 3.94 g (57.1 mmol) of sodium nitrite in 9.24 mL of water while maintaining the temperature below 0° C. After the addition was complete, the reaction mixture was stirred an additional 10 minutes. The reaction mixture was slowly poured into a vigorously stirred solution of 29.6 g (178 mmol) of potassium iodide and 643 mg (2.5 mmol) of iodine dissolved in 80 mL of water. When the addition was complete, the reaction mixture was slowly warmed to 35° C. and stirred for an additional 25 minutes. The reaction mixture was cooled, and extracted with ethyl ether. The combined extracts were washed with aqueous 10% sodium thiosulfate (3×). aqueous saturated sodium bicarbonate (1×), and water (1×). The extracts were dried over magnesium sulfate, filtered and evaporated under vacuum to yield 14 g of crude product. The product was purified by chromatography over silica gel, eluting with hexanes to yield 9.34 g (31.8 mmol, 58%) of the product. FAB-MS: calculated for $C_{13}H_{11}I$ 294; found 295 (M+1). $^1$H NMR (200 MHz, $CDCl_3$): 2.42 (s, 3H): 7.14 (dt, 1H), 7.32 (m, 5H), 7.95 (dd, 1H).

Step D: 4-Methyl-2'-trimethylsilyethynyl-1,1'-biphenyl

A suspension of 5.2 g (17.7 mmol) of 4-methyl-2'-iodo-1,1'-biphenyl, 77 mL of triethylamine, 3.1 mL (22 mmol) of trimethylsilyl acetylene containing 234 mg of cuprous iodide was treated with 470 mg of bis(triphenylphosphine) palladium (II) chloride. After stirring at room temperature for 16 hours, the reaction mixture was evaporated under vacuum. The residue was triturated with ether and filtered. The cake was washed with ether (2×). The combined ethereal solutions were evaporated under vacuum to yield 5.23 g of crude product. FAB-MS: calculated for $C_{18}H_{20}Si$ 264; found 264. $^1$H NMR (200 MHz, $CDCl_3$): 0.14 (s, 9H), 2.40 (s, 3H), 7.24 (m, 3H), 7.39 (m, 2H), 58 (m, 3H).

Step E: 4-Methyl-2'-ethynyl-1,1'-biphenyl

A solution of 5.23 g (19.8 mmol) of 4-methyl-2'-trimethylsilylethynyl-1,1'-biphenyl in 60 mL of methanol was treated with 6 mL of 1.25N aqueous sodium hydroxide. The reaction mixture was stirred at room temperature for 30 minutes and evaporated under vacuum. The residue was extracted with ether. The combined ether extracts were washed with water, dried over magnesium sulfate and evaporated under vacuum. The residue was purified by chromatography over silica gel, eluting will hexane, to yield 2.52 g (13.1 mmol, 66%) of the product. FAB-MS: calculated from $C_{15}H_{12}$ 192; found 191 (M−1). $^1$H NMR (200 MHz, $CDCl_3$): 2.40 (s, 3H), 5.26 (s, 1H), 7.3 (m, 8H).

Step F: 4-Methyl-2'-(1H-1,2,3-triazol-4-yl)-1,1'-biphenyl

A solution of 2.52 g (13.1 mmol) of 4-methyl-2'-ethynyl-1,1'-biphenyl in 18 mL of trimethylsilyl azide under a nitrogen atmosphere was heated at 120° C. for 72 hours. The volume was reduced by distillation at atmosphere pressure. The residue was dissolved in methylene chloride. The organic layer was washed with water (3×) dried over magnesium sulfate, filtered and evaporated under vacuum to yield 3.1 g of crude product which was purified over silica gel, eluting with hexane/ethyl acetate (3:1) to yield 1.35 g (5.77 mmol, 44%) of the product. FAB-MS: calculated for $C_{15}H_{13}N_3$ 235; found 237. $^1$H NMR (400 MHz, $CDCl_3$): 2.38 (s, 3H), 7.0 (s, 1H), 7.20 (dd, 4H), 7.40 (m, 3H), 7.80 (dd, 1H).

Step G. 4-Methyl-2'-(1-triphenylmethyl-1,2,3-triazol-4yl)-1,1'-biphenyl and 4-methyl-2'-(3-triphenylmethyl-1,2,3-triazol-4-yl)-1,1'-biphenyl Prepared from 4-methyl-2'-(1H-1,2,3-triazol-4-yl)-1,1'-biphenyl by the procedure described in Example 4, Step D: the faster moving, less polar iosmer: $^1$H NMR (200 MHz, $CDCl_3$): 2.35 (s, 3H), 6.95 (s, 1H), 7.70 (m, 9H), 7.37 (m, 9H), 7.74 (dt, 1H).

The more polar, slower moving isomer: $^1$H NMR (200 MHz, CDCl$_3$): 2.30 (s, 3H), 6.43 (s, 1H), 7.0 (m, 9H), 7.32 (m, 9H), 8.15 (dd, 1H).

Step H: 4-bromomethyl-2'-(1-triphenylmethyl-1,2,3-triazol-4-yl)-1,1'-biphenyl and 4-bromomethyl-2'-(2-triphenylmethyl-1,2,3-triazol-4-yl)-1,1'-biphenyl Prepared from 4-methyl-2'-(1-triphenylmethyl)-1,2,3-triazol-4-yl)-1,1'-biphenyl and 4-methyl-2'-(2-triphenylmethyl-1,2,3-triazol-4-yl)-1,1'-biphenyl by the procedure described in Example 2, Step D.

Step I: 3-t-Butoxycarbonylamino-3-methyl-N-[2,3,4,5-tetrahydro-2-oxo-1-[[2'-(N-triphenylmethyl-1,2,3-triazol-4-yl)[1,1'-biphenyl]-4-yl]methyl]-1H-1-benzazepin-3(R)-yl]-butanamide Prepared from 3-t-butoxycarbonylamino-3-methyl-N-[2,3,4,5-tetrahydro-2-oxo-1H-1-benzazepin-3(R)-yl]-butanamide (Example 1, Step I) and 4-bromomethyl-2'-(1-triphenylmethyl-1,2,3-triazol-4-y)-1,1'-biphenyl and 4-bromomethyl-2'-(2-triphenylmethyl-1,2,3-triazol-4-yl)-1,1'-biphenyl by the procedure described in Example 2, Step E.

Step J: 3-Amino-3-methyl-N-[2,3,4,5-tetrahydro-2-oxo-1-[[2'-(1H-1,2,3-triazol-4-yl)[1,1'-biphenyl]-4-yl]methyl]-1H-1-benzazepin-3(R)—yl]-butanamide, trifluoroacetate The title compounds was prepared from the intermediate obtained in Step I by the procedure described in Example 2, Step F. FAB-MS: calculated for C$_{30}$H$_{32}$N$_6$O$_2$ 508; found 509 (M+H). $^1$H NMR (400 MHz, CD$_3$OD): 1.38 (s, 3H), 1.44 (s, 3H), 2.18 (m, 1H), 2.38 (m, 1H), 2.59 (dd, 2H), 2.63 (m, 2H), 4.44 (dd, 1H), 4.92 (d, 1H), 5.39 (d, 1H), 6.82 (s, 1H), 7.20 (dd, 4H), 7.30 (m, 1H), 7.4 (m, 4H), 7.5 (m, 2H), 7.79 (m, 1H).

EXAMPLE 7

3-Amino-3-methyl-N-[2,3,4,5-tetrahydro-2-oxo-1-[[2'-(1H-1,2,4-triazol-3-yl)[1,1'-biphenyl]-4-yl]methyl]-1H-1-benzazepin-3(R)-yl]-butanamide, trifluoroacetate Step A: 4-Methyl-2'-cyano-1,1'-biphenyl A solution of 2.0 g (11 mmol) of 2-bromobenzonitrile, 2.93 g (11.5 mmol) of 4-methylphenyltrimethylstannane and 0.39 g (0.55 mmol) of bis-triphenylphosphine palladium (II) chloride in 50 mL of dry dimethylformamide under nitrogen was heated at 100° C. for 5.5 hours. The reaction was cooled to room temperature. The reaction was poured into 150 mL of water and extracted with ether (3×150 mL). The combined ether extracts were washed with water (4×100 mL) and brine (100 mL), dried over magnesium sulfate, filtered and the solvents removed under vacuum. Purification by flash chromatography on silica gel, eluting with hexane/ether (85:15), afforded 1.69 g (80%) of the product contaminated with approximately 10% of 2-methylbenzonitrile. $^1$H NMR (200 MHz, CDCl$_3$): 2.40 (s, 3H), 7.27 (d, 7 Hz, 2H), 7.30–7.65 (m, 5H), 7.72 (d, 6 Hz, 1H). FAB-MS: calculated for C$_{14}$H$_{11}$N 193; found 193 (M+, 100%).

Step B: 4-Methyl-2'-thiocarboxamido-1,1'-biphenyl

A cooled, stainless steel vessel was charged with 2.5 g (13 mmol) of 4-methyl-2'-cyano-1,1'-biphenyl, 25 mL of pyridine, 25 mL of triethylamine and 9.6 g of hydrogen sulfide then was sealed and heated in a rocking autoclave for 12 hours at 90° C. The reaction vessel was cooled, vented and the contents poured into water. The mixture was extracted several times with ether. The combined extracts were washed with water (5×), dried over magnesium sulfate, filtered and evaporated under vacuum. The residue was purified by chromatography over silica gel, eluting with hexane/ethyl acetate (3:1) to yield 1.88 g (8.28 mmol, 64%) of the product. $^1$H NMR (200 MHz, CDCl$_3$): 2.4 (s, 3H), 6.48 (br s, 2H), 7.3 (m, 7H), 7.9 (dd, 1H).

Step C: 4-Methyl-2'-isothiocarboximino-1,1'-biphenyl, methiodide

A solution of 200 mg (0.88 mmol) of 4-methyl-2'-thiocarboxamido-1,1'-biphenyl in 8 mL of ethyl ether was treated with 0.40 mL (6.4 mmol) of iodomethane. After stirring at room temperature for 24 hours, the reaction mixture was filtered. The precipitate was washed wth ether (3×) and dried under vacuum to yield 270 mg (0.73 mmol, 83%) of the product. $^1$H NMR (200 MHz, CDCl$_3$), 2.42 (s, 3H), 2.9 (s, 3H), 7.27 (s, 4H), 7.5 (m, 2H), 7.65 (t, 2H).

Step D: 4-Methyl-2'-(1H-1,2,4-triazol-3-yl)-1,1'-biphenyl

A stirred solution of 250 mg (0.68 mmol) of the intermediate obtained in Step C dissolved 2.5 mL of dry dimethylforamide under a nitrogen atmosphere was treated with 81 mg (1.4 mmol) of formic hydrazide. The reaction was stirred at room temperature for 16 hours, then heated at 90° C. for 4 hours. The cooled reaction mixture was poured into water and extracted wth ether. The combind extracts were washed with water (4×), dried over magnesium sulfate, filtered and evaporated under vacuum to yield 85 mg (0.36 mmol, 53%) of crude product. $^1$H NMR (200 MHz, CDCl$_3$): 2.40 (s, 3H), 7.15 (d, 2H), 7.21 (d, 2H), 7.34 (m, 1H), 7.44 (m, 2H), 8.05 (s, 1H), 8.15 (dd, 1H).

Step E: 4-Methyl-2'-(1-triphenylmethyl-1,2,4-triazol-3-yl)-1,1'-biphenyl

Prepared from 4-methyl-2'-(1,2,4-triazol-3-yl)-1,1'-biphenyl by the procedure described in Example 4, Step D.

Step F: 4-Bromomethyl-2'-(1-triphenylmethyl-1,2,4-triazol-3-yl)-1,1'-biphenyl

Prepared from 4-methyl-2'-(1-triphenylmethyl-1,2,4-triazol-3-yl)-1,1'-biphenyl by the procedure described in Example 2, Step D.

Step G: 3-t-Butoxycarbonylamino-3-methyl-N-[2,3,4,5-tetrahydro-2-oxo-1-[[2'-(1-triphenylmethyl-1, 2,4-triazol-3-yl)[1,1'-biphenyl]-4-yl]methyl]-1H-1-benzazepin-3(R)-yl]-butanamide Prepared from 3-t-butoxycarbonylamino-3-methyl-N-[2,3,4,5-tetrahydro-2-oxo-1H-1-benzazepin-3(R)-yl]-butanamide (Examle 1, Step I) and 4-bromomethyl-2'-(1-triphenylmethyl-1,2,4-triazol-3-yl)-1,1'-biphenyl by the procedure described in Example 2, Step E.

Step H: 3-Amino-3-methyl-N-[2,3,4,5-tetrahydro-2-oxo-1-[[2'-(1H-1,2,4-triazol-3-yl)[1,1'-biphenyl]-4-yl]methyl]-1H-1-benzazepin-3(R)-yl]-butanamide trifluoroacetate The title compound was prepared from the intermediate obtained in Step G by the procedure described in Example 2, Step F. FAB-MS: calculated for C$_{30}$H$_{32}$N$_6$O$_2$ 508: found 509 (M+H). $^1$H NMR (400 MHz, CD$_3$OD): 1.34 (s, 3H) 1.39 (s, 3H), 2.1 (m, 1H), 2.3 (m, 1H), 2.52 (dd, 2H), 2.54 (m, 2H), 4.38 (dd, 1H), 4.86 (d, 1H), 5.24 (d, 1H), 7.1 (dd, 4H), 7.22 (m, 2H), 7.32 (m, 2H), 7.48 (m, 2H), 7.59 (m, 2H), 8.20 (s, 1H).

EXAMPLE 8

N-[1-[[2'-[[(Thiazol-2-yl)aminocarbonyl]amino][1,1'-biphenyl]-4-yl]methyl]-2,3,4,5-tetrahydro-2-oxo-1H-1-benzazepin-3(R)-yl]-3-amino-3-methylbutanamide, trifluoroacetate Step A: 4-Bromomethyl-2'-nitro-1,1'-biphenyl Prepared from 4-methyl-2'-nitro-1,1'-biphenyl by the procedure described in Example 2. Step D. BI-MS: calculated for C$_{14}$H$_{10}$BrN 272,274; found 272, 274 (M+). $^1$H NMR (200 MHz, CDCl$_3$): 4.53 (s, 2H), 7.2–7.7 (m, 7H), 7.85 (m, 1H).

Step B: N-[1-[[(2'-Nitro)[1,1'-biphenyl]-4-yl]methyl]-2,3,4,5-tetrahydro-2-oxo-1H-1-benzazepin-3(R)-yl ]-3-t-butoxycarbonylamino-3-methylbutanamide Prepared from 4-bromomethyl-2'-nitro-1,1'-biphenyl and 3-t-butoxyca, bonylamino-3-methyl-N-[2,3,4,5-tetrahydro-2-oxo-1H-1-benzazepin-3(R)-yl]-butanamide (Example 1, Step I) by the procedure described in Example 2, Step E. FAB-MS: calculated for C$_{33}$H$_{38}$N$_4$O$_6$ 586; found 587 (M+H). $^1$H NMR (400 MHz, CDCl$_3$): 1.34 (s, 6H), 1.41 (s, 9H), 1.83 (m, 1H), 2.35–2.70 (m, 5H), 4.50 (m, 1H), 4.84 (d, 15 Hz, 1H), 5.23 (d, 15 Hz, 1H), 5.27 (s, 1H), 6.64 (d, 7 Hz, 1H); 7.1–7.6 (m, 11H), 7.80 (d, 8 Hz, 1H).

Step C: N-[1-[[2'-Amino)[1,1'-biphenyl]-4-yl]methyl]-2,3,4,5-tetrahydro-2-oxo-1H-1-benzazepin-3(R)-yl]-3-t-butoxycarbonylamino-3-methylbutanamide A solution of 7.79 g (13.23 mmol) of the intermediate obtained in Step B in 200 mL of methanol containing 0.9 g of 5% palladium on carbon was hydrogenated at 40 psi. When the uptake of hydrogen was complete, the catalyst was removed by filtration through Celite. The filtrate was concentrate under vacuum to yield 6.6 g (11.9 mmol, 90%) of product. FAB-MS: calculated for C$_{33}$H$_{40}$N$_4$O$_4$556; found 557 (M+H). $^1$H NMR (400 MHz, CDCl$_3$): 1.32 (s, 6H), 1.39 (s, 9H), 1.87 (m, 1H), 2.51 (dd, 1H), 2.59 (m, 1H), 4.51 (m, 1H), 4.89 (d, 1H), 5.15 (d, 1H), 5.32 (br s, 1H), 6.71 (d, 1H), 6.81 (s, 1H), 7.21 (m, 10H).

Step D: N-[1-[[(2'-Isocyanato)[1,1'-biphenyl]-4-yl]methyl]-2,3,4,5-tetrahydro-2-oxo-1H-1-benzazepin-3(R)-yl]-3-t-butoxycarbonylamino-3-methylbutanamide A solution of 2.0 g (3.6 mmol) of the intermediate obtained in Step C and 2.0 mL of triethylamine (14 mmol) in 40 mL of methylene chloride under a nitrogen atmosphere was cooled to −10° C. and treated with 2.12 g (7.15 mmol) of triphosgene in one portion. An exotherm occurred. The reaction was stirred at room temperature for 1.5 hours when no starting amine was detected by thin layer chromatography on silica, eluting with hexane/ethyl acetate (1:1). The reaction mixture was diluted with 40 mL of hexane and filtered. The filtrate was passed over 150 g of silica gel and eluted with hexane/ethyl acetate (1:1) to give 1.65 g (2.84 mmol, 79%) of the product. $^1$H NMR (400 MHz, CDCl$_3$): 1.34 (s, 6H), 1.39 (s, 9H), 1.84 (m, 1H), 2.40 (m, 1H), 2.49 (dd, 1H), 2.52 (m, 1H), 4.51 (m, 1H), 4.88 (d, 1H), 5.25 (d, 1H), 5.34 (br s, 1H), 6.71 (d, 1H), 7.20 (m, 12H).

Step E: N-[1-[[2'-[[(Thiazol-2-yl)aminocarbonyl]amino][1,1'-biphenyl]-4-yl]methyl]-2,3,4,5-tetrahydro-2-oxo-1H-1-benzazepin-3(R)-yl]-3-amino-3-methylbutanamide, trifluoroacetate A solution of 116 mg (0.20 mmol) of the intermediate obtained in Step D in 1 mL of methylene chloride under a nitrogen atmosphere was treated with 2-aminothiazole (40 mg, 0.363 mmol). The reaction mixture was stirred at room temperature for 2 hours, when thin layer chromatography (hexane/ethyl acetate; 1:1) showed no starting isocyanate. The reaction mixture was treated with trifluoroacetic acid (0.5 mL). After 1 hr, the reaction mixture was evaporated under vacuum. The residue was purified by reverse phase medium pressure liquid chromatography on C8, eluting with methanol/0.1% aqueous trifluoroacetic acid (55:45). Fractions containing the product were combined, solvents removed under vacuum and the residue lyophilized from water to give 110 mg of impure product. The impure material was further chromatographed on silica gel, eluting with methylene chloride/methanol/concentrated ammonium hydroxide (9:1:0.1) to give 30 mg of product which was lyophilized from water to give 25 mg (0.036 mmol, 18%) of the title compound as a white solid. FAB-MS: calculated for C$_{32}$H$_{34}$N$_6$O$_3$S 582: found 605 (M+Na). $^1$H NMR (400 MHz, CD$_3$OD): 1.22 (s, 3H), 1.26 (s, 3H), 2.12 (m, 1H), 2.36 (m, 1H), 2.40 (dd, 2H), 2.60 (m, 2H), 4.40 (dd, 1H), 5.06 (d, 1H), 5.20 (d, 1H), 6.98 (d, 1H), 7.28 (m, 13H), 7.88 (d, 1H).

EXAMPLE 9

3-Amino-3-methyl-N-[2,3,4,5-tetrahydro-2-oxo-1-[[2'-[(4,5-dihydro-2-oxoazolyl)amino][1,1'-biphenyl]-4-yl]-methyl]-1H-1-benzazepin-3(R)-yl]-butanamide, trifluoroacetate Step A: N-[1-[[2'-[[(2-Hydroxyethylamino)carbonyl]amino][1,1'-biphenyl]-4-yl]methyl]-2,3,4,5-tetrahydro-2-oxo-1H-1-benzazepin-3(R)-yl]-3-t-buboxycarbonylamino-3-methylbutanamide Prepared from N-[1-[[(2'-isocyanato) [1,1'-biphenyl]-4-yl]methyl]2,3,4,5-tetrahydro-2-oxo-1H-1-benzazepin-3(R)-yl]-3-t-butoxycarbonylamino-3-methylbutanamide (Example 8, Step D) and ethanolamine by the procedure described in Example 6, Step A. FAB-MS: calculated for C$_{36}$H$_{45}$N$_5$O$_6$ 643; found 666 (M+Na). $^1$H NMR (400 MHz, CDCl$_3$): 1.29 (s, 3H), 1.31 (s, 3H), 1.38 (s, 9H), 1.90 (m, 1H), 2.5 (dd, 2H), 2.58 (m, 2H), 2.7 (m, 1H), 3.21 (t, 2H), 3.54 (m, 2H), 4.49 (m, 1H), 4.88 (d, 1H), 5.10 (d, 1H), 6.81 (d. 1H), 7.21 (m, 11H), 7.74 (d, 1H).

Step B: 3-t-Butoxycarbonylamino-3-methyl-N-[2,3,4,5-tetrahydro-2-oxo-1-[[2'-[(4,5-dihydro-2-oxazolyl)amino][1,1'-biphenyl]-4-yl]methyl]-1H-1-benzazepin-3(R)-yl]-butanamide A solution containing 500 mg (0.78 mmol) of the intermediate obtained in Step A, 0.125 mL of triethylamine and 50 mg (0.41 mmol) of 4-dimethylaminopyridine dissolved in 8 mL of methylene chloride under a nitrogen atmosphere was cooled to 0° C. and treated dropwise with 0.070 mL of methanesulfonyl chloride. The reaction mixture was stirred at ambient temperature for 1 hour when an additional 0.50 mL of methanesulfonyl chloride was added. After stirring at room temperature for an additional hour, the reaction mixture was diluted to 100 mL with methylene chloride. The organic layer was washed with water, dried over magnesium sulfate, filtered and evaporated under vacuum. The residue was purified by chromatography over silica gel, eluting with methylene chloride/2-propanol (100:5) to yield 190 mg of product. FAB-MS: calculated for C$_{36}$H$_{43}$N$_5$O$_5$ 625; found 626 (M+H), $^1$H NMR (400 MHz, CDCl$_3$): 1.33 (s, 3H), 1.34 (s, 3H), 1.39 (s, 9H), 1.87 (m, 1H), 2.48 (dd, 2H), 2.69 (m, 2H), 3.62 (m, 2H), 4.15 (dt, 2H), 4.51 (m, 1H), 4.90 (d, 1H), 5.20 (d, 1H), 6.69 (d, 1H), 7.20 (m, 12H).

Step C: 3-Amino-3-methyl-N-[2,3,4,5-tetrahydro-2-oxo-1-[[2'-[(4,5-dihydro-2-oxazolyl)amino][1,1'-biphenyl]-4-yl]methyl]-1H-1-benzazepin-3(R)-yl]-butanamide, trifluoroacetate The title compound was prepared from the intermediate obtained in Step B by the procedure described in Example 2, Step F. FAB-MS: calculated for C$_{31}$H$_{35}$N$_5$O$_3$ 525: found 527. $^1$H NMR (400 MHz, CD$_3$OD): 1.34 (s, 3H), 1.39 (s, 3H), 1.23 (m, 1H), 2.34 (m, 1H), 2.56 (dd, 2H), 2.64 (m, 2H), 4.39 (dd, 1H), 4.48 (d, 1H), 5.44 (d, 1H), 7.35 (m, 12H).

EXAMPLE 10

3-[(2(R)-Hydroxypropyl)amino]-3-methyl-N-[2,3,4,5-tetrahydro-2-oxo-1-[[2'-(1H-imidazol-2-yl)[1,1'-biphenyl]-4-yl]methyl]-1H-1-benzazepin-3(R)-yl]-di(trifluoroacetate)

Step A: 3-Amino-3-methyl-N-[2,3,4,5-tetrahydro-2-oxo-1H-1-benzazepin-3(R)-yl]-butanamide, trifluoroacetate To a solution of 150 mg (0.040 mmol) of 3-t-butoxycarbonylamino-3-methyl-N-[2,3,4,5-tetrahydro-2-oxo-1H-1-benzazepin-3(R)-yl]-butanamide (Example 1, Step I) in 2 mL of methylene chloride at 0° C. was added 2 mL of trifluoroacetic acid and the mixture stirred at room temperature for 1 hour. All volatiles were removed under vacuum to give 130 mg (0.33 mmol, 84%) of the product. $^1$H NMR (200 MHz, $CD_3OD$): 1.33 (s, 3H), 1.37 (s, 3H), 2.12 (m, 1H), 2.3–2.6 (m, 3H), 2.6–3.0 (m, 2H), 4.37 (dd; 8, 12Hz; 1H), 7.02 (d, 8 Hz, 1H), 7.1–7.3 (m, 3H). FAB-MS: calculated for $C_{15}H_{21}N_3O_2$ 275; found 276 (M+H, 100%).

Step B: 3-[2(R)-Benzyloxypropyl]amino-3-methyl-N-[2,3,4,5-tetrahydro-2-oxo-1H-1-benzazepin-3 (R)-yl]-butanamide, trifluoroacetate To a solution of 1.0 g (2.57 mmol) of 3-amino-3-methyl-N-[2,3,4,5-tetrahydro-2-oxo-1H-1-benzazepin-3(R)-yl]-butanamide, trifluoroacetate in 25 mL of dry methanol was added 3.0 g of dry 3A powdered molecular sieves followed by a solution of 2.5 g (17 mmol) of (R)-2-benzyloxypropanal (prepared from ethyl-D-lactate according to the procedure of Hanessian and Kloss, Tetrahedron Lett. 1985, 26, 1261–1264) in 5 mL of dry methanol. The pH of the mixture was carefully adjusted to 6 by the addition of trifluoroacetic acid. The reaction was stirred for 2 hours at room temperature at which time 15.4 mL (15.4 mmol) of a 1.0 M solution of sodium cyanoborohydride in tetrahydrofuran was added by syringe. The reaction was stirred for 72 hours then filtered through a pad of Celite. To the filtrate was added 5 mL of trifluoroacetic acid (CAUTION! evolution of hydrogen cyanide) and the resulting mixture was stirred for three hours. The solvent was removed under vacuum to afford a clear oil which was purified by reverse phase medium pressure liquid chromatography on C-8, eluting with methanol/0.1% aqueous trifluoroacetic acid (60:40), to afford 1.27 g (2.36 mmol, 92%) of the product as a white solid. $^1$H NMR (200 MHz, $CD_3OD$): 1.31 (d, 6 Hz, 3H), 1.40 (s, 3H), 1.43 (s, 3H), 2.17 (m, 1H), 2.30 (m, 1H), 2.6–3.1 (m, 5H), 3.22 (dd; 3, 12 Hz; 1H), 3.86 (m, 1H), 4.48 (dd; 7, 12 Hz; 1H), 4.50 (d, 12 Hz, 1H), 4.70 (d, 12 Hz, 1H), 7.11 (d, 8 Hz, 1H), 7.15–7.45 (m, 8H). FAB-MS: calculated for $C_{25}H_{33}N_3O_3$ 423; found 424 (M+H, 100%).

Step C: 3-[2(R)-Benzyloxypropyl]amino-3-methyl-N-[2,3,4,5-tetranydro-2-oxo-1-[[2'-[1-(4-toluenesulfonyl)imidazol-2-yl][1,1'-biphenyl]-4-yl]methyl]-1H-1-benzazepin-3(R)-yl]-butanamide Prepared from 3-[2(R)-benzyloxypropyl]amino-3-methyl-N-[2,3,4,5-tetrahydro-2-oxo-1H-1-benzazepin-3(R)-yl]-butanamide trifluoroacetate and 1-(4-toluenesulfonyl)-2-[4'-(methanesulfonyloxymethyl)-1,1'-biphen-2-yl]imidazole (Example 1, Step N) by the procedure described in Example 1, Step O. The crude product thus obtained was used directly in the next step without purification.

Step D: 3-[2(R)-Benzyloxypropyl]amino-3-methyl-N-[2,3,4,5-tetrahydro-2-oxo-1-[[2'-(1H-imidazol-2-yl) [1,1'-biphenyl]-4-yl]methyl]-1H-1-benzazepin-3(R)-yl]-butanamide, di(trifluoroacetate)

A solution of 50 mg (0.06 mmol) of the crude intermediate obtained in Step C in 0.5 mL of methylene chloride was treated with 25 mg of 1-hydroxybenzotriazole hydrate. The mixture was stirred at room temperature for one hour then all volatiles removed under vacuum and the residue purified by reverse phase medium pressure liquid chromatography on C8, eluting with methanol/0.1% aqueous trifluoroacetic acid (60:40) to give 17 mg (0.02 mmol, 33%) of the product as a colorless glass. FAB-MS: calculated for $C_{41}H_{45}N_5O_3$ 655; found 656 (M+H, 93%). $^1$H NMR (200 MHz, $CD_3OD$); 1.26 (d, 6 Hz, 3 H), 1.36 (br s, 6H), 2.11 (m, 1H), 2.25–2.70 (m 5H), 2.5 (m, 1H), 3.19 (m, 1H), 3.83 (m, 1H), 4.44 (m, 2H), 4.67 (d, 12Hz, 1H), 5.31 (d, 15 Hz, 1H), 7.04 (d, 8 Hz, 2 H), 7.1–7.8 (m, 17H).

Step E: 3-[(2(R)-Hydroxypropyl)amino]-3-methyl-N-[2,3,4,5-tetrahydro-2-oxo-1-[[2'-(1H-imidazol-2-yl) [1,1'-biphenyl]-4-yl]methyl]-1H-1-benzazepin-3(R)-yl]-butanamide, di(trifluoroacetate)

A solution of 51 mg (0.058 mmol) of the intermediate obtained in Step D in 2 mL of methanol was treated with two drops of trifluoroacetic acid and the resulting mixture was hydrogenated at ambient temperature and 40 psi overt 50 mg of 20% palladium on carbon for 24 hours. The reaction mixture was filtered through Celite and the filtrate expaorated to dryness under vacuum. The residue was purified by reverse phase medium pressure liquid chromatography on C8, eluting with methanol/0.1% aqueous trifluoroacetic acid (50:50) to give 15 mg (0.019 mmol, 33%) of the title compound as a colorless glass. FAB-MS: calculated for $C_{34}H_{39}N_5O_3$ 565; found 566 (M+H, 26%). $^1$H NMR (200 MHz, $CD_3OD$): 1.20 (d, 7 Hz, 3H), 1.34 (s, 3H), 1.37 (s, 3H), 2.12 (m, 1H), 2.2–2.6 (m, 5H), 2.80 (dd; 12,14 Hz; 1H), 3.10 (dd; 2.12 Hz; 1H), 3.93 (m, 1H), 4.36 (dd: 8, 12 Hz; 1H), 5.35 (d, 15 Hz, 1H), 7.08 (d, 8 Hz, 2H), 7.26 (m, 4H), 7.37 (m, 2H), 7.44–7.90 (m, 6H).

EXAMPLE 11

3-Amino-3-methyl-N-[2,3,4,5-tetrahydro-2-oxo-1-[[2'-[[(1H-imidazol-4-yl)acetamido]methyl][1,1'-biphenyl]-4-yl]methyl]-1H-1-benzazepin-3(R)-yl]-butanamide, di(trifluoroacetate)

Step A: 2,2-Dimethylbutanedioic acid, 4-methyl ester 2,2-Dimethylsuccinic acid (20 g, 137 mmol) dissolved in 200 mL of absolute methanol at 0° was treated dropwise with 2 mL of concentrated sulfuric acid. After the addition was complete, the mixture was allowed to warm to room temperature and stir for 16 hours. The mixture was concentrated under vacuum to 50 mL and slowly treated with 200 mL of saturated aqueous sodium bicarbonate. The mixture was washed with hexane (3×) and the aqueous layer removed and cooled in an ice bath. The mixture was acidified to pH 2 by slow addition of 6N HCl then extracted with ether (8×). The combined extracts were washed with brine, dried over magnesium sulfate, filtered and solvents removed under vacuum. The residue was dried at room temperature under vacuum to afford 14.7 g (91.8 mmol, 67%) of the product as a viscous oil that slowly solidified upon standing. $^1$H NMR (200 MHz, $CDCl_3$): 1.29 (s, 6H), 2.60 (s, 2H), 3.65 (s, 3H).

Step B: 3-Benzyloxycarbonylamino-3-methylbutanoic acid, methyl ester

To 14.7 g (91.8 mmol) of 2,2-dimethylbutanedioic acid-4-methyl ester in 150 mL of benzene was added 13 mL of triethylamine (9.4 g, 93 mmol) followed by 21.8 mL of diphenylphosphoryl azide (27.8 g, 101 mmol). The mixture was heated under nitrogen at reflux for 45 minutes, then 19 mL (19.9 g, 184 mmol) of benzyl alcohol was added and refluxing continued for 16 hours. The mixtue was cooled, filtered and the filtrate concentrated to a minimum volume under vacuum. The residue was redissolved in 250 mL of ethyl acetate, washed with water, saturated aqueous sodium bicarbonate (2×) and brine. The organic layer was removed, dried over magnesium sulfate, filtered and the filtrate concentrated to a minimum volume under vacuum. The crude product was purified by medium pressure liquid chromatography on silica, eluting with hexane/ethyl acetate (4:1), to afford 18.27 g (68.9 mmol, 75%) of the product. $^1$H NMR (200 MHz, CDCl$_3$): 1.40 (s, 6H), 2.69 (s, 2H), 3.63 (s, 3H), 5.05 (s, 2H), 5.22 (br s, 1H), 7.32 (s, 5H).

Step C: 3-Benzyloxycarbonylamino-3-methylbutanoic acid

A solution of 18.27 g (68.9 mmol) of 3-benzyloxycarbonylamino-3-methylbutanoic acid methyl ester in 20 mL of methanol at room temperature was treated dropwise with 51 mL of 2N NaOH (102 mmol). The mixture was stirred at room temperature for 16 hours then transferred to a separatory funnel and washed with hexane (3×). The aqueous layer was removed, cooled to 0° C. and slowly acidified to pH 2 (paper) by dropwise addition of 6N HCl. This mixture was extracted with ether (6×); combined extracts were washed with 1N HCl and brine, then dried over magnesium sulfate, filtered and solvent removed under vacuum to afford 17.26 g (68.7 mmol, 99%) of the product. $^1$H NMR (200 MHz, CDCl$_3$): 1.42 (s, 6H), 2.77 (s, 2H), 5.06 (s, 2H), 5.2 (br s, 1H), 7.3 (s, 5H).

Step D: 3-Benzyloxycarbonylamino-3-methyl-N-[2,3,4,5-tetrahydro-2-oxo-1H-1-benzazepin-3(R)-yl]-butanamide Prepared from 3-benzyloxycarbonylamino-3-methylbutanoic acid and 3(R)-amino-2,3,4,5-tetrahydro-1H-1-benzazepin-2-one (Example 1, Step E) by the procedure described in Example 1, Step I. FAB-MS: calculated for $C_{23}H_{27}N_3O_4$ 409; found 410 (M+H, 100%). $^1$H NMR (200 MHz, CDCl$_3$): 1.38 (s, 3H), 1.39 (s, 3H), 1.82 (m, 1H), 2.52 s, 2H), 2.5–3.0 (m, 3H), 4.51 (m, 1H), 5.07 (br s, 2H), 5.57 (br s, 1H), 6.68 (d, 7 Hz, 1H), 6.97 (d, 8 Hz, 1H), 7.1–7.4 (m, 8H), 7.61 (br s, 1H).

Step E: 4-(t-Butyldimethylsiloxymethyl)phenylboronic acid

To a solution of 1.8 g (5.97 mmol) of 4-bromobenzyl-t-butyldimethyl silyl ether (prepared according to the procedure of Nassal, *Liebigs Ann. Chem.* 1983, 1510–1523) in 9 mL of dry tetrahydrofuran under a nitrogen atmosphere at −78° C. was added dropwise by syringe 4.1 mL (6.57 mmol) of a 1.6M solution of n-butyl lithium in hexanes over twenty minutes. The resulting mixture was stirred for twenty minutes, then 2.03 mL (17.9 mmol) of trimethyl borate was added by syringe. The reaction mixture was stirred at −78° C. for thirty minutes then slowly warmed to room temperature and stirred for an additional three hours. The reaction mixture was then re-cooled to 0° C. and quenched by the addition of 40 mL of saturated aqueous ammonium chloride. Precipitated solids were dissolved by addition of a minimal amount of water and the mixture stirred for 25 minutes. The solution was transferred to a separatory funnel and extracted with ether (3×75 mL). The combined ether extracts were washed with saturated aqueous sodium chloride, dried over magnesium sulfate and filtered. The solvent was removed under vacuum to give a crude product which was purified by column chromatography on silica gel eluting with hexanes/ethyl acetate (55:45) to afford 1.0 g (63%) of the product as a white solid. $^1$H NMR (200 MHz, CDCl$_3$): 0.10 (s, 6H), 0.91 (s, 9H), 1.50 (s, 2H), 4.80 (s, 2H), 7.43 (d, 8 Hz, 2H), 8.18 (d, 8 Hz, 2H).

Step F: N-(t-Butoxycarbonyl)-2-bromobenzylamine

To a slurry of 1.0 g (4.5 mmol) of 2-bromobenzylamine hydrochloride in 10 mL of dry methylene chloride under a nitrogen atmosphere was added by syringe 1.4 mL (9.9 mmol) of triethylamine. To the resulting solution after five minutes was added 1.08 g (4.94 mmol) of di-t-butyldicarbonate. The reaction was stirred at room temperatue for one hour then diluted with 200 mL of ethyl acetate. The solution was washed with saturated aqueous ammonium chloride, saturated aqueous sodium bicarbonate and saturated aqueous sodium chloride, dried over magnesium sulfate and filtered. The solvent was removed under vacuum to give an oil which was purified by column chromatography on silica gel eluting with hexanes/ethyl acetate (9:1), to afford 1.29 g (100%) of the product as a white solid. FAB-MS: calculated for $C_{12}H_{16}BrNO_2$ 285; found 286 (M+1). $^1$H NMR (200 MHz, CDCl$_3$): 1.41 (s, 5H), 4.37 (d, 5 Hz, 2H), 5.00 (s, 1H), 7.10 (m, 1H), 7.25 (m, 1H), 7.35 (m, 1H), 7.40 (d, 6 Hz, 1H).

Step G: 2'-[(t-Butoxycarbonylamino)methyl]-4-[(t-butyldimethylsiloxy)methyl]-1,1'-biphenyl To a solution of 1.0 g (3.8 mmol) of 4-(t-butyldimethaylsilyoxymethyl)phenylboronic acid (Step E) in 24 mL of 1,2-dimethyoxyethane was added 4 mL of water,m 1.02 g (5.37 mmol) of barium hydroxide hexahydrate, 1.02 g (3.58 mmol) of N-(t-butoxycarbonyl)-2-bromobenzylamine (Step F) and 206 mg (0.18 mmol) of tetrakis(triphenylphosphine) palladium. The resulting mixture was heated under nitrogen at 80° C. for 2.5 hours then cooled to room temperature. The reaction mixture was diluted with 40 mL of saturated aqueous ammonium chloride. The solution was transferred to a separatory funnel and extracted with ether (3×75 mL). The combined ether extracts were washed with saturated aqueous sodium bicarbonate and saturated aqueous sodium chloride, dried over magnesium sulfate and then filtered. The solvent was removed under vacuum to give a crude product which was purified by column chromatography on silica gel eluting with hexanes/ethyl acetate (85:15) to afford 1.15 g (75%) of the product as a clear oil. FAB-MS: calculated for $C_{25}H_{37}NO_3Si$ 427; found 314. $^1$H NMR (200 MHz, CDCl$_3$): 0.10 (s, 6H), 0.92 (s, 9H), 1.40 (s, 9H), 4.27 (d, 5 Hz, 2H), 4.60 (s, 1H), 4.78 (s, 2H), 7.18–7.45 (m, 8H).

Step H: 2'-[(t-Butoxycarbonylamino)methyl]-1,1-biphenyl-4-methanol

To a solution of 150 mg (0.35 mmol) of 2'-[(t-butoxycarbonylamino)methyl]-4-[(t-butyldimethylsiloxy)-methyl]-1,1'-biphenyl (Step G) in 2 mL of dry tetrahydrofuran under a nitrogen atmosphere was added by syringe 0.52 mL (0.53 mmol) of 1.0M solution of tetra-n-butylammonium fluoride in tetrahydrofuran. The reaction mixture was stirred for one hour then diluted with 100 mL of ethyl acetate. The mixture was washed with water (3×20 mL), then saturated aqueous sodium chloride, dried over magnesium sulfate and filtered. The solvent was removed under vacuum to give an oil which was purified by column chromatography on silica gel eluting with hexanes/ethyl acetate (55:45) to afford 101 mg (93%) of the product as a white solid. FAB-MS: calculated for $C_{19}H_{23}NO_3$ 313; found 314 (M+H). $^1$H NMR (200 MHz, CDCl$_3$): 1.40 (s, 9H), 2.50 (s, 2H), 4.20 (s, 2H), 4.70 (s, 2H), 7.18–7.45 (s, 8H).

Step I: 2'-[(t-Butoxycarbonylamino)methyl]-1,1-biphenyl-4-methanol, methanesulfonate ester To solution of 53 mg (0.17 mmol) of 2'-[(t-butoxycarbonylamino)methyl]-1,1-biphenyl-4-methanol (Step H) in 1 mL of dry methylene chloride under nitrogen atmosphere at 0° C. was added by syringe 0.035 mL (0.25 mmol) of triethylamine followed by 0.016 mL of (0.20 mmol) methanesulfonyl chloride. The reaction mixture was stirred for 2 hours at 0° C. then diluted with 75 mL methylene chloride, washed with water, saturated aqueous sodium bicarbonate and saturated aqueous sodium chloride, dried over sodium sulfate and filtered. The solvent was removed under vacuum to give 61 mg (96%) of the product as a white solid which was used in the next step without further purification. FAB-MS: calculated for $C_{20}H_{25}NO_5S$ 391; found 392

(M+H). $^1$H NMR (200 MHz, CDCl$_3$): 1.38 (s, 9H), 2.95 (s, 3H), 4.20 (d, 5 Hz, 2H), 4.65 (s, 1H), 5.25 (s, 2H), 7.18–7.50 (m, 8H).

Step J: 3-Benzyloxycarbonylamino-3-methyl-N-[2,3,4,5-tetrahydro-2-oxo-1-[[2'-[(t-butoxycarbonylamino)methyl][1,1'-biphenyl]-4-yl]methyl]-1H-1-benzazepin-3(R)-yl]-butanamide To a solution of 60 mg (0.15 mmol) of 3-benzyloxycarbonylamino-3-methyl-N-[2,3,4,5-tetrahydro-2-oxo-1H-1-benzazepin-3(R)-yl]butanamide (Step D) in 0.5 mL of dry dimethylformamide under nitrogen was added 6.4 mg (0.16 mmol) of 60% sodium hydride/oil dispersion. After stirring for 15 minutes, a solution of 60 mg (0.15 mmol) of 2'-[(t-butoxycarbonylamino)methyl]-1,1'-biphenyl-4-methanol, methanesulfonate ester (Step I) in 0.5 mL of dimethylformamide was aded by cannula. The flask which originally contained the methanesulfonate ester was rinsed with 0.5 mL of dimethylformamide which was added to the reaction mixture. After stirring at room temperature for two hours, the reaction mixture was diluted with 75 mL of ethyl acetate, washed with 20 mL of water and 20 mL of saturated aqueous sodium chloride. The organic layer was dried over magnesium sulfate, filtered and the solvent removed under vacuum. The residue was purified by flash chromatography on silica gel eluting with ethyl acetate/hexane (60:40) to afford 89 mg (96%) of the product as a white foam. FAB-MS: calculated for C$_{42}$H$_{48}$N$_4$O$_6$ 704; found 705 (M+H). $^1$H NMR (200 MHz, CDCl$_3$); 1.31 (s, 3H), 1.32 (s, 3H), 1.37 (s, 9H), 1.76 (s, 1H), 2.30–2.62 (m, 5H), 4.15 (d, 5 Hz, 2H), 4.40–4.60 (m, 2H), 4.85 (d, 14 Hz, 1H), 4.95 (d, 10 Hz, 1H), 5.04 (d, 10 Hz, 1H), 5.18 (d, 14 Hz, 1H), 5.65 (s, 1H), 6.70 (d, 6 Hz, 1H), 7.10–7.42 (m, 17H).

Step K: 3-Benzyloxycarbonylamino-3-methyl-N-[2,3,4,5-tetrahydro-2-oxo-1-[[2'-(aminomethyl)[1,1'-biphenyl]-4-yl]methyl]-1H-1-benzazepin-3(R)-yl]-butanamide, trifluoroacetate To a solution of 89 mg (0.13 mmol) of the intermediate obtained in Step J in 2 mL of dry methylene chloride was added 2 drops of anisole followed by 2 mL of trifluoroacetic acid. The mixture was stirred for two hours at room temperature then the solvent was removed under vacuum. The residue was dissolved in 5 mL of carbon tetrachloride and the solvent was removed under vacuum. This was repeated twice, then the residue was dissolved in methylene chloride and the solvent removed under vacuum to give 100 mg (>100%) of the product as a white foam (containing a minor amount of anisole). The resulting crude product was used without further purification but could be purified by reverse phase medium pressure liquid chromatography on C8 eluting with methanol/0.1% aqueous trifluoroacetic acid (65:35). FAB-MS: calculated for C$_{37}$H$_{40}$N$_4$O$_4$ 604; found 605 (M+H, 80%). $^1$H NMR (200 MHz, CD$_3$OD: 1.40 (s, 6H), 2.04 (m, 1H), 2.31 (m, 2H), 2.55 (d, 12Hz, 1H), 2.62 (m, 2H), 4.08 (s, 2H), 4.42 (dd; 8, 12Hz; 1H), 5.01 (d, 12 Hz, 1H), 5.07 (d, 14 Hz, 1H), 5.10 (d, 12 Hz, 1H), 5.15 (d, 14 Hz, 1H), 7.20–7.60 (m, 17H).

Step L: 1-(2-Trimethylsilylethoxy)methyl-1H-imidazole-4-acetic acid, ethyl ester; and 3-(2-trimethylsilylethoxy)methyl-1H-imidazole-4-acetic acid, ethyl ester To a solution of 383 gm (2.48 mmol) of 1H-imidazole-4-acetic acid ethyl ester (prepared according to the procedure of Bashkin et al; J. Org. Chem., 1990, 55, 5125–5132.) in 5 mL of dry tetrahydrofuran under a nitrogen atmosphere was added 109 mg (2.73 mmol) of 60% sodium hydride/oil dispersion. The resulting mixture was stirred for 30 minutes at which time was added dropwise by syringe 0.53 mL (3.0 mmol) of 2-trimethylsilylethoxymethyl chloride. The reaction mixture was stirred for 4 hours at room temperature then diluted with 150 mL of ethyl acetate. The solution was washed with saturated aqueous sodium bicarbonate, dried over magnesium sulfate, filtered and the solvent removed under vacuum. The resulting material was purified by column chromatography on silica gel, eluting with chloroform/10% concentrated ammonium hydroxide in methanol (96:4), to afford 342 mg (48%) of the products in a 1.5:1 ratio of N-1:N-3 imidazole regioisomers as a colorless oil. FAB-MS: calculated for C$_{13}$H$_{24}$N$_2$O$_3$Si 284; found 285 (M+H, 100%). $^1$H NMR (200 MHz, CDCl$_3$): 0.00 (s, 18H), 0.90 (m, 4H), 1.25 (t, 7 Hz, 6H), 3.45 (m, 4H), 3.65 (s, 2H), 3.70 (s, 2H), 4.15 (m, 4H), 5.20 (s, 2H), 5.35 (s, 2H), 7.00 (s, 1H), 7.02 (s, 1H), 7.65 (s, 1H), 7.97 (s, 1H).

Step M: 1-(2-Trimethylsilyethoxy)methyl-1H-imidazole-4-acetic acid, lithium salt, and 3-(2-trimethylsilylethoxy)methyl-1 H-imidazole-4-acetic acid, lithium salt To a solution of 312 mg (1.10 mmol) of the mixture of intermediates obtained in Step L in 2 mL of tetrahydrofuran/water (3:1) was added 48 mg (1.2 mmol) of lithium hydroxide monohydrate. The mixture was stirred for 30 minutes at room temperature and then the solvent was removed under vacuum. Excess water was removed by azeotroping with benzene (3×5 mL) and the resulting solid was dried under vacuum overnight to afford 288 mg (100%) of the products as a white solid. FAB-MS (Li spike): calculated for C$_{11}$H$_{19}$LiN$_2$O$_3$Si 262; found 269 (M+Li, 100%). $^1$H NMR (200 MHz, D$_2$O): −0.1 (s, 18H), 0.85 (t, 8 Hz, 4H), 3.37 (s, 2H), 3.52 (s, 2H), 3.55 (m, 4H), 4.15 (m, 4H), 5.28 (s, 2H), 5.30 (s, 2H), 6.80 (s, 1H), 7.00 (s, 1H), 7.67 (s, 1H), 7.70 (s, 1H).

Step N: 3-Benzyloxycarbonylamino-3-methyl-N-[2,3,4,5-tetrahydro-2-oxo-1-[[2'-[[[[1-(2-trimethylsilylethoxy)methyl]imidazol-4-yl]acetamido]-methyl][1,1'-biphenyl]-4-yl]methyl]-1H-1-benzazepin-3(R)-yl]-butanamide, and 3-benzyloxycarbonylamino-3-methyl-N-[2,3,4,5-tetrahydro-2-oxo-1-[[2'-[[[[3-(2-trimethylsilylethoxy)methyl]imidazol-4-yl]acetamido]methyl]-[1,1'-biphenyl]-4-yl]methyl]1H-1-benzazepin-3(R)-yl]-butanamide To a slurry of 25 mg (0.09 mmol) of the mixture of intermediates obtained in Step M in 1.0 mL of dry methylene chloride under nitrogen at room temperature was added 0.013 mL (0.17 mmol) of triethylamine followed by 44 mg (0.10 mmol) of benzotriazol-1-yloxy-tris(dimethylamino)phosphonium hexafluorophosphate. In a separate flask was placed 45 mg (0.063 mmol) of 3-benzyloxycarbonylamino-3-methyl-N-[2,3,4,5-tetrahydro-2-oxo-1-[[2'-(aminomethyl)[1,1'-biphenyl]-4-yl]methyl]-1H-1-benzazepin-3(R)-yl]butanamide, trifluoroacetate (Step K) in 1.0 mL of dry methylene chloride under nitrogen. To this mixture was added to 0.013 mL (0.17 mmol) triethylamine. After 15 minutes, the amine free base mixture was added by cannula to the carboxylic acid lithium salt mixture. The flask which originally contained the amine salt was rinsed with 1.0 mL of methylene chloride and the resulting solution was added to the reaction mixture. The reaction mixture was stirred at room temperature for three hours. The reaction was diluted with 75 mL of ethyl acetate, and washed consecutively with 15 mL of water, 15 mL of saturated aqueous sodium bicarbonate and 15 mL of saturated aqueous sodium chloride. The organic layer was dried over sodium sulfate, filtered and the solvent removed under vacuum. The residue was purified by flash colum chromatography on silica gel eluting with chloroform/10% concentrated ammonium hydroxide in methanol (95:5) to afford 46 mg (87%) of the products as a white foam in a 1.5:1 ratio of N–1:N–3 imidazole ragioisomers. FAB-MS: calculated for $C_{48}H_{58}N_6O_6Si$ 842; found 843 (M+H, 40%). $^1$H NMR (200 MHz, $CD_3OD$): −0.07 (s, 9H), −0.06 (s, 9H), 0.85 (m, 4H), 1.32 (s, 12H), 1.92 (m, 2H), 2.25 (m, 2H), 2.42–2.68 (m, 8H), 3.40 (s, 2H), 3.48 (m, 4H), 3.58 (s, 2H), 4.20 (s, 4H), 4.35 (dd, 6.12 Hz, 2H), 4.92 (dd, 2.14 Hz, 2H), 4.96 (d, 12 Hz, 2H), 5.05 (d, 12 Hz, 2H), 5.25 (dd; 2, 14 Hz; 2H), 5.29 (s, 2H), 5.32 (s, 2H), 6.83 (s, 1H), 7.05 (s, H), 7.10–7.40 (m, 34H), 7.69 (d, 1 Hz, 1H), 7.71 (d, 1Hz, 1H).

Step O: 3-Amino-3-methyl-N-[2,3,4,5-tetrahydro-2-oxo-1-[[2'-[[(1H-imidazol-4-yl)acetamido]methyl]-[1,1'-biphenyl]-4-yl]methyl]-1H-1-benzazepin-3(R)-yl]-butanamide, di(trifluoroacetate)

A solution of 46 mg (0.055 mmol) of a mixture of the intermediates obtained in Step N in 2 mL of methanol was hydrogenated at room tmeperature and one atmosphere over 5 mg of palladium hydroxide catalyst for 2 hours. The mixture was filtered through Celite and the solvent removed under vacuum to give 40 mg of a white solid.

The solid thus obtained was dissolved in 1 mL of ethanol and treated with 2 mL of 5N aqueous hydrochloric acid. The mixture was heated at 80° C. for one hour. The solvent was removed under vacuum and the resulting material was purified by reverse phase medium pressure liquid chromatography on C8 eluting with methanol/0.1% aqueous trifluoroacetic acid (55:45) to afford 24 mg (55%) of the title compound as a white solid. FAB-MS: calculated for $C_{34}H_{38}N_6O_3$ 578; found 579 (M+H, 100%). $^1$H NMR (200 MHz, $CD_3OD$): 1.42 (s, 3H), 1.47 (s, 3H), 2.0–2.4 (m, 2H), 2.47 (d, 14 Hz, 1H), 2.50–2.70 (m, 3H), 3.65 (s, 2H), 4.25 (s, 2H), 4.40 (dd; 8, 12 Hz; 1H), 4.98 (d, 14 Hz, 1H), 5.22 (d, 14 Hz, 1H), 7.10–7.45 (m, 12H), 8.78 (d, 1 Hz, 1H).

EXAMPLE 12

3-[2(S), 3-Dihydroxypropyl]amino-3-methyl-N-[2,3,4,5-tetrahydro-2-oxo-1-[[2'-[[(1H, imidazol-4-yl)acetamido]-methyl][1,1'-biphenyl]-4-yl]methyl]-1H-1-benzazepin-3-(R)-yl]-butanamide, di(trifluoroacetate)

A solution of 513 mg (0.609 mmol) of a mixture of the intermediates obtained in Example 11, Step N in 15 mL of methanol was hydrogenated at room temperature and one atmosphere over 52 mg of palladium hydroxide for two hours. The mixture was filtered through Celite and the filtrate evaporated to dryness under vacuum to give a white solid.

To a solution of the solid in 5 mL of dry methanol was added a solution of 427 mg (3.28 mmol) of D-glyceraldehyde acetonide (used crude as prepared according to the procedure of Hertal, L. W.; Grossman, C. S.; Kroin, J. S. Syn. Comm. 1991, 21, 151–154.) in 5 mL of dry methanol. The pH of the mixture was carefully adjusted to 6.5 with glacial acetic acid (approximately 1 drop). To this mixture was added 2.5 g of dry powdered 4A molecular sieves. The resulting mixture was stirred for four hours at which time 3.0 mL (3.0 mmol) of a 1.0M solution of sodium cyanoborohydride in tetrahydrofuran was added by syringe. The reaction was stirred for 20 hours, then filtered through a pad of Celite and the solvent removed under vacuum.

The residue was dissolved in 5 mL of ethanol and 5 mL of 5N aqueous hydrochloric acid was carefully added dropwise. The resulting mixture was heated for 5 hours at 80° C. The solvent was removed under vacuum and the residue dissolved in 5 mL of methanol and treated with 3 mL of trifluoroacetic acid. The solvent was removed under vacuum and the resulting crude product purified by reverse phase sodium pressure liquid chromatography on C8, eluting with methanol/0.1% aqueous trifluoroacetic acid (50:50), to afford 293 mg (55%) of the title compound as a white solid. FAB-MS: calculated for $C_{37}H_{44}N_6O_5$ 652; found 653 (M+H, 40%). $^1$H NMR (200 MHz, $CD_3OD$): 1.35 (s, 3H), 1.37 (s, 3H), 2.0–2.4 (m, 2H), 2.50–2.72 (m, 4H), 2.94 (dd; 9, 12 Hz; 1H), 3.16 (dd; 3, 12 Hz; 1H), 3.52 (m, 2H), 3.66 (s, 2H), 3.80 (m, 1H), 4.28 (s, 2H), 4.38 (dd; 8, 12 Hz; 1H), 5.03 (d, 15 Hz, 1H), 5.13 (d, 15 Hz, 1H), 7.10–7.40 (m, 12H), 8.77 (d, 1.5 Hz, 1H).

EXAMPLE 13

3-[2(R)-Hydroxypropyl]amino-3-methyl-N-[2,3,4,5-tetrahydro-2-oxo-1-[[2'-[[(1H-imidazol-4-yl) acetamido]-methyl][1,1'-biphenyl]-4-yl]methyl]-1H-1-benzazepin-3-(R)-yl]-butanamide, di(trifluoroacetate)

Step A: 3-[2(R)-Benzyloxypropyl]amino-3-methyl-N-[2,3,4,5-tetrahydro-2-oxo-1H-1-benzazepin-3(R)-yl]-butanamide To a solution of 2.03 g (3.788 mmol) of 3-[2(R)-benzyloxypropyl]amino-3-methyl-N-[2,3,4,5-tetrahydro-2-oxo-1H-1-benzazepin-3(R)-yl]-butanamide trifluoroacetate (Example 10, Step B) in 40 mL of methylene chloride was added 40 mL of water. The mixture was stirred vigorously while sufficient solid potassium carbonate was added to adjust the pH of the aqueous layer to 10–11. Stirring was discontinued and the layers allowed to separate. The organic layer was removed and the aqueous layer extracted twice more with methylene chloride. The combined extracts were dried over potassium carbonate, filtered and solvents removed under vacuum to afford 1.53 g (3.62 mmol, 95%) of the product as a white solid. $^1$H NMR (400 MHz, DMSO-$d_6$): 1.04 (s, 3H), 1.06 (s, 3H), 1.14 (d, 7 Hz, 3H), 1.90 (m, 1H), 2.21 (m,3H), 2.60 (m,4H), 3.59 (m,1H), 4.23 (m,1H), 4.45 (d,10 Hz,1H), 4.53 (d,10 Hz,1H), 6.99 (d,8 Hz,1H), 7.12 (t,8 Hz,1H), 7.20–7.35 (m,7H), 8.72 (d,8 Hz,1H), 9.79 (s,1H).

Step B: 3-[2(R)-Benzyloxypropyl]amino-3-methyl-N-[2,3,4,5-tetrahydro-2-oxo-1-[[2'-[(t-butoxycarbonylamino)methyl][1,1'-biphenyl]-4-yl]-methyl]-1H-1-benzazepin-3(R)-yl]-butanamide To a solution of 514 mg (1.22 mmol) of 3-[2(R)-benzyloxypropyl]amino-3-methyl-N-[2,3,4,5-tetrahydro-2-oxo-1H-1-benzazepin-3(R)-yl]-butanamide in 5 mL of dry dimethylformamide under nitrogen was added 53 mg (1.34 mmol) of 60% sodium hydride/oil dispersion. After stirring for 15 minutes, a solution of 499 mg (1.28 mmol) of 2'-[(t-Butoxycarbonylamino)methyl]-1,1-biphenyl-4-methanol, methanesulfonate ester (Example 11, Step I) in 2 mL of dry dimethylformamide was added by cannula. The flask which originally contained the mesylate was rinsed with 1 mL of dimethylformamide which was added to the reaction mixture. After stirring at room temperature for 2 hours, the reaction mixture was diluted with 200 mL of ethyl acetate, washed with water (2×40 mL) and 40 mL of saturated aqueous sodium chloride. The organic layer was removed, dried over sodium sulfate, filtered and the solvent removed under vacuum. The residue was purified by flash chromatography on silica gel eluting with chloroform/10% concentrated ammonium hydroxide in methanol (94:6) to afford 872 mg (100%) of the product as a white foam. FAB-MS: calculated for $C_{44}H_{54}N_4O_5$ 718; found 719 (M+H,40%). $^1$H NMR (200 MHz, $CD_3OD$): 1.11 (s,3H), 1.12 (s,3H), 1.18 (d,6 Hz,3H), 1.39 (s,9H), 1.80–2.05

(m,1H), 2.15–2.38 (m,3H), 2.45–2.70 (m,4H), 3.70 (m,1H), 4.05 (s,2H), 4.42 (dd;5.11 Hz,1H), 4.47 (d,11 Hz, 1H, 4.60 (d,11 Hz, 1H), 4.93 (d,15 Hz, 1H), 4.47 (d,11 Hz, 1H, 4.60 (d,11 Hz, 1H), 4.93 (d,15 Hz, 1H), 7.05–7.40 (m,17H).

Step C: 3-[2(R)-Benzyloxypropyl]amino-3-methyl-N-[2, 3,4,5-tetrahydro-2-oxo-1-[[2'-(aminomethyl)-[1,1'-biphenyl]-4-yl]methyl]-1H-1-benzazepin-3(R)-yl]-butanamide, dihydrochloride To a solution of 872 mg (1.21 mmol) of the intermediate obtained in Step B in 5 mL of dry methylene chloride was added 0.198 mL (1.81 mmol) of anisole followed by 5 mL of trifluoroacetic acid. The mixture was stirred for two hours at room temperature then all volatiles were removed under vacuum. The residue was dissolved in 5 mL of carbon tetrachloride and the solvent was removed under vacuum. This was repeated twice, then the residue was dissolved in methylene chloride and the solvent removed under vacuum. The residue was dissolved in a minimal amount of methanol and treated with 20 mL of 6N aqueous hydrochloric acid. The solvent was removed under vacuum. This was repeated twice more, then the resulting solid was dried under vacuum overnight at room temperature to afford 822 mg (98%) of the product as an off-white solid. FAB-MS: calculated for $C_{39}H_{46}N_4O_3$ 618; found 619 (M+H,100%), $^1$H NMR (200 MHz, $CD_3OD$): 1.20 (d,6 Hz,3H), 1.35 (s,6H), 2.05–2.25 (m,1H), 2.25–2.48 (m,1H), 2.55–2.75 (m,4H), 2.92 (dd;2.13 Hz;1H), 3.19 (dd;2.13 Hz;1H), 3.84 (m,1H), 3.98 (s,2H), 4.45 (m,2H), 4.62 (d,11 Hz,1H), 5.03 (d,15 Hz,1H), 5.19 (d,15 Hz,1H), 7.10–7.55 (m,17H).

Step D: 3-[2(R)-Benzyloxypropyl]amino-3-methyl-N-[2, 3,4,5-tetrahydro-2-oxo-1[[2'-[[[[1-(2-trimethylsilylethoxy)methyl]imidazol-4-yl]acetamido]methyl][1, 1'-biphenyl]-4-yl]methyl]-1H-1-benzazepin-3(R)-yl]-butanamide, and 3-[2(R)-benzyloxypropyl]amino-3-methyl-N-[2,3,4,5-tetrahydro-2-oxo-1-[[2'-[[[[3-(2-trimethylsilylethoxy)methyl]imidazol-4-yl]acetamido]-methyl][1,1'-biphenyl]-4-yl]methyl]-1H-1-benzazepin-3(R)-yl]-butanamide To a slurry of 227 mg (0.094 mmol) of the intermediates obtained in Example 11 (Step N) in 7.0 mL of dry methylene chloride under nitrogen at room temperature was added 0.16 mL (1.15 mmol) of triethylamine followed by 409 mg (0.925 mmol) of benzotriazol-1-yloxy-tris(dimehtylamino)phosphonium hexafluorophosphate. In a separate flask was placed 400 mg (0.578 mmol) of the intermediate obtained in Example 13 (Step C) in 2.0 mL of dry methylene chloride under nitrogen. To this mixture was added 0.161 mL (1.15 mmol) of triethylamine. After 15 minutes the amine free base mixture was added dropwise by pipette to the carboxylic acid lithium salt mixture. The flask which originally contained the amine salt was rinsed with 1.0 mL of methylene chloride and the resulting solution was added to the reaction mixture. The reaction mixture was stirred at room temperature for 1.5 hours. The reaction was diluted with 200 mL of ethyl acetate, washed with 50 mL of water, saturated aqueous sodium bicarbonate (2×50 mL) and 50 mL saturated aqueous sodium chloride. The organic layer was removed, dried over sodium sulfate, filtered and the solvent removed under vacuum. The residue was purified by flash column chromatography on silica gel, eluting with chloroform/10% concentrated ammonium hydroxide in methanol (93:7), to afford 492 mg (99%) of the products as a white solid as a mixture of N-1:N-3 regioisomers in the ratio of 1.5:1. FAB-MS: calculated for $C_{50}H_{64}N_6O_5Si$ 856; found 857 (M+H,100). $^1$H NMR (200 MHz, $CD_3OD$): −0.074 (s,9H), −0.067 (s,9H), 0.81 (q,4H), 1.10 (s,6H), 1.12 (s,6H), 1.18 (d,6 Hz,6H), 1.92 (m,2H), 2.15–2.35 (m,6H), 2.42–2.68 (m,8H), 3.40 (s,2H), 3.45 (m,4H), 3.56 (s,2H), 4.20 (s,4H), 4.42 (dd;6.10 Hz;2H), 4.48 (d,12 Hz,2H), 4.59 (d,12 Hz,2H), 4.92 (dd;2.16 Hz;2H), 5.22 (dd;2.16 Hz;2 H), 5.27 (s,2H), 5.32 (s,2H), 6.83 (s,1H), 7.05 (s,1H), 7.09–7.40 (m,34H), 7.69 (d,1 Hz,1H), 7.71 (d,1 Hz,1H).

Step E: 3-[2(R)-Hydroxypropyl]amino-3-methyl-N-[2,3, 4,5-tetrahydro-2-oxy-1-[[2'-[[(1H-imidazol-4-yl)acetamido]methyl][1,1'-biphenyl]-45-yl]-methyl]-1H-1-benzazepin-3(R)-yl]-butanamide, di(trifluoroacetate)

To a solution of 490 mg (0.572 mmol) of a mixture of the intermediates obtained in Step D in 5 mL of ethanol was added 5 mL of 5N aqueous hydrochloric acid. The resulting mixture was heated at 80° C. for 3 hours. The solvent was removed under vacuum and the resulting material dried overnight under vacuum to afford 500 mg of an off-white solid.

A portion of the solid (429 mg) was dissolved in 15 mL of methanol and hydrogenated at ambient temperature and 50 psi over 80 mg of 50% palladium on carbon for 16 hours. The mixture was filtered through Celite and the solvent was removed under vacuum. The residue was purified by reverse phase medium pressure liquid chromatography on C8, eluting with methanol/0.1% aqueous trifluoroacetic acid (50:50), to afford 221 mg (50%) of the title compound as a white solid. FAB-MS: calculated for $C_{37}H_{44}N_6O_4$ 636; found 637 (M+H,60%). $^1$H NMR (200 MHz, $CD_3OD$): 1.18 (d,5 Hz,3H), 1.35 (s,3H), 1.37 (s,3H), 2.03–2.22 (m,1H), 2.25–2.42 (m,1H), 2.50–2.70 (m,4H), 2.78 (dd;10,12 Hz,1H), 3.06 (dd;3.12 Hz;1H), 3.65 (s,2H), 3.90 (m,1H), 4.27 (s,2H), 4.38 (dd;7.11 Hz;1H), 5.03 (d,14 Hz;1H), 5.14 (d,14 Hz,1H), 7.10–7.40 (m,12H), 8.78 (d,1 Hz,1H).

What is claimed is:

1. A compound having the formula:

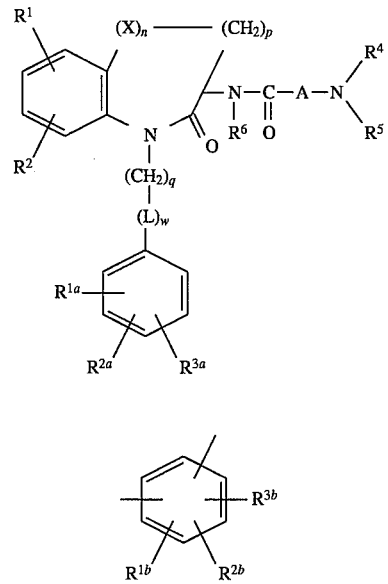

n is 0 or ;

p is 0 to 3;

q is 0 to 4;

w is 0 or 1;

X is C=O or

m is 0 to 2:

$R^1$, $R^2$, $R^{1a}$, $R^{2a}$, $R^{1b}$, and $R^{2b}$ are independently hydrogen, halogen, $C_1$-$C_7$ alkyl, $C_1$-$C_3$ perfluoroalkyl, $C_1$-$C_3$ perfluoroalkoxy, —$S(O)_m R^{7a}$, cyano, nitro, $R^{7b}O(CH_2)_v$—, $R^{7b}COO(CH_2)$ . . . —, $R^{7b}OCO(CH_2)_v$—, $R^4R^5N(CH_2)_v$—, $R^{7b}CON(R^4)(CH_2)_v$—, $R^4R^5NCO(CH_2)_v$—, phenyl or substituted phenyl where the substituents are from 1 to 3 of halogen, $C_1$-$C_6$ alkyl, $C_1$-$C_6$ alkoxy, or hydroxy; $R^{7a}$ and $R^{7b}$ are independently hydrogen, $C_1$-$C_3$ perfluoroalkyl, $C_1$-$C_6$ alkyl, substituted $C_1$-$C_6$ alkyl, where the substituents are phenyl or substituted phenyl; phenyl or substituted phenyl where the phenyl substituents are from 1 to 3 of halogen, $C_1$-$C_6$ alkyl, $C_1$-$C_6$ alkoxy, or hydroxy and v is 0 to 3;

$R^{3a}$ $R^{3b}$ are independently hydrogen or E-$R^9$, with the proviso that either $R^{3a}$ or $R^{3b}$ must be other than hydrogen;

E is:
—$(CH_2)_v$—,
—$(CH_2)_vN(R^{10})$—,
—$(CH_2)_vN(R^{10})CO(CH_2)_y$—,
—$(CH_2)_vN(R^{10})COO(CH_2)_y$—,
—$(CH_2)_vN(R^{10})CON(R^{11})(CH_2)_y$—,
—$(CH_2)_vN(R^{10})CSN(R^{11})CH_2)_y$—,
—$(CH_2)_vOC(O)(CH_2)_y$—, or
—$(CH_2)_vOCON(R^{10})(CH_2)_y$, and v and y are independently 0 to 3;
and v and y are independently 0 to 3;

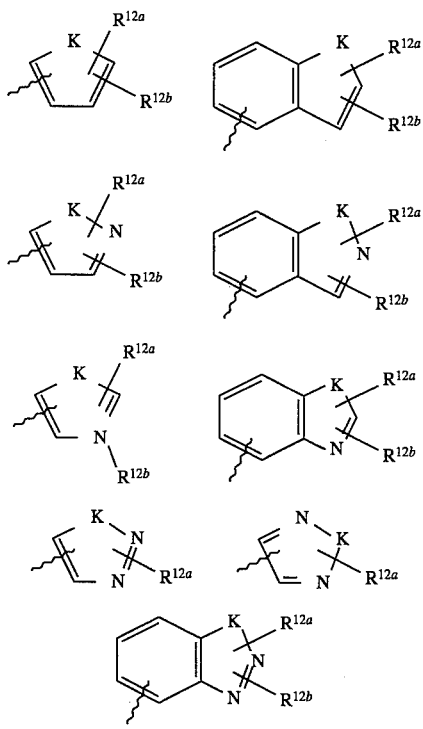

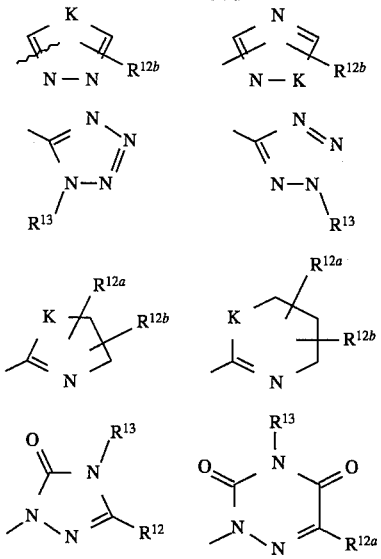

where K is O, S, or $NR^{13}$ and provided that when $R^9$ is a tetrazole, E is other than —$(CH_2)_v$—;

$R^4$ and $R^5$ are independently hydrogen, phenyl, substituted phenyl, $C_1$-$C_{10}$ alkyl, substituted $C_1$-$C_{10}$ alkyl, $C_3$-$C_{10}$ alkenyl, substituted $C_3$-$C_{10}$ alkenyl, $C_3$-$C_{10}$ alkynyl, or substituted $C_3$-$C_{10}$ alkynyl where the substituents on the phenyl, alkyl, alkenyl or alkynyl are from 1 to 5 of hydroxy, $C_1$-$C_6$ alkoxy, $C_3$-$C_7$ cycloalkyl, fluoro, $R^1$ substituted or $R^1$, $R^2$ independently disubstituted phenyl $C_1$-$C_3$ alkoxy, phenyl, $R^1$ substituted or $R^1$, $R^2$ independently disubstituted phenyl, $C_1$-$C_{20}$-alkanoyloxy, $C_1$-$C_5$ alkoxycarbonyl, carboxy, formyl, or —$NR^{10}R^{11}$ where $R^{10}$ and $R^{11}$ are independently hydrogen, $C_1$-$C_6$ alkyl, phenyl, phenyl $C_1$-$C_6$ alkyl, $C_1$-$C_5$-alkoxycarbonyl or $C_1$-$C_5$-alkanoyl-$C_1$-$C_6$ alkyl; or $R^4$ and $R^5$ can be taken together to form —$(CH_2)_rB(CH_2)_s$— where B is $CHR^1$, O, $S(O)_m$ or N—$R^{10}$, r and s are independently 1 to 3, and $R^1$ and $R^{10}$ are as defined above;

$R^{12a}$ and $R^{12b}$ are independently hydrogen, hydroxy, halogen, oxo, cyano, nitro, —$S(O)_mR^{7a}$, $C_1$-$C_3$ perfluoroalkyl, $C_1$-$C_3$ perfluoroalkoxy, $R^4R^5N(CH_2)_v$—, $R^{7b}CON(R^4)(CH_2)_v$—, $R^4R^5NCO(CH_2)_v$—, $C_1$-$C_6$ alkoxyphenyl, substituted phenyl, $C_1$-$C_{10}$ alkyl, substituted $C_1$-$C_{10}$ alkyl, where the substituents on the phenyl or alkyl are from 1 to 5 of: hydroxy, $C_1$-$C_6$ alkoxy, $C_3$-$C_7$ cycloalkyl, fluoro, $R^1$, $R^2$ independently disubstituted phenyl $C_1$-$C_3$ alkoxy, $R^1$, $R^2$ independently disubstituted phenyl, $C_1$-$C_6$ alkanoyloxy, $C_1$-$C_5$ alkoxycarbonyl, carboxy, formyl, or —$NR^{10}R^{11}$, where $R^1$, $R^2$, $R^{10}$ and $R^{11}$ are as defined above;

$R^{13}$ is hydrogen, $C_1$-$C_6$ alkyl, substituted $C_1$-$C_6$ alkyl, where the substituents are from 1 to 3 of hydroxy, $C_1$-$C_6$ alkoxy, fluoro, $R^1$, $R^2$ independently disubstituted phenyl $C_1$-$C_3$ alkoxy, $R^1$, $R^2$ independently disubstituted phenyl, $C_1$-$C_6$ alkanoyloxy, $C_1$-$C_5$ alkoxycarbonyl, carboxy, —$NR^{10}R^{11}$, where $R^1$, $R^2$, $R^{10}$ and $R^{11}$ are as defined above, $R^1$, $R^2$ independently disubstituted phenyl, or $C_1$-$C_5$ alkanoyl-$C_1$-$C_6$ alkyl;

$R^6$ is hydrogen, $C_1$-$C_{10}$ alkyl, phenyl or phenyl $C_1$-$C_{10}$ alkyl;

A is

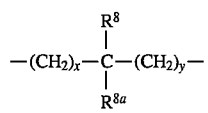

where x and y are independently 0–3;

$R^8$ and $R^{8a}$ are independently hydrogen, $C_1$–$C_{10}$ alkyl, trifluoromethyl, phenyl, substituted $C_1$–$C_{10}$ alkyl where the substituents are from 1 to 3 of imidazolyl, indolyl, hydroxy, fluoro, $S(O)_m R^{7a}$, $C_1$–$C_6$ alkoxy, $C_3$–$C_7$ ycloalkyl, $R^1$ substituted or $R^1$, $R^2$ independently disubstituted phenyl $C_1$–$C_3$ alkoxy, $R^1$ substituted or $R^1$, $R^2$ independently disubstituted phenyl, $C_1$–$C_5$-alkanoyloxy, $C_1$–$C_5$ alkoxycarbonyl, carboxy, formyl, or —$NR^{10}R^{11}$ where $R^{10}$ and $R^{11}$ are as defined above; or $R^8$ and $R^{8a}$ can be taken together to form —$(CH_2)_t$— where t is 2 to 6; and $R^8$ and $R^{8a}$ can independently be joined to one or both of $R^4$ and $R^5$ to form alkylene bridges between the terminal nitrogen and the alkyl portion of the A group wherein the bridge contains from 1 to 5 carbon atoms;

and pharmaceutically acceptable salts thereof.

2. A compound of claim 1 wherein:

n is 0;

p is 0 to 3;

q is 0 to 2;

w is 0 to 1;

m is 0 to 2;

$R^1$, $R^2$, $R^{1a}$, $R^{2a}$, $R^{1b}$, and $R^{2b}$ are independently hydrogen, halogen, $C_1$–$C_7$ alkyl, $C_1$–$C_3$ perfluoroalkyl, —$S(O)_m R^{7a}$, $R^{7b}O(CH_2)_v$—, $R^{7b}COO(CH_2)_v$—, $R^{7b}OCO(CH_2)_v$—, phenyl or substituted phenyl where the substituents are from 1 to 3 of halogen, $C_1$–$C_6$ alkyl, $C_1$–$C_6$ alkoxy, or hydroxy;

$R^{7a}$ and $R^{7b}$ are independently hydrogen, $C_1$–$C_3$ perfluoroalkyl, $C_1$–$C_6$ alkyl, substituted $C_1$–$C_6$ alkyl, where the substituents are phenyl; and v is 0 to 2;

$R^{3a}$ and $R^{3b}$ are as defined in claim 1;

$R^4$ and $R^5$ are independently hydrogen, phenyl, substituted phenyl, $C_1$–$C_{10}$ alkyl, substituted $C_1$–$C_{10}$ alkyl, where the substituents on the alkyl or phenyl are from 1 to 5 of hydroxy, $C_1$–$C_6$ alkoxy, $C_3$–$C_7$ cycloalkyl, fluoro, $R^1$ substituted or $R^1$, $R^2$ independently disubstituted phenyl $C_1$–$C_3$ alkoxy, $R^1$ substituted or $R^1$, $R^2$ independently disubstituted phenyl, $C_1$–$C_{20}$-alkanoyloxy, $C_1$–$C_5$ alkoxycarbonyl, carboxy or formyl;

$R^4$ and $R^5$ can be taken together to form —$(CH_2)_r B(CH_2)_s$— where B is $CHR^1$, O, $S(O)_m$ or N—$R^{10}$, r and s are independently 1 to 3 and $R^1$ and $R^{10}$ are as defined above;

$R^6$ is hydrogen, $C_1$–$C_{10}$ alkyl or phenyl $C_1$–$C_{10}$ alkyl;

A is

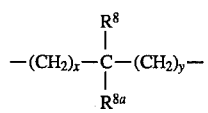

where x and y are independently 0–2;

$R^8$ and $R^{8a}$ are independently hydrogen, $C_1$–$C_{10}$ alkyl, substituted $C_1$–$C_{10}$ alkyl where the substituents are from 1 to 3 of imidazolyl, indolyl, hydroxy, fluoro, $S(O)_m R^{7a}$, $C_1$–$C_6$ alkoxy, $R^1$ substituted or $R^1$, $R^2$ independently disubstituted phenyl, $C_1$–$C_5$-alkanoyloxy, $C_1$–$C_5$ alkoxycarbonyl, carboxy, formyl, —$NR^{10}R^{11}$ where $R^{10}$ and $R^{11}$ are independently hydrogen, $C_1$–$C_6$ alkyl, or $C_1$–$C_5$ alkanoyl-$C_1$–$C_6$ alkyl; or $R^8$ and $R^{8a}$ can be taken together to form —$(CH_2)_t$— where t is 2 to 4; and $R^8$ and $R^{8a}$ can independently be joined to one or both of $R^4$ and $R^5$ to form alkylene bridges between the terminal nitrogen and the alkyl portion of the A group wherein the bridge contains from 1 to 5 carbon atoms;

and pharmaceutically acceptable salts thereof.

3. A compound of claim 2 wherein:

n is 0 p is 0 to 2;

q is 0 to 2;

w is 0 to 1;

m is 0;

$R^1$, $R^2$, $R^{1a}$, $R^{2a}$, $R^{1b}$, and $R^{2b}$ are independently hydrogen, halogen, $C_1$–$C_7$ alkyl, $C_1$–$C_3$ perfluoroalkyl, —$S(O)_m R^{7a}$, $R^{7b}O(CH_2)_v$—, $R^{7b}COO(CH_2)_v$—, $R^{7b}OCO(CH_2)_v$—, phenyl or substituted phenyl where the substituents are from 1 to 3 of halogen, $C_1$–$C_6$ alkyl, $C_1$–$C_6$ alkoxy or hydroxy;

$R^{7a}$ and $R^{7b}$ are independently hydrogen, $C_1$–$C_6$ alkyl, substituted $C_1$–$C_6$ alkyl, where the substituents are phenyl and v is 0 to 2;

$R^4$ and $R^5$ are independently hydrogen, $C_1$–$C_{10}$ alkyl, substituted $C_1$–$C_{10}$ alkyl, where the substituents on the alkyl, are from 1 to 5 of hydroxy, $C_1$–$C_6$ alkoxy, fluoro, $R^1$ substituted or $R^1$, $R^2$ independently disubstituted phenyl, $C_1$–$C_{20}$-alkanoyloxy, $C_1$–$C_5$ alkoxycarbonyl or carboxy;

$R^6$ is hydrogen or $C_1$–$C_{10}$ alkyl;

A is

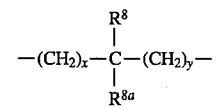

where x and y are independently 0–2;

$R^8$ and $R^{8a}$ are independently hydrogen, $C_1$–$C_{10}$ alkyl, substituted $C_1$–$C_{10}$ alkyl where the substituents are from 1 to 3 of imidazolyl, indolyl, hydroxy, fluoro, $S(O)_m R^{7a}$, $C_1$–$C_6$ alkoxy, $R^1$ substituted or $R^1$, $R^2$ independently disubstituted phenyl, $C_1$–$C_5$-alkanoyloxy, $C_1$–$C_5$ alkoxycarbonyl, carboxy; or $R^8$ and $R^{8a}$ can be taken together to form —$(CH_2)_t$— where t is 2; and $R^8$ and $R^{8a}$ can independently be joined to one or both of $R^4$ and $R^5$ to form alkylene bridges between the terminal nitrogen and the alkyl portion of the A group wherein the bridge contains from 1 to 5 carbon atoms;

and pharmaceutically acceptable salts thereof.

4. A compound of claim 3 wherein:

n is 0;

p is 0 to 2;

q is 1;

w is 1;

m is 0 or 1;

$R^1$, $R^2$, $R^{1a}$, $R^{2a}$, $R^{1b}$, and $R^{2b}$ are independently hydrogen, halogen, $C_1$–$C_7$ alkyl, $C_1$–$C_3$ perfluoroalkyl, —S(O)$_m$R$^{7a}$, R$^{7b}$O(CH$_2$)$_v$—, R$^{7b}$COO(CH$_2$)$_v$—, phenyl or substituted phenyl where the substituents are from 1 to 3 of halogen, C$_1$–C$_6$ alkyl, C$_1$–C$_6$ alkoxy, or hydroxy; R$^{7a}$ and R$^{7b}$ are independently hydrogen, C$_1$–C$_6$ alkyl, substituted C$_1$–C$_6$ alkyl, where the substituents are phenyl, and v is 0 to 1;

R$^4$ and R$^5$ are independently hydrogen, C$_1$–C$_{10}$ alkyl, substituted C$_1$–C$_{10}$ alkyl, where the substituents on the alkyl are from 1 to 3 of hydroxy, C$_1$–C$_3$ alkoxy, fluoro, R$^1$ substituted or R$^1$, R$^2$ independently disubstituted phenyl, C$_1$–C$_5$ alkanoyloxy, C$_1$–C$_{20}$ alkoxycarbonyl or carboxy;

R$^6$ is hydrogen;

A is

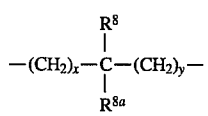

where x and y are independently 0–1;

R$^8$ and R$^{8a}$ are independently hydrogen, C$_1$–C$_{10}$ alkyl, substituted C$_1$–C$_{10}$ alkyl where the substituents are from 1 to 3 of imidazolyl, indolyl, hydroxy, fluoro, S(O)$_m$R$^{7a}$, C$_1$–C$_6$ alkoxy, R$^1$ substituted or R$^1$, R$^2$ independently disubstituted phenyl, C$_1$–C$_5$-alkanoyloxy, C$_1$–C$_5$ alkoxycarbonyl, carboxy; or R$^8$ and R$^{8a}$ can be taken together to form —(CH$_2$)$_t$— where t is 2; and R$^8$ and R$^{8a}$ can independently be joined to one or both of R$^4$ and R$^5$ to form alkylene bridges between the terminal nitrogen and the alkyl portion of the A group wherein the bridge contains from 1 to 5 carbon atoms; and pharmaceutically acceptable salts thereof.

5. A stereospecific compound of claim 1 having the following structural formula:

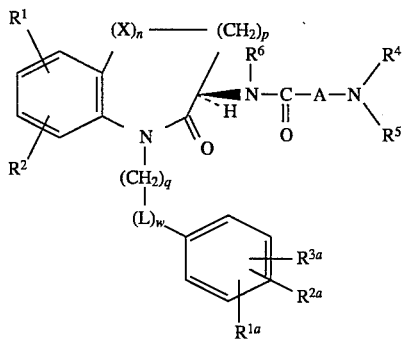

where R$^1$, R$^2$, X, n, p, q, L, w, R$^{1a}$, R$^{2a}$, R$^{3a}$, R$^4$, R$^5$, R$^6$, and A are as defined in claim 1.

6. A compound of claim 1 which is:

3-[2(S),3-Dihydroxypropyl]amino-3-methyl-N-[2,3,4,5-tetrahydro-2-oxo-1-[[2'-(1H-imidazol-2-yl)[1,1'-biphenyl]-4-yl]methyl]-1H-1-benzazepin-3(R)-yl]-butanamide;

3-[(2(R)-Hydroxypropyl)amino]-3-methyl-N-[2,3,4,5-tetrahydro-2-oxo-1-[[2'-(1H-imidazol-4-yl)[1,1'-biphenyl]-4-yl]methyl]-1H-1-benzazepin-3(R)-yl]-butanamide;

3-[2(S),3-Dihydroxypropyl]amino-3-methyl-N-[2,3,4,5-tetrahydro-2-oxo-1-[[2'-(1H-imidazol-4-yl)[1,1'-biphenyl]-4-yl]methyl]-1H-1-benzazepin-3(R)-yl]-butanamide;

3-[(2(R)-Hydroxypropyl)amino]-3-methyl-N-[2,3,4,5-tetrahydro-2-oxo-1-[[2'-(1H-1,2,3-triazol-4-yl)-[1,1'-biphenyl]-4-yl]methyl]-1H-1-benzazepin-3-(R)-yl]-butanamide;

3-[2(S),3-Dihydroxypropyl]amino-3-methyl-N-[2,3,4,5-tetrahydro-2-oxo-1-[[2'-(1H-1,2,3-triazol-4-yl)-[1,1'-biphenyl]-4-yl]methyl]-1H-1-benzazepin-3-(R)-yl]-butanamide;

3-[(2(R)-Hydroxypropyl)amino]-3-methyl-N-[2,3,4,5-tetrahydro-2-oxo-1-[[2'-[(4,5-dihydro-2-oxazolyl)amino][1,1'-biphenyl]-4-yl]methyl]-1H-1-benzazepin-3(R)-yl]-butanamide;

3-[2(S),3-Dihydroxypropyl]amino-3-methyl-N-[2,3,4,5-tetrahydro-2-oxo-1-[[2'-[(4,5-dihydro-2-oxazolyl)amino][1,1'-biphenyl]-4-yl]methyl]-1H-1-benzazepin-3(R)-yl]-butanamide;

3-[(2(R)-Hydroxypropyl)amino]-3-methyl-N-[2,3,4,5-tetrahydro-2-oxo-1-[[2'-[(4,5-dihydro-2-oxazolyl)amino][1,1'-biphenyl]-4-methyl]-1H-1-benzazepin-3-(R)-yl]-butanamide;

3-[2(S),3-Dihydroxypropyl]amino-3-methyl-N-[2,3,4,5-tetrahydro-2-oxo-1-[[2'-[(4,5-dihydro-2-oxazolyl)amino][1,1'-biphenyl]-4-yl]methyl]-1H-1-benzazepin-3(R)-yl]-butanamide;

3-[2-(R)-Hydroxypropyl]amino-3-methyl-N-[2,3,4,5-tetrahydro-2-oxo-1-[[2'-[[(1H-imidazol-4-yl)-acetamido]methyl][1,1'-biphenyl]-4-yl]methyl]-1H-1-benzazepin-3(R)-yl]-butanamide;

3-[2(S),3-Dihydroxypropyl]amino-3-methyl-N-[2,3,4,5-tetrahydro-2-oxo-1-[[(1H-imidazol-4-yl)acetamido]methyl][1,1'-biphenyl]-4-methyl]-1H-1-benzazepin-3(R)-yl]-butanamide;

3-Amino-3-methyl-N-[2,3,4,5-tetrahydro-2-oxo-1-[[2'-[(4,5-dihydro-1H-imidazol-2-yl)amino][1,1'-biphenyl]-4-yl]methyl]-1H-1-benzazepin-3(R)-yl]-butanamide;

3-[(2(R)-Hydroxypropyl)amino]-3-methyl-N-[2,3,4,5-tetrahydro-2-oxo-1-[[2'-[4,5-dihydro-1H-imidazol-2-yl)amino][1,1'-biphenyl]-4-yl]methyl]-1H-1-benzazepin-3(R)-yl]-butanamide;

3-[2(S),3-Dihydroxypropyl]amino-3-methyl-N-[2,3,4,5-tetrahydro-2-oxo-1-[[2'-[(4,5-dihydro-1H-imidazol-2-yl)amino][1,1'-biphenyl]-4-yl]-methyl]-1H-1-benzazepin-3(R)-yl]-butanamide;

3-Amino-3-methyl-N-[2,3,4,5-tetrahydro-2-oxo-1-[[

3-Amino-3-methyl-N-[2,3,4,5-tetrahydro-2-oxo-1-[[2'-[(1H-imidazol-2-yl)amino][1,1'-biphenyl]-4-yl]methyl]-1H-imidazol-2-yl)amino][1,1'-biphenyl]-4-yl]methyl]-1H-1-benzazepin-3(R)-yl]-butanamide;

3-[(2(R)-Hydroxypropyl)amino]-3-methyl-N-[2,3,4,5-tetrahydro-2-oxo-1-[[2'-[1H-imidazol-2-yl)amino]-[1,1'-biphenyl]-4-yl]methyl]-1H-1-benzazepin-3(R)-yl]-butanamide;

3-[2-(S), 3-Dihydroxypropyl]amino-3-methyl-N-[2,3,4,5-tetrahydro-2-oxo-1-[[2'-[(1H-imidazol-2-yl)amino][1,1'-biphenyl]-4-yl]methyl]-1H-1-benzaepin-3-(R)-yl]-butanamide;

3-Amino-3-methyl-N-[2,3,4,5-tetrahydro-2-oxo-1-[[2'-[(1H-tetrazol-5-yl)amino][1,1'-biphenyl]-4-yl]methyl]-1

3-[(2(R)-Hydroxypropyl)amino]-3-methyl-N-[2,3,4,5-tetrahydro-2-oxo-1-[[2'-[(1H-tetrazol-5-yl)amino]-[1,1'-biphenyl]-4yl]-methyl]-1H-1-benzazepin-3(R)-yl]-butanamide;

3-[2(S), 3-Dihydroxypropyl]amino-3-methyl-N-[2,3,4,5-tetrahydro-2-oxo-[[2'-[(1H-tetrazol-5-yl)amino][1,1'-biphenyl]-4-yl]methyl]-1H-1-benzazepin-3(R)-yl]-butanamide;

3Amino-3-methyl-N-[2,3,4,5-tetrahydro-2-oxo-1-[[2'-(4,5-dihydro-5oxo-1H-1,2,4-triazol-1-yl)-[1,1'-biphenyl]-4-yl]-methyl]-1H-1-benzazepin-3(R)-yl]-butanamide;

3-[(2(R)-Hydroxypropyl)amino]-3-methyl-N-[2,3,4,5-tetrahydro-2-oxo-1-[[2'-(4,5-dihydro-5-oxo-1H-1,2,4-triazol-1-yl)[1,1'-biphenyl]-4-yl]-methyl]-1H-1-benzazepin-3(R)-yl]-butanamide;

3-[2(S), 3-Dihydroxypropyl]amino-3-methyl-N-[2,3,4,5-tetrahydro-2-oxo-1-[[2'-(4,5-dihydro-5-oxo-1H-1,2,4,-triazol-1-yl)[1,1'-biphenyl]-4-yl]-methyl]-1H-1-benzazepin-3(R)-yl]-butanamide;

3-Amino-3-methyl-N-[2,3,4,5-tetrahydro-2-oxo-1-[[2'-(4,5-dihydro-3,5-dioxo-1,2,4-triazin-2(3H)-yl)[1,1'-biphenyl]-4-yl]methyl]-1H-1-benzazepin-3(R)-yl]-butanamide;

3-[(2(R)-Hydroxypropyl)amino]3-methyl-N-[2,3,4,5-tetrahydro-2-oxo-1-[[2'-(4,5-dihydro-3,5-dioxo-1,2,4-triazin-2(3H)-yl)[1,1'-biphenyl]-4-yl]methyl]-1H-1-benzazepin-3(R)-yl]-butanamide;

3-[2(S), 3-Dihydroxypropyl]amino-3-methyl-N-[2,3,4,5-tetrahydro-2-oxo-1-[2'-[(4,5-dihydro-3,5-dioxo-1,2,4-triazin-2(3H)-yl)[1,1'-biphenyl]-4-yl]-methyl]-1H-1-benzazepin-3(R)-yl]-butanamide;

2-Amino-2-methyl-N-[2,3,4,5-tetrahydro-2-oxo-1-[[2'-(1H-imidazol-2-yl)[1,1'-biphenyl]-4-yl]-methyl]-1H-1-benzazepin-3(R)-yl]-propanamide;

2-Amino-2-methyl-N-[2,3,4,5-tetrahydro-2-oxo-1-[[2'-(1H-imidazol-4-yl)[1,1'-biphenyl]-4-yl]-methyl]-1H-1-benzazepin-3(R)-yl]-propanamide;

2-Amino-2-methyl-N-[2,3,4,5-tetrahydro-2-oxo-1-[[2'-(1H-1,2,3-triazol-4-yl)[1,1'-biphenyl]-4-yl]-methyl]-1H-1-benzazepin-3(R)-yl]-propanamide;

2-Amino-2-methyl-N-[2,3,4,5-tetrahydro-2-oxo-1-[[2'-(1H-1,2,4-triazol-3-yl)[1,1'-biphenyl]-4-yl]-methyl]-1H-1-benzazepin-3(R)-yl]-propanamide;

2-Amino-2-methyl-N-[2,3,4,5-tetrahydro-2-oxo-1-[[2'-[(4,5-dihydro-2-oxazolyl)amino][1,1'-biphenyl]-4yl-methyl]-1H-1-benzazepin-3(R)-yl]-propanamide;

2-Amino-2-methyl-N-[2,3,4,5-tetrahydro-2-oxo-1-[[2'-[[(1H-imidazol-4-yl)acetamido]methyl][1,1'-biphenyl]-4-yl]methyl]-1H-1-benzazepin-3(R)-yl]-propanamide;

2-Amino-2-methyl-N-[2,3,4,5-tetrahydro-2-oxo-1-2'-(4,5-dihydro-3,5-dioxo-1,2,4-triazin-2(3H)-yl)[1,1'-biphenyl]-4-yl]-methyl]-1H-1-benzazepin-3(R)-yl]-propanamide;

2-Amino-2-methyl-N-[2,3,4,5-tetrahydro-2-oxo-1-[[2'-(4,5-dihydro-5-oxo-1H-1,2,4-triazol-1-yl)-[1,1'-biphenyl]-4-yl]methyl]-1H-1-benzazepin-3(R)-yl]-propanamide;

2-Amino-2-methyl-N-[2,3,4,5-tetrahydro-2-oxo-1-[[2'-[(1H-imiazol-2-yl)amino][1,1'-biphenyl]-4-yl]methyl]-1H-1-benzazepin-3(R)-yl]-propanamide;

2-Amino-2-methyl-N-[2,3,4,5-tetrahydro-2-oxo-1-[[2'-[(1H-tetrazol-5-yl)amino][1,1'-biphenyl]-4-yl]methyl]-1H-1-benzazepin-3(R)-yl]-propanamide;

2-Amino-2-methyl-N-[2,3,4,5-tetrahydro-2-oxo-1-[[2'-[(4,5-dihydro-1H-imidazol-2-yl)amino][1,1'-biphenyl]-4-yl]methyl]-1H-1-benzazepin-3(R)-yl]-propanamide;

3-Amino-3-methyl-N-[7-trifluoromethyl-2,3,4,5-tetrahydro-2-oxo-1-[[2'-(1H-imidazol-2-yl)[1,1'-biphenyl]-4-yl]methyl]-1H-1-benzazepin-3(R)-yl]-butanamide;

3-Amino-3-methyl-N-[7-trifluoromethyl-2,3,4,5-tetrahydro-2-oxo-1-[[2'-(1H-imidazol-4-yl)[1,1'-biphenyl]-4-yl]methyl]-1H-1-benzazepin-3(R)-yl]-butanamide;

3-Amino-3-methyl-N-[7-trifluoromethyl-2,3,4,5-tetrahydro-2-oxo-1-[[2'-(1H-1,2,3-triazol-4-yl)-[1,1'-biphenyl]-4-yl]methyl]-1H-1-benzazepin-3(R)-yl]-butanamide;

3-Amino-3-methyl-N-[7-fluoro-2,3,4,5-tetrahydro-2-oxo-1-[[2'-(1H-1,2,4-triazol-3-yl)[1,1'-biphenyl]-4-yl]methyl]-1H-1-benzazepin-3(R)-yl]-butanamide;

3-Amino-3-methyl-N-[7-fluoro-2,3,4,5-tetrahydro-2-oxo-1-[[2'-[(4,5-dihydro-2-oxazolyl)amino][1,1'-biphenyl]-4-yl]methyl]-1H-1-benzazepin-3(R)-yl]-butanamide;

3-Amino-3-methyl-N-[7-fluoro-2,3,4,5-tetrahydro-2-oxo-1-[[2'-(1H-imidazol-4-yl)acetamido]methyl]-[1,1'-biphenyl]-4-yl]methyl]-1H-1-benzazepin-3(R)-yl]-butanamide;

3-[2(S), 3-Dihydroxypropyl]amino-3-methyl-N-[7-fluoro-2,3,4,5-tetrahydro-2-oxo-1-[[2'-(1H-imidazol-2-yl)[1,1'-biphenyl]-4-yl]methyl]-1H-1-benzazepin-3(R)-yl]-butanamide;

3-[(2(R)-Hydroxypropyl)amino]-3-methyl-N-[7-trifluoromethyl-2,3,4,5-tetrahydro-2-oxo-1-[[2'-(1H-imidazol-4-yl)[1,1'-biphenyl]-4-yl]methyl]-1H-1-benzazepin-3(R)-yl]-butanamide;

3-[(2(R)-Hydroxypropyl)amino]-3-methyl-N-[7-fluoro-2,3,4,5-tetrahydro-2-oxo-1-[[2'-(1H-1,2,3-triazol-4-yl)[1,1'-biphenyl]-4-yl]methyl]-1H-1-benzazepin-3(R)-yl]-butanamide;

3-[2(S), 3-Dihydroxypropyl]amino-3-methyl-N-[7-fluoro-2,3,4,5-tetrahydro-2-oxo-1-[[2'-(1H-1,2,3-triazol-4-yl)[1,1'-biphenyl]-4-yl]methyl]-1H-1-benzazepin-3(R)-yl]-butanamide;

3-[(2(R)-Hydroxypropyl)amino]-3-methyl-N-[7-trifluoromethyl-2,3,4,5-tetrahydro-2-oxo-1-[[2'-(1H-1,2,4,-triazol-3-yl)[1,1'-biphenyl]-4-yl]methyl]-1H-1-benzazepin-3(R)-yl]-butanamide;

3-[(2(R)-Hydroxypropyl)amino]-3-methyl-N-[7-fluoro-2,3,4,5-tetrahydro-2-oxo-1-[[2'-[(4,5-dihydro-2-oxazolyl)amino][1,1'-biphenyl]-4-yl]-methyl-]-1H-1-benzazepin-3(R)-yl]-butanamide;

3-[2(S), 3-Dihydroxypropyl]amino-3-methyl-N-[7-trifluoromethyl-2,3,4,5-tetrahydro-2-oxo-1-[[2'-[(4,5-dihydro-2-oxazolyl)-amino][1,1'-biphenyl]-4-yl]methyl]-1H-1-benzazepin-3(R)-yl]-butanamide;

3-[2(S), 3-Dihydroxypropyl]amino-3-methyl-N-[7-trifluoromethyl-2,3,4,5-tetrahydro-2-oxo-1-[[2'-[[(1H-imidazol-4-yl)acetamido]methyl][1,1'-biphenyl]-4-yl]methyl]-1H-1-benzazepin-3(R)-yl]-butanamide;

3-[(2(R)-Hydroxypropyl)amino]-3-methyl-N-[7-fluoro-2,3,4,5-tetrahydro-2-oxo-1-[[2'-[(1H-imidazol-2-yl)amino][1,1'-biphenyl)-4yl]-methyl]-1H-1-benzazepin-3(R)-yl]-butanamide;

3-[2(S), 3-Dihydroxypropyl]amino-3-methyl-N-(7-fluoro-2,3,4,5-tetrahydro-2-oxo-1-[[2'-[(1H-tetrazol-5-yl)amino][1,1'-biphenyl]-4yl]methyl]-1H-1-benzazepin-3(R)-yl]-butanamide;

3-[(2(R)-Hydroxypropyl)amino]-3-methyl-N-[7-fluoro-2,3,4,5-tetrahydro-2-oxo-1-[[2'-(4,5-dihydro-5-oxo-1H-1,2,4-triazol-1-yl)1,1'-biphenyl]-4-yl]methyl]-1H-1-benzazepin-3(R)-yl]-butanamide;

3-[(2(S), 3-Dihydroxypropyl]amino-3-methyl-N-[7-trifluoromethyl-2,3,4,5-tetrahydro-2-oxo-1-[[2'-(4,5-dihydro-5-oxo-1H-1,2,4-triazol-1-yl)[1,1'-biphenyl]-4-yl]methyl]-1H-1-benzazepin-3(R)-yl]-butanamide; or 3-[(2(R)-Hydroxypropyl)amino]-3-methyl-N-[7-methoxy-2,3,4,5-tetrahydro-2-oxo-1-[[2'-(4,5-dihydro-3,5- dioxo-1,2,4-triazin-2(3H)-yl)[1,1'-biphenyl]-4-yl]methyl]-1H-1-benzazepin-3(R)-yl]-butanamide.

7. A method for increasing levels of endogenous growth hormone in a human or an animal which comprises administering to such human or animal an effective amount of a compound of claim 1.

8. A composition useful for increasing the endogeneous production or release of growth hormone in a human or an animal which comprises an inert carrier and an effective amount of a compound of claim 1.

* * * * *